(12) United States Patent  (10) Patent No.: US 8,575,160 B2
Sun et al.  (45) Date of Patent: Nov. 5, 2013

(54) IMIDAZOLE DERIVATIVES AS ALDOSTERONE SYNTHASE INHIBITORS

(75) Inventors: Robert Sun, Natick, MA (US); Lauren G. Monovich, Belmont, MA (US); Sylvie Chamoin, Saint Louis (FR); John Westbrook, Woodbridge, CT (US)

(73) Assignee: Novartis AG, Basel (CH)

( * ) Notice: Subject to any disclaimer, the term of this patent is extended or adjusted under 35 U.S.C. 154(b) by 13 days.

(21) Appl. No.: 13/511,581

(22) PCT Filed: Nov. 29, 2010

(86) PCT No.: PCT/EP2010/068449
§ 371 (c)(1),
(2), (4) Date: May 23, 2012

(87) PCT Pub. No.: WO2011/064376
PCT Pub. Date: Jun. 3, 2011

(65) Prior Publication Data
US 2013/0065893 A1   Mar. 14, 2013

Related U.S. Application Data

(60) Provisional application No. 61/265,142, filed on Nov. 30, 2009.

(51) Int. Cl.
C07D 487/04 (2006.01)
A61K 31/4188 (2006.01)
A61K 31/428 (2006.01)

(52) U.S. Cl.
USPC .......................................................... 514/233.2

(58) Field of Classification Search
USPC .......................................................... 514/233.2
See application file for complete search history.

(56) References Cited

U.S. PATENT DOCUMENTS 5,426,105 A   6/1995   Manning et al.

FOREIGN PATENT DOCUMENTS

| WO | 01/07051 A1 | 2/2001 |
| WO | 01/07052 A1 | 2/2001 |
| WO | 03/011824 A1 | 2/2003 |
| WO | 2004/007465 A1 | 1/2004 |
| WO | 2004/046145 A1 | 6/2004 |
| WO | 2004/112699 A2 | 12/2004 |
| WO | 2005/080397 A2 | 9/2005 |
| WO | 2007/024945 A1 | 3/2007 |

OTHER PUBLICATIONS

Musicki and Vevert, "Syntheses of Conformationally Restricted Analogues of an Angiotensin II Receptor Antagonist. General Synthetic Approach to Functionalized Imidazo[1,5-a]pyridine Derivatives," Tetrahedron Letters 35 (50);9391-9394 (1994).

*Primary Examiner* — Jeffrey S. Lundgren
*Assistant Examiner* — Zenab Olabowale
(74) *Attorney, Agent, or Firm* — Sophie Binet-Cross

(57) ABSTRACT

The present invention provides a compound of formula (I) or pharmaceutically acceptable salt thereof, wherein the variables $R^1$, $R^2$, $R^3$, $R^4$, $R^5$, $R^7$ and p are defined herein. The invention also relates to a method for manufacturing the compounds of the invention, and its therapeutic uses. The present invention further provides a combination of pharmacologically active agents and a pharmaceutical composition.

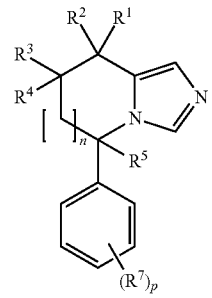

15 Claims, No Drawings

IMIDAZOLE DERIVATIVES AS ALDOSTERONE SYNTHASE INHIBITORS

This application is a U.S. National Phase filing of International Serial No. PCT/EP2010/068449 filed 29 Nov. 2010, and claims priority to U.S. Provisional Application No. 61/265,142 filed 30 Nov. 2009, the contents of which are incorporated herein by reference in their entirety.

BACKGROUND OF THE INVENTION

The mineralocorticoid hormone aldosterone is produced by the adrenal gland and acts on the distal tubules and collecting ducts of the kidney to increase reabsorption of ions and water in the kidney. Aldosterone causes conservation of sodium, secretion of potassium, increased water retention, and increased blood pressure.

Aldosterone has been implicated in the pathogenesis of cardiovascular diseases such as hypertension and heart failure. In clinical trials, treatment with the nonselective mineralocorticoid receptor antagonist (MRA) spironolactone or the selective MRA eplerenone significantly reduced morbidity and mortality among patients with heart failure or myocardial infarction already taking an angiotensin-converting enzyme inhibitor or a β-blocker. However, significant side effects such as gynecomastia and impotence were observed in male patients receiving spironolactone while hyperkalemia was seen in patients taking either drug.

SUMMARY OF THE INVENTION

The invention pertains to the compounds, methods for using them, and uses thereof as described herein. Examples of compounds of the invention include the compounds according to anyone of Formulae I to IVB, or a pharmaceutically acceptable salt thereof and the compounds of the examples.

The invention therefore provides a compound of the Formula I:

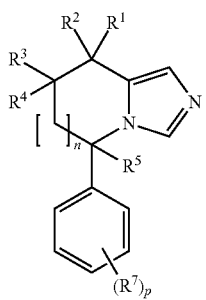

[I]

wherein $R^1$ and $R^2$ are independently OH, $C_{2-7}$alkenyloxy, $C_{2-7}$alkoxy, $C_{6-10}$aryl, aryl-$C_{2-7}$alkenyl, $C_{2-7}$alkenyl, $C_{3-8}$cycloalkyl, $C_{2-7}$alkynyl, $C_{1-7}$cycloalkyl-$C_{2-7}$alkynyl, heteroaryl, heteroaryl-$C_{1-7}$alkyl, —$CH_2C(O)OH$, —$CH_2C(O)O$—$C_{1-7}$alkyl, —$CH_2C(O)NH$—$C_{8-10}$aryl, —$CH_2C(O)NH$-heteroaryl, —$CH_2C(O)$-heterocyclyl, —$CH_2C(O)NH$-heterocyclyl, —$CH_2C(O)NH$—$C_{1-7}$alkyl, —$C(O)O$—$C_{1-7}$alkyl or —$C(O)$—$C_{1-7}$alkyl; wherein aryl, heterocyclyl and heteroaryl are optionally substituted with one or more $R^6$; with the proviso that one of $R^1$ and $R^2$ is other than $C_{1-7}$alkyl; or $R^1$ and $R^2$ form together =O, =N(OH) or =N(O—$C_{1-7}$alkyl); and $R^3$ and $R^4$ are independently selected from the group consisting of H, $C_{1-7}$alkyl, hydroxy, aryl-$C_{1-7}$alkyl or halo; wherein aryl is optionally substituted with one or more $R^8$; and $R^5$ is H, halo, hydroxy or $C_{2-7}$alkenyl; and $R^6$ and $R^8$ for each occurrence, is independently $C_{1-7}$alkyl, $C_{3-7}$cycloalkyl, halo-$C_{1-7}$alkyl, CN, OH, $NH_2$, $C_{1-7}$alkylamino, di-($C_{1-7}$alkyl)amino, heteroaryl, $C_{1-7}$alkoxy, halo, heterocyclyl, benzyloxy, halo-$C_{1-7}$alkoxy, —$OS(O)_2$—$C_{1-7}$alkyl or —$OS(O)_2$-halo $C_{1-7}$alkyl; wherein $C_{8-10}$aryl, heterocyclyl and heteroaryl are optionally substituted with one or more $R^9$;

for each occurrence, $R^7$ is independently hydrogen, $C_{2-7}$alkenyl, $C_{1-7}$alkyl, $C_{3-8}$cycloalkyl, halo, nitro, cyano, $NH_2$, halo$C_{1-7}$alkyl, $C_{1-7}$alkoxy, $C_{3-8}$cycloalkoxy, $C_{8-10}$aryloxy, $C_{8-10}$aryl, heteroaryl, $C_{6-10}$aryl-$C_{1-7}$alkyl, heteroaryl-$C_{1-7}$alkyl, heterocyclyl, heterocyclyl-$C_{1-7}$alkyl, $C(O)OR^{10}$ or $N(R^{11}R^{12})$, wherein said alkyl, alkenyl, alkoxy, aryl, heterocyclyl and heteroaryl each are optionally substituted with one or more substituent independently selected from $C_{1-7}$alkyl, hydroxy, halo, halo $C_{1-7}$alkyl, $C_{1-7}$alkoxy, nitro, cyano, di-$C_{1-7}$alkylamino, $C_{1-7}$alkylamino and $C_{1-7}$alkoxy-$C_{1-7}$alkyl;

$R^9$ for each occurrence, is independently $C_{1-7}$alkyl, $C_{1-7}$alkoxy, halo, halo$C_{1-7}$alkyl, $NH_2$, $C_{1-7}$alkylamino, di-($C_{1-7}$alkyl)amino, halo$C_{1-7}$alkoxy, CN, OH, $C(O)O$—$C_{1-7}$alkyl, $C(O)O$-halo$C_{1-7}$alkyl, carbamoyl, $C_{1-7}$alkylaminocarbonyl or di-$C_{1-7}$alkylaminocarbonyl;

$R^{10}$, $R^{11}$ and $R^{12}$ for each occurrence are independently H, $C_{1-7}$alkyl, $C_{3-8}$cycloalkyl, halo-$C_{1-7}$alkyl, $C_{6-10}$aryl, $C_{6-10}$aryl-$C_{1-7}$alkyl, heteroaryl, heteroaryl-$C_{1-7}$alkyl, heterocyclyl, heterocyclyl-$C_{1-7}$alkyl; or $R^{11}$ and $R^{13}$ taken together with the nitrogen to which they are attached form a 3- to 8-membered heterocyclyl ring or a 5-membered heteroaryl ring;

n is 0 or 1;

p is 0, 1, 2, 3, 4 and 5;

or a pharmaceutically acceptable salt thereof.

In another embodiment, the invention pertains to a method for treating a disorder or disease mediated by aldosterone synthase and/or 11-beta hydroxylase (CYP11B1) in a subject by administering to the subject a therapeutically effective amount of a compound according to anyone of Formulae I to IVB, or a pharmaceutically acceptable salt thereof, such that the disorder or disease mediated by aldosterone synthase and/or CYP11B1 in the subject is treated.

In yet another embodiment, the invention pertains to a method for treating a subject for hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke or cortisol-induced mineralocorticoid excess, comprising administering to the subject a therapeutically effective amount of a compound according to anyone of Formulae I to IVB, or a pharmaceutically acceptable salt thereof, such that the subject is treated.

In yet another embodiment, the invention pertains to pharmaceutical compositions, comprising a compound according to anyone of Formulae I to IVB, or a pharmaceutically acceptable salt thereof, and one or more pharmaceutically acceptable carrier.

In still another embodiment, the invention pertains to combinations of a compound according to anyone of Formulae I to IVB or a pharmaceutically acceptable salt thereof and one or more additional therapeutically active agent.

In another embodiment, the invention pertains to a method for inhibiting aldosterone synthase and/or CYP11B1 in a subject by administering to the subject a therapeutically effective amount of a compound according to anyone of Formulae I to IVB, or a pharmaceutically acceptable salt thereof, such that aldosterone synthase and/or CYP11B1 is inhibited.

DETAILED DESCRIPTION OF THE INVENTION

Definition:

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms. Representative examples of alkyl include methyl, ethyl, n-propyl, iso-propyl, n-butyl, sec-butyl, isobutyl, Pert-butyl, n-pentyl, isopentyl, neopentyl, n-hexyl, 3-methylhexyl, 2,2-dimethylpentyl, 2,3-dimethylpentyl, n-heptyl. The term "$C_{1-7}$alkyl" refers to a hydrocarbon having one to seven carbon atoms.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-7}$alkyl" refers to a hydrocarbon having one to seven carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

The term "alkoxylalkyl" refers to $C_{1-7}$ alkyl substituted with one or more alkoxy.

The term "alkynyl" refers to a branched or unbranched hydrocarbon having at least one carbon-carbon triple bond. The term "$C_{2-7}$-alkynyl" refers to a hydrocarbon having two to seven carbon atoms and comprising at least one carbon-carbon triple bond. Representative examples of alkynyl are ethynyl, prop-1-ynyl, butynyl, isopropynyl or isobutynyl.

The term "alkenyl" refers to a branched or unbranched hydrocarbon having at least one carbon-carbon double bond. The term "$C_{2-7}$alkenyl" refers to a hydrocarbon having from two to six carbon atoms and comprising at least one carbon-carbon double bond. Representative examples of alkenyl are vinyl, prop-1-enyl, allyl, butenyl, isopropenyl or isobutenyl.

The term "alkenyoxy" refer to alkenyl-O— wherein alkenyl has the definition above.

As used herein, the term "cycloalkyl" refers to saturated or partially unsaturated monocyclic, bicyclic or tricyclic hydrocarbon groups of 3-12 carbon atoms, preferably 3-8, or 3-7 carbon atoms. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-8}$ cycloakyl" refers to a cyclic hydrocarbon groups having 3 to 8 carbon atoms.

The term "amino" includes compounds where a nitrogen atom is covalently bonded to at least one carbon or heteroatom. The term includes "$C_{1-7}$ alkyl-amino" which comprises groups and compounds wherein the nitrogen is bound to at least one additional $C_{1-7}$ alkyl group ($C_{1-7}$ alkyl-NH—). The term "di-$C_{1-7}$ alkyl amino" includes groups wherein the nitrogen atom is bound to at least two additional $C_{1-7}$ alkyl groups (($C_{1-7}$alkyl)$_2$N—) which alkyl group can be the same of different.

The term "carbamoyl" includes "aminocarbonyl". Representative examples of carbamoyl are aminocarbonyl (i.e. $H_2NC(O)$—), $C_{1-7}$ alkylaminocarbonyl (i.e. $C_{1-7}$ alkyl-NHC(O)—), di-$C_1$ alkylaminocarbonyl (i.e. ($C_{1-7}$ alkyl)$_2$NC (O)—).

The term "cycloalkyl-alkynyl" refers to an alkynyl substituted with cycloalkyl.

The term "aryl" refers to monocyclic or bicyclic aromatic hydrocarbon groups having 6-10 carbon atoms in the ring portion. The term "aryl" also refers to a group in which an aromatic ring is fused to one or more cycloalkyl rings or heterocyclyl rings, where the radical or point of attachment is on the aromatic ring or on the fused cycloalkyl or heterocyclyl ring. Representative examples of aryl are phenyl, naphthyl, hexahydroindyl, indanyl, benzo[d][1,2]dioxolyl or tetrahydronaphthyl. The term "$C_{6-10}$ aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-$CH_2CH_2$—. The term "$C_{6-10}$aryl-$C_{1-7}$alkyl" refers to a hydrocarbon having one to seven carbon atoms, which hydrocarbon is substituted with an aryl having 6 to 10 carbon atoms.

The term "Heteroaryl" includes aromatic monocyclic or bicyclic heteroaryl, containing from 5-10 ring members selected from carbon atoms and 1 to 5 heteroatoms, and each heteroatoms is independently selected from O, N or S, where the N and S can be oxidized to various oxidation states. Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl and pyrimidin-5-yl. The term "heteroaryl" also refers to a group in which a heteroaromatic ring is fused to one or more aryl, cycloaliphatic, or heterocyclyl rings, where the radical or point of attachment is on the heteroaromatic ring or on the fused aryl, cycloaliphatic or heterocyclyl rings. Representative examples of bicyclic heteroaryl are azaindolyl, indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

The term "heteroarylalkyl" refers to $C_{1-7}$ alkyl substituted with heteroaryl.

As used herein, the term "heterocyclyl" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. In one embodiment, heterocyclyl moiety represents a saturated monocyclic ring containing from 5-7 ring atoms and containing 1, 2 or 3 heteroatoms. The heterocyclyl group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, azindinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "heterocyclylalkyl" refers to $C_{1-7}$ alkyl substituted with heterocyclyl.

The term "hydroxy" or "hydroxyl" includes groups with an —OH.

The term "halogen" includes fluorine, bromine, chlorine and iodine.

The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In one embodiment the heteroatom is nitrogen, oxygen or sulfur.

Compound of the Invention:

Various embodiments of the invention are described herein. It will be recognized that features specified in each embodiment may be combined with other specified features to provide further embodiments.

In one embodiment, the invention pertains to compounds of Formula I or a pharmaceutically acceptable salt thereof, wherein one of $R^1$ and $R^2$ is OH, $C_{1-7}$alkoxy or Alkenyloxy and the other is $C_{6-10}$aryl, $C_{6-10}$aryl-$C_{1-7}$alkenyl, $C_{2-7}$alkenyl, $C_{1-7}$-alkyl, $C_{2-7}$alkynyl, heteroaryl, heteroaryl-$C_{1-7}$alkyl, —$CH_2C(O)OH$, —$CH_2C(O)O$—$C_{1-7}$alkyl, —$CH_2C(O)NH$—$C_{6-10}$aryl, —$CH_2C(O)NH$-heteroaryl, —$CH_2C(O)$-heterocyclyl, —$CH_2C(O)NH$-heterocyclyl, —$CH_2C(O)NH$—$C_{1-7}$alkyl, —$C(O)O$—$C_{1-7}$alkyl or —$C(O)$—$C_{1-7}$alkyl; wherein aryl, heterocyclyl and heteroaryl are optionally substituted with one or more $R^6$. This embodiment is illustrated by compounds of Formula II:

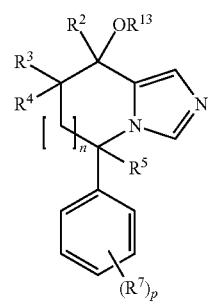

II or a pharmaceutically acceptable salt thereof wherein $R^2$, $R^3$, $R^4$, $R^5$, $R^7$, n and p have the definitions of Formulae I and II, supra and $R^{13}$ is H, $C_{1-7}$alkyl or $C_{2-7}$alkenyl. In one aspect of this embodiment, $R^{13}$ is H. In another aspect of this embodiment, $R^2$ is $C_{6-10}$aryl, $C_{6-10}$aryl-$C_{1-7}$alkyl, $C_{6-10}$alkenyl, $C_{2-7}$alkenyl, $C_{1-7}$alkyl, $C_{2-7}$alkynyl, heteroaryl, heteroaryl-$C_{1-7}$-alkyl, —$CH_2C(O)OH$, —$CH_2C(O)NH$—$C_{6-10}$aryl, —$CH_2C(O)NH$-heteroaryl or —$CH_2C(O)$-heterocyclyl wherein aryl, heterocyclyl and heteroaryl are optionally substituted with one or more $R^6$.

Certain compounds of Formula include compounds of Formula IIA:

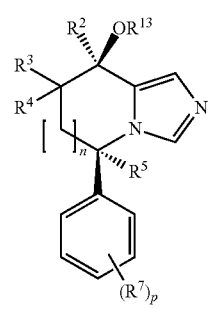

IIA or a pharmaceutically acceptable salt thereof, wherein $R^2$, $R^3$, $R^4$, $R^5$, $R^7$, $R^{13}$, n and p have the definitions of Formulae I and II, supra.

Certain compounds of Formula II include compounds of Formula IIB:

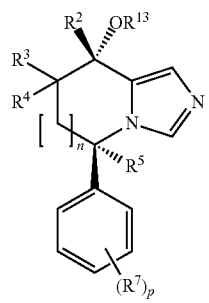

IIB or a pharmaceutically acceptable salt thereof, wherein $R^2$, $R^3$, $R^4$, $R^5$, $R^7$, $R^{13}$, n and p have the definitions of Formulae I and II, supra.

In one embodiment, the invention pertains to compounds of Formula II, IIA or IIB or a pharmaceutically acceptable salt thereof, wherein $R^2$ is alkyl (i.e. methyl, ethyl, propyl, butyl, isopropyl).

In another embodiment, the invention pertains to compounds of Formula II, IIA or IIB or a pharmaceutically acceptable salt thereof, wherein $R^2$ is optionally substituted heteroaryl or heteroaryl-$C_{1-7}$alkyl. In one aspect of this embodiment, $R^2$ is optionally substituted heteroaryl. In a further aspect of this embodiment, $R^2$ is a monocyclic heteroaryl which is optionally substituted with one or more $R^6$. Representative examples of $R^2$ are pyridine, pyrimidine, pyrazine, thiazole, imidazole, pyrazole, pyrrole, thiophene, oxazole and isooxazole, each of which is optionally substituted with one or more $R^6$. In a further embodiment, $R^2$ is pyridine which is optionally substituted with one or more $R^6$. In another further aspect of this embodiment, $R^2$ is optionally substituted bicyclic heteroaryl. Representative examples are azaindole, pyrrolopyridine, benzothiazole, quinoline, benzothiophene, indole, quinazoline, benzoxazole, benzimidazole, indazole and imidazopyridine, each of which is optionally substituted with one or more $R^6$. In a further aspect, $R^2$ is pyrrolopyridine, benzothiazole, quinoline, benzothiophene and indole, each of which is optionally substituted with one or more $R^6$.

In another embodiment, the invention pertains to compounds of Formula II, IIA or IIB or a pharmaceutically acceptable salt thereof, wherein $R^2$ is $C_{6-10}$aryl or $C_{6-10}$aryl-$C_{1-7}$alkyl (i.e. benzyl, $PhCH_2CH_2$), each of which is optionally substituted with one or more $R^6$. In one aspect of this embodiment, $R^2$ is benzyl, phenyl or naphthyl, each of which is optionally substituted with one or more $R^6$. In another aspect of this embodiment, $R^2$ is phenyl optionally substituted with one or more $R^6$. This embodiment is illustrated by compounds of Formulae III, IIIA and IIIB.

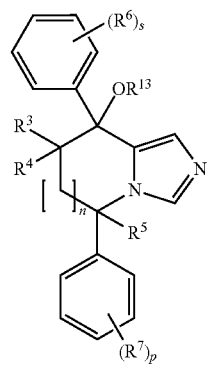

III

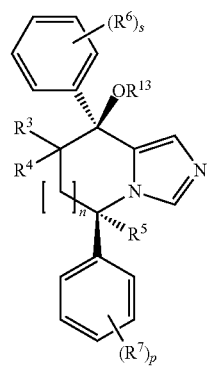

IIIA

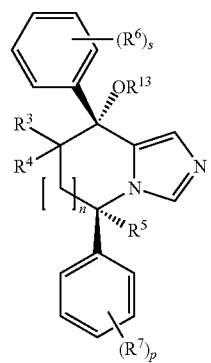

IIIB or a pharmaceutically acceptable salt thereof, wherein $R^2$, $R^3$, $R^4$, $R^5$, $R^6$, $R^7$, $R^{13}$, n and p have the definitions of Formulae I and II, supra and s is 0, 1, 2, 3, 4 or 5. In one aspect of this embodiment $R^6$ is $C_{1-7}$alkyl, $C_{3-7}$cycloalkyl, halo-$C_{1-7}$alkyl, CN, OH, $NH_2$, $C_{1-7}$alkylamino, di-($C_{1-7}$alkyl)amino, $C_{1-7}$alkoxy, halo, benzyloxy, halo-$C_{1-7}$alkoxy, $C_{6-10}$aryl, heteroaryl (i.e. isoxazole, pyrazole, thiazole, pyrimidine, pyridine, thiophene) or heterocyclyl (i.e. morpholine, piperidine), wherein aryl, heteroaryl and heterocyclyl are optionally substituted with one or more $R^9$.

In another embodiment, the invention pertains to compounds of Formula II, IIA or IIB or a pharmaceutically acceptable salt thereof, wherein $R^2$ is —$CH_2C(O)NH$—$C_{6-10}$aryl, —$CH_2C(O)NH$-heteroaryl, $CH_2C(O)NH$-heterocyclyl, —$CH_2C(O)$heterocyclyl, —$CH_2C(O)OH$, —$CH_2C(O)O$—$C_{1-7}$alkyl, —$CH_2C(O)NH$—$C_{1-7}$alkyl, —$CH_2C(O)NH$-heterocyclyl wherein alkyl, aryl, heteroaryl and heterocyclyl are optionally substituted with one or more $R^6$. In one aspect of this embodiment $R^2$ is $CH_2C(O)NH$—$C_{6-10}$aryl, —$CH_2C(O)NH$-heteroaryl or —$CH_2C(O)$heterocyclyl, wherein the heterocyclyl may be linked to the carbonyl (C(O)) via a carbon or a nitrogen (i.e. N-pyrrolidine, N-morpholine) and wherein aryl, heteroaryl and heterocyclyl are optionally substituted with one or more $R^6$. In a further aspect, $R^2$ is $CH_2C(O)NH$—$C_{6-10}$aryl, —$CH_2C(O)NH$-heteroaryl, wherein aryl and heteroaryl are optionally substituted with one or more $R^6$. This is illustrated by compounds of Formulae IV, IVA and IVB:

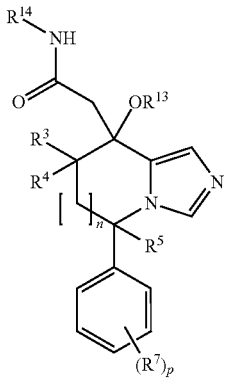

IV

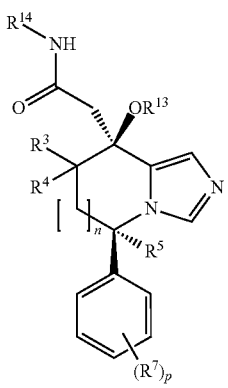

IVA

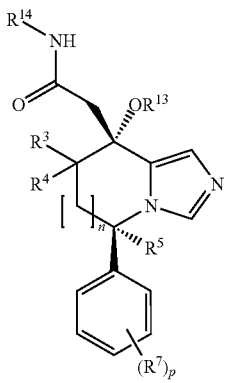

IVB or a pharmaceutically acceptable salt thereof, wherein $R^2$, $R^3$, $R^4$, $R^5$, $R^7$, $R^{13}$, n and p have the definitions of Formulae I and II, supra and $R^{14}$ is $C_{6-10}$aryl, $C_{6-10}$aryl-$C_{1-7}$alkyl or heteroaryl, heteroaryl-$C_{1-7}$alkyl, each of which is optionally substituted with one or more $R^6$. Representative examples of $R^{14}$ are thiazole, pyridine, phenyl, benzyl; each of which is optionally substituted with one or more $R^6$.

Another embodiment includes compounds according to anyone of Formulae I, II, IIA, IIB, III, IIIA, IIIB, IV, IVA or IVB or of any classes and subclasses described supra, wherein n is 1 or a pharmaceutically acceptable salt thereof.

Another embodiment includes compounds according to anyone of Formulae I, II, IIA, IIB, III, IIIA, IIIB, IV, IVA or IVB or of any classes and subclasses described supra, wherein n is 0 or a pharmaceutically acceptable salt thereof.

Another embodiment includes compounds according to anyone of Formulae I, II, IIA, IIB, III, IIIA, IIIB, IV, IVA or IVB or of any classes and subclasses described supra, or a pharmaceutically acceptable salt thereof, wherein $R^3$ and $R^4$ are independently H or $C_{1-7}$alkyl. In one aspect of this embodiment, $R^3$ and $R^4$ are H.

Another embodiment includes compounds according to anyone of Formulae I, II, IIA, II, III, IIIA, IIIB, IV, IVA or IVB or of any classes and subclasses described supra, or a pharmaceutically acceptable salt thereof, wherein $R^5$ is H.

Another embodiment includes compounds according to anyone of Formulae I, II, IIA, IIB, III, IIIA, IIIB, IV, IVA or IVB or of any classes and subclasses described supra, or a pharmaceutically acceptable salt thereof, wherein $R^7$ is $C_{1-7}$alkyl, $C_{3-7}$cycloalkyl, halo-$C_{1-7}$alkyl, CN, $C_{1-7}$alkoxy, halo, halo$C_{1-7}$alkyl, or hydroxy and p is 1, 2 or 3. In a further aspect of this embodiment, p is 2, one of $R^7$ is CN and the other is halo. In yet a further embodiment, p is 2 and one of $R^7$ is para-CN and the other is ortho-halo, wherein the para and ortho positions represent the para and ortho positions to the point of attachment of the phenyl group respectively. In one representative example, p is 2, one of $R^7$ is para-CN and the other is ortho fluoro.

In another embodiment, some compounds of the invention may have selectivity for aldosterone synthase (CYP11B2) relative to 11-beta hydroxylase (CYP11B1).

In another embodiment, $R^6$ is $C_{1-7}$alkyl, $C_{3-7}$cycloalkyl, CN, $NH_2$, $C_{1-7}$alkylamino, di-($C_{1-7}$alkyl)amino, $C_{6-10}$aryl, heteroaryl, $C_{1-7}$alkoxy, halo, halo$C_{1-7}$alkoxy or hydroxy; wherein aryl and heteroaryl are optionally substituted with one or more $R^9$.

In another embodiment n, p, $R^1$, $R^2$, $R^3$, $R^4$, $R^5$, $R^6$, $R^7$, $R^6$, $R^9$ groups are those defined by the n, p, $R^1$, $R^2$, $R^3$, $R^4$, $R^5$, $R^6$, $R^7$, $R^8$, $R^9$ groups in the Examples section below.

In another embodiment, individual compounds according to the invention are those listed in the examples section below, or a pharmaceutically acceptable salt thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)- isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of, for example, the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free add forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1H$, $^2H$ or D, $^3H$); any carbon represented by "C" in any of the formulae herein is intended to represent all isotopic forms of carbon (e.g. $^{11}C$, $^{13}C$, $^{14}C$), any nitrogen represented by "N" is intended to represent all isotopic forms of nitrogen (e.g. $^{14}N$, $^{15}N$). N) Other examples of isotopes that are included in the invention include isotopes of oxygen, sulfur, phosphorous, fluorine, iodine and chlorine, such as $^{18}F$ $^{31}P$, $^{32}P$, $^{35}S$, $^{35}Cl$, $^{125}I$. The invention includes various isotopically labeled compounds as defined herein, for example those into which radioactive isotopes, such as $^3H$, $^{13}C$, and $^{14}C$ are present. In one embodiment, the atoms in the formulae herein occur in their natural abundance. In another embodiment, one or more hydrogen atom may be enriched in $^2H$; or/and one or more carbon atom may be enriched in $^{11}C$, $^{13}C$ or $^{14}C$; or/and one or more nitrogen may be enriched in $^{14}N$. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formulae I to IVB. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-enriched compounds of formulae I to IVB can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formulae I to IVB that contain groups capable of acting as donors and/or acceptors for hydrogen bonds may be capable of forming co-crystals with suitable co-crystal formers. These co-crystals may be prepared from compounds of formulae I to IVB by known co-crystal forming procedures. Such procedures include grinding, heating, co-subliming, co-melting, or contacting in solution compounds of formulae I to IVB with the co-crystal former under crystallization conditions and isolating co-crystals thereby formed. Suitable co-crystal formers include those described in WO 2004/078163. Hence the invention further provides co-crystals comprising a compound of formulae I to IVB or a pharmaceutically acceptable salt thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease or symptom thereof (i) mediated by aldosterone synthase and/or CYP11B1, or (ii) associated with aldosterone synthase and/or CYP11B1 activity, or (iii) characterized by abnormal activity of aldosterone synthase and/or CYP11B1; or (2) reduce or inhibit the activity of aldosterone synthase and/or CYP11B1; or (3) reduce or inhibit the expression of aldosterone synthase and/or CYP11B1. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of aldosterone synthase and/or CYP11B1; or at least partially reduce or inhibit the expression of aldosterone synthase and/or CYP11B1.

As used herein, the term "subject" refers to an animal. Typically the animal is a mammal, for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Aspect:

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21).—

The compounds of the invention can be synthesized using the methods described in the following schemes, examples, and by using art recognized techniques. All compounds described herein are included in the invention as compounds. Compounds of the invention may be synthesized according to at least one of the methods described in schemes 1 to 6.

Scheme 1 illustrates the synthesis of compounds of Formula I wherein $R^1$ and $R^2$ form together =O.

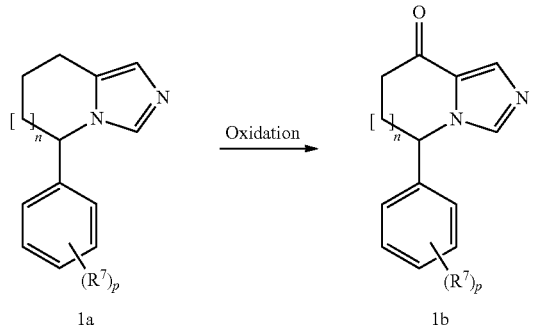

Intermediate 1a can be synthesized according to procedure described in WO 2007024945. Intermediate 1b can be prepared through an oxidation of intermediate 1a using iron(III) chloride or with $Rh_2(cap)_4$ as the catalyst and using a peroxide such as tert-butyl hydroperoxide or hydrogen peroxide as the oxidants in a base such as pyridine.

Scheme 2 illustrates the synthesis of compounds of Formula I wherein $R^1$ and $R^2$ form =O with the presence of substituents $R^3$ and $R^4$.

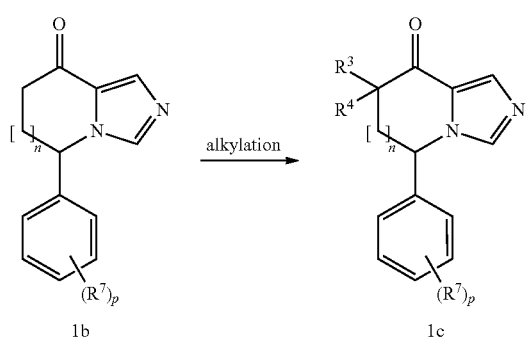

This step involves the introduction of $R^3$ and $R^4$ via an alkylation reaction of intermediate 1b. This can be achieved by deprotonating intermediate 1b in an aprotic solvent such as THF or DMF with a suitable base such as NaH or with potassium tert-butoxide. This is followed by addition of alkylating agents such as alkyl halides, various aromatic benzyl halides, various unsubstituted or substituted allyl halides to provide the bis alkylation product 1c.

Scheme 3 illustrates the synthesis of compounds of Formula I, II or III wherein one of $R^1$ and $R^2$ is OH.

Scheme 3

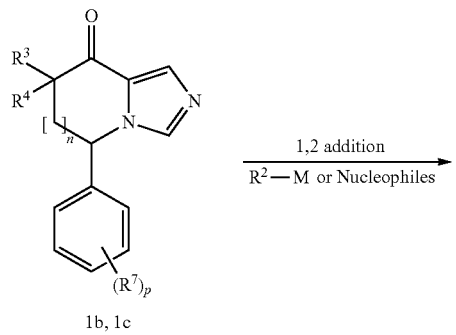

1b, 1c

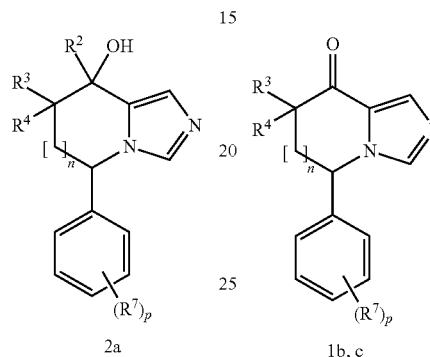

2a

This reaction involves the introduction of various substituents ($R^2$) onto the ketone intermediate 1b or 1c via a 1,2 addition reaction with a suitable nucleophile in an aprotic solvent such as THF or ethyl ether to provide alcohol products 2a. The nucleophiles are commercially available as in the case of $R^2$-M where M are Mg and Zn ($R^2$ can be non-substituted or substituted aryl, alkyl, alkenyl, bicyclic aryl). Alternatively, $R^2$-M can be prepared from a suitable aryl halides such as an aryl-bromide or an aryl-iodide via a metal-halogen exchange using reagents such as iPrMgBr, nBuLi, secBuLi, or tert-BuLi in an aprotic solvent such as THF or ethyl ether. Additionally, heterocyclic nucleophiles, alkynyl nucleophiles, and aryl-alkyl nucleophiles can be generated via deprotonating the corresponding heteroaromatics, alkynes, or aryl-alkyls with a strong base such as LDA, nBuLi, or secBuLi in an aprotic solvent such as THF or ethyl ether.

Scheme 4 illustrates the synthesis of compounds of Formula I, II or III wherein one of $R^1$ and $R^2$ is alkoxy or akenyloxy.

Scheme 4

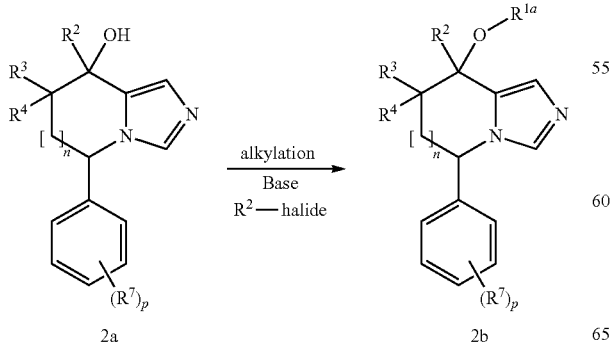

Intermediate 2b can be prepared through a general o-alkylation procedure via treatment of intermediate 2a in an aprotic solvent such as DMF or THF with a suitable base such as sodium hydride or potassium tert-butoxide. The resultant deprotonated alcohol can be alkylated with an alkylating agent such as an alkyl halide, i.e. methyl iodide, ethyl iodide, n-propyl iodide or with an allylic halide such as allyl bromide or allyl iodide to provide alkylation product 2b.

Scheme 5 illustrates the synthesis of compounds of Formula I, II or III wherein one of $R^1$ and $R^2$ is OH and the other is phenyl substituted with an aryl or a heteroaryl.

Scheme 5

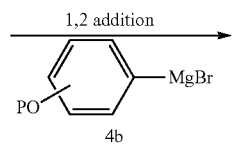

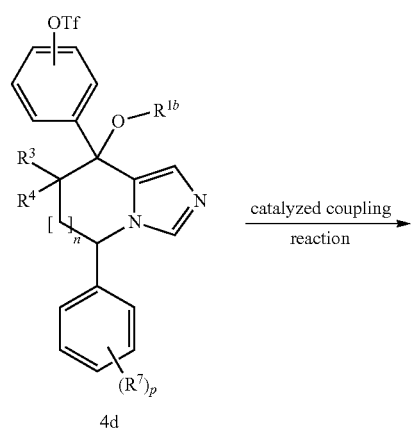

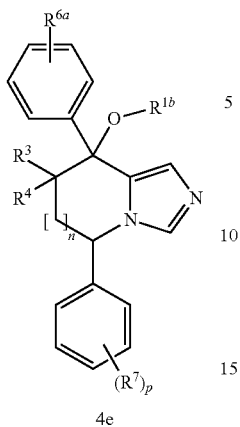

4e

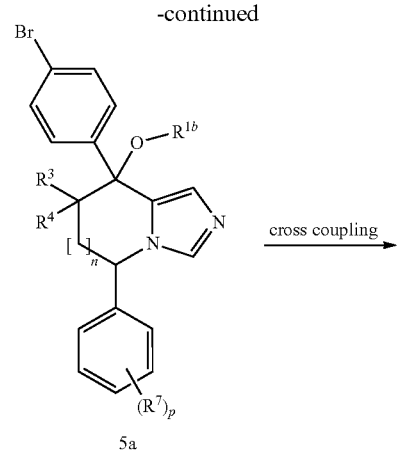

5a

Compounds of formula III, IIIA or IIIB where $R^{1b}$ is H, $R^{6a}$ is aryl or heteroaryl, optionally substituted with $R^9$ can be prepared from a 1,2 addition reaction of hydroxyl protected aryl magnesium bromide 4b (wherein P designates a protective group) to intermediate 1b or 1c in an aprotic solvent such as THF or ethyl ether. The hydroxyl protective group on intermediate 4c can be removed with a general acid such as with HCl or TFA. This resultant free alcohol 4c can be transformed into it's triflate intermediate 4d using reagents such as $Tf_2NPh$ and a suitable base such as TEA in an aprotic solvent such as THF. This aryl triflate intermediate can then used in the Stille coupling reaction using tributylstannanyl reagent in a solvent such as toluene to provide compound 4e. Alternatively, a Suzuki coupling of aryl boronic acids with the triflate intermediate 4d in the presence of a palladium catalyst such as $Pd.dppf.CH_2Cl_2$, or with the palladium tetrikis catalyst using an inorganic base such as sodium carbonate in water, DME or with EtOH can provide coupling product 4e.

Scheme 6 illustrates the synthesis of compounds of Formula I, II or III wherein one of $R^1$ and $R^2$ is OH and the other is phenyl substituted in the para position with an aryl or a heteroaryl.

Scheme 6

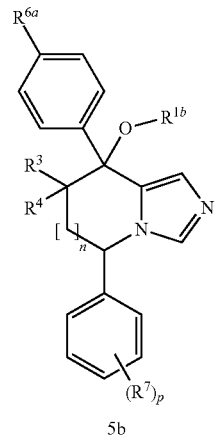

5b

The preparation of compounds of formula III, IIIA or IIIB can be achieved via a cross coupling reaction of intermediate bromide (5a). Bromide 5a can be prepared from a 1,2 addition reaction of the grignard reagent generated by the metal-halogen exchange of i-PrMgBr in THF (or in ether) with 1-bromo-4-iodobenzene, which addition generates intermediate 1b or 1c. The 1,2 addition reaction may be performed in an anhydrous solvent such as THF. Following this addition reaction, a cross coupling reaction such as a Suzuki coupling reaction with aryl boronic acids in the presence of a catalyst such as $Pd.dppf.CH_2Cl_2$, and an inorganic base such as sodium carbonate, in DME and water can provide compound 5b.

Scheme 7 illustrates the synthesis of compounds of Formula I, II or IV wherein $R^2$ is $CH_2C(O)NHR^{14}$ or $CH_2C(O)$ heterocyclyl.

Scheme 7

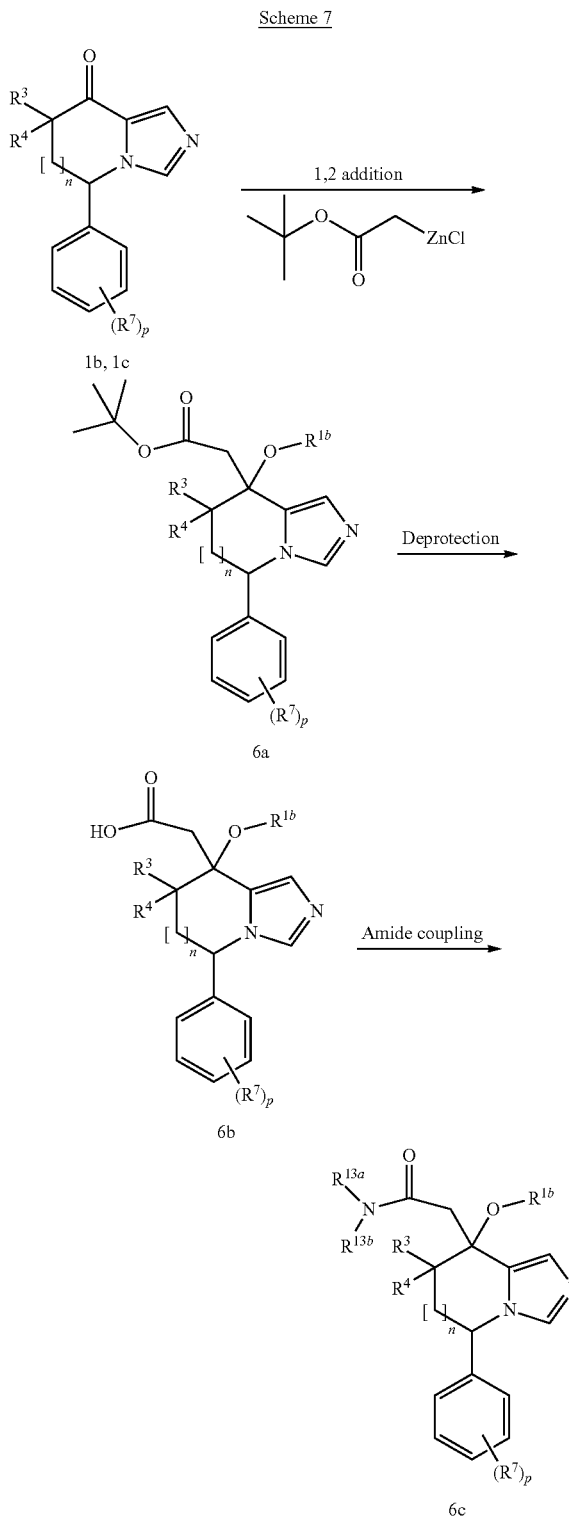

wherein $R^{13a}$ and $R^{13b}$ are H, alkyl, aryl, heteroaryl, heterocyclyl, or $R^{13a}$ and $R^{13b}$ together with the atoms to which they are attached form a 5 to 8-membered heterocyclyl. Representative examples are morpholine, piperidine, piperazine).

1,2 addition reaction of 2-tert-butyoxy-2-oxoethyl)zinc(II) chloride in a solution of THF to intermediate ketone (1b or 1c) can provide addition product 6a. The tert-butyl ester of 6a can be cleaved using a general acid such as TFA or HCl in solvents such as $CH_2Cl_2$. The resultant carboxylic acid (6b) can be subjected to amide coupling conditions using a general base such as TEA or DIPEA with amide coupling reagents such as HATU or HOAt/EDCI in solvents such as DMF and/or $CH_2Cl_2$ with a suitable amine to provide amide coupling product 6c. The amines used for the coupling reaction include but not limited to can be aryl amines, alkyl amines, heteroaryl amines, allyl amines, biaryl amines, alkyl-aryl amines. Coupling reagents used can be but are not limited to include HATU or HOAt/EDCI.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formulae I to IVB in free form or in pharmaceutically acceptable salt form, exhibit valuable pharmacological properties, e.g. aldosterone synthase and/or CYP11B1 modulating properties, e.g. as indicated in in vitro and in vivo tests as provided in the next sections and are therefore indicated for therapy.

Compounds of the invention may be useful in the treatment of an indication selected from: hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive Cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess. Thus, as a further embodiment, the present invention provides the use of a compound of formulae I-(IV) in therapy. In a further embodiment, the therapy is selected from a disease which is ameliorated by inhibiton of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

In another embodiment, the invention provides a method of treating a disease which is ameliorated by inhibiton of aldosterone synthase and/or CYP11B1 comprising administration of a therapeutically acceptable amount of a compound according to anyone of formulae I to IVB, or pharmaceutically acceptable salt thereof. In a further embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

The pharmaceutical composition or combination of the present invention can be in unit dosage of about 0.01-500 mg of active ingredient(s) for a subject of about 50-70 kg, or about 0.01-250 mg or about 0.01-150 mg or about 0.01-100 mg, or about 0.01-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.0001-500 mg/kg, or between about 0.0001-100 mg/kg, or between about 0.0003-10 mg/kg.

The activity of a compound according to the present invention can be assessed by the following in vitro & in vivo methods.

The activity of a compound according to the present invention can be assessed by the in vitro methods described below, and/or by the following in vitro & in vivo methods well-described in the art. See Fieber, A et al. (2005), "Aldosterone Synthase Inhibitor Ameliorates Angiotensin II-Induced Organ Damage," *Circulation*, 111:3087-3094.

In particular, the aldosterone synthase inhibitory activities in vitro can be determined by the following assay.

Human adrenocortical carcinoma NCI-H295R cell line was obtained from American Type Culture Collection (Manassas, Va.). Insulin/transferrin/selenium (ITS)-A supplement (100×), DMEM/F-12, antibiotic/antimycotic (100×), and fetal bovine serum (FBS) were purchased from Invitrogen (Carlsbad, Calif.). Anti-mouse PVT scintillation proximity assay (SPA) beads and NBS 96-well plates were obtained from GE Health Sciences (Piscataway, N.J.) and Corning (Acton, Mass.), respectively. Solid black 96-well flat bottom plates were purchased from Costar (Corning, N.Y.). Aldosterone and angiotensin (Ang II) were purchased from Sigma (St. Louis, Mo.). D[1,2,6,7-$^3$H(N)]aldosterone was acquired from PerkinElmer (Boston, Mass.). Nu-serum was a product of BD Biosciences (Franklin Lakes, N.J.).

For in vitro measurement of aldosterone activity, human adrenocortical carcinoma NCI-H295R cells are seeded in NBS 96-well plates at a density of 25,000 cells/well in 100 µl of a growth medium containing DMEM/F12 supplemented with 10% FCS, 2.5% Nu-serum, 1 µg ITS/ml, and 1× antibiotic/antimycotic. The medium is changed after culturing for 3 days at 37° C. under an atmosphere of 5% $CO_2$/95% air. On the following day, cells are rinsed with 100 µl of phosphate-buffered saline (PBS) and incubated with 100 µl of treatment medium containing 1 µM Ang II and a compound at different concentrations in quadruplicate wells at 37° C. for 24 hr. At the end of incubation, 50 µl of medium is withdrawn from each well for measurement of aldosterone production by an SPA using mouse anti-aldosterone monoclonal antibodies.

Measurement of aldosterone activity can also be performed using a 96-well plate format. Each test sample is incubated with 0.02 µCi of D[1,2,6,7-$^3$H(N)]aldosterone and 0.3 µg of anti-aldosterone antibody in PBS containing 0.1% Triton X-100, 0.1% bovine serum albumin, and 12% glycerol in a total volume of 200 µl at room temperature for 1 hr. Anti-mouse PVT SPA beads (50 µl) are then added to each well and incubated overnight at room temperature prior to counting in a Microbeta plate counter. The amount of aldosterone in each sample is calculated by comparing with a standard curve generated using known quantities of the hormone.

The in vitro inhibitory activities for CYP11B1 can be determined by the following assay.

The cell line NCI-H295R was originally isolated from an adrenocortical carcinoma and has been characterized in the literature through the stimulable secretion of steroid hormones and the presence of the enymes essential for steroidogenesis. Thus, the NCI-H295R cells have CYP11 B1 (steroid 11 β-hydroxylase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbeoco's Modified Eagle'Ham F-12 Medium (DME/F12), which has been supplemented with Ulroser SF Serum (Soprachem, Cergy-Saint-Christophe, France), insulin, transferrin, selenite (I-T-S, Becton Dickinson Biosiences, Franklin lakes, NJ, USA) and antibiotics in 75 cm$^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin 11 (1 D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturer's instructions.

Inhibition of the release of certain steroids can be used as a measure of the respective enzyme inhibition by the added test compounds. The dose-dependent inhibition of enzymic activity by a compound is calculated by means of an inhibition plot which is characterized by an IC50.

The IC50 values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows:

Y=(d−a)/((1+(x/c)b))+a, where: a=minimum data level, b=gradient, I c=IC50, d=maximum data level, x=inhibitor concentration.

The inhibition activity of aldosterone production can also be expressed in percentage inhibition (% inhibition) at a given concentration (e.g. % inhibition at 1 µM), which is the aldosterone level when the cell is treated with the given concentration of a compound of this invention (e.g. concentration of 1 µM) versus the aldosterone excretion when cell is free of the compound of the invention:

% inhibition aldosterone production=[(Y−X)/Y]×100 wherein X is the level of aldosterone when the cell is treated with a compound according to anyone of Formulae I to IVB; or pharmaceutically acceptable salt thereof, and Y is the level of aldosterone when the cell is free of compound according to anyone of Formulae I to IVB, or pharmaceutically acceptable salt thereof.

The inhibition activity of CYP11B1 production can also be expressed in percentage inhibition (% inhibition) at a given concentration (e.g. % inhibition at 1 µM), which is the cortisol level when cell is treated with the given concentration of a compound of the invention (e.g. concentration of 1 µM) versus the cortisol excretion when cell is free of the compound of the invention.

% inhibition cortisol production=[(Y'−X')/Y']×100 wherein X' is the level of cortisol when the cell is treated with a compound of Formulae I to IVB; and Y' is the level of cortisol when the cell is free of compound of Formulae I to IVB.

Using the test assays for measuring CYP11B1 (cortisol) and CYP11B2 (aldosterone), as described above, compounds of the invention exhibited inhibitory efficacy as shown in Table 1, provided infra.

TABLE 1

Inhibitory Activity of Compounds

| Examples | cellular aldosterone IC$_{50}$ (nM) | cellular cortisol IC$_{50}$ (nM) |
| --- | --- | --- |
| 1-1 | 11 | 472 |
| 1-2 | 27 | 84 |
| 1-4 | 5 | 480 |
| 1-12 | 2 | 6 |
| 1-13 | 34 | 103 |
| 1-16 | 2 | 143 |
| 1-17 | 1 | 14 |
| 1-30 | 25 | 522 |
| 1-32 | 6 | 645 |
| 1-41 | 72 | 135 |
| 1-50 | 7 | 1795 |
| 1-52 | 142 | 273 |
| 1-53 | 42 | 220 |
| 2-10 | 6 | 338 |
| 3-14 | 64 | 10170 |
| 4-15 | 72 | 8780 |

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound according to anyone of formulae I to IVB or a pharmaceutically acceptable salt thereof, and at least one other therapeutic agent as a combined preparation for simultaneous, separate or sequential use in therapy. In one embodiment, the therapy is the treatment of a disease or condition mediated by aldosterone synthase and/or CYP11B1. Products provided as a combined preparation include a composition comprising the compound according to anyone of formulae I to IVB, or a pharmaceutically acceptable salt thereof, and the other therapeutic agent(s) together in the same pharmaceutical composition, or the compound according to anyone of formulae I to IVB, or a pharmaceutically acceptable salt thereof, and the other therapeutic agent(s) in separate form, e.g. in the form of a kit.

In one embodiment, the invention provides a pharmaceutical composition comprising a compound according to anyone of formulae I to IVB and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of formulae I to IVB, or pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides the use of a compound according to anyone of formulae I to IVB, or pharmaceutically acceptable salt thereof, for treating a disease or condition mediated by aldosterone synthase and/or CYP11B1, wherein the medicament is prepared for administration with another therapeutic agent. The invention also provides the use of another therapeutic agent for treating a disease or condition mediated by aldosterone synthase and/or CYP11B1, wherein the medicament is administered with a compound according to anyone of formulae I to IVB, or pharmaceutically acceptable salt thereof.

The invention also provides a compound according to anyone of formulae I to IVB, or pharmaceutically acceptable salt thereof, for use in a method of treating a disease or condition mediated by aldosterone synthase and/or CYP11B1, wherein the compound according to anyone of formulae I to IVB, or pharmaceutically acceptable salt thereof, is prepared for administration with another therapeutic agent. The invention also provides another therapeutic agent for use in a method of treating a disease or condition mediated by aldosterone synthase and/or CYP11B1, wherein the other therapeutic agent is prepared for administration with a compound according to anyone of formulae I to IVB, or pharmaceutically acceptable salt thereof. The invention also provides a compound according to anyone of formulae I to IVB, or pharmaceutically acceptable salt thereof, for use in a method of treating a disease or condition mediated by aldosterone synthase and/or CYP11B1, wherein the compound according to anyone of formulae I to IVB, or pharmaceutically acceptable salt thereof, is administered with another therapeutic agent. The invention also provides another therapeutic agent for use in a method of treating a disease or condition mediated by aldosterone synthase and/or CYP11B1, wherein the other therapeutic agent is administered with a compound according to anyone of formulae I to IVB, or pharmaceutically acceptable salt thereof.

The invention also provides the use of a compound according to anyone of formulae I to IVB, or pharmaceutically acceptable salt thereof, for treating a disease or condition mediated by aldosterone synthase and/or CYP11B1, wherein the patient has previously (e.g. within 24 hours) been treated with another therapeutic agent. The invention also provides the use of another therapeutic agent for treating a disease or condition mediated by aldosterone synthase and/or CYP11B1, wherein the patient has previously (e.g. within 24 hours) been treated with a compound according to anyone of formulae I to IVB, or pharmaceutically acceptable salt thereof.

In one embodiment, the other therapeutic agent is selected from: HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blacker, or a CETP inhibitor.

In still another embodiment, the invention pertains, at least in part, to methods wherein the compound of the invention (e.g., a compound according to anyone of Formulae I to IVB or a compound otherwise described herein) is administered in combination with a second agent.

The term "in combination with" a second agent or treatment includes co-administration of the compound of the invention (e.g., a compound according to anyone of Formulae I to IVB or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g., an aldosterone synthase associated disorder, such as, for example, hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries. Furthermore, the second agent may be any agent of benefit to the patient when administered in combination with the administration of a compound of the invention.

Examples of second agents include HMG-Co-A reductase inhibitors, angiotensin II receptor antagonists, angiotensin converting enzyme (ACE) Inhibitors, calcium channel blockers (CCB), dual angiotensin converting enzyme/neutral endopeptidase (ACE/NEP) inhibitors, endothelin antagonists, renin inhibitors, diuretics, ApoA-I mimics, anti-diabetic agents, obesity-reducing agents, aldosterone receptor blockers, endothelin receptor blockers, and CETP inhibitors.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

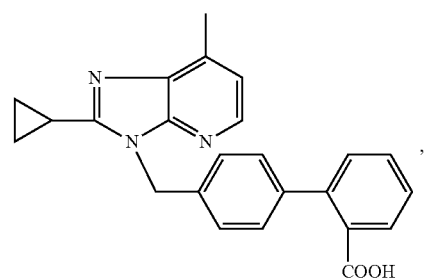 [SMILES: Cc1ccnc2c1nc(C1CC1)n2Cc1ccc(-c2ccccc2C(=O)O)cc1]

the compound with the designation SC-52458 of the following formula

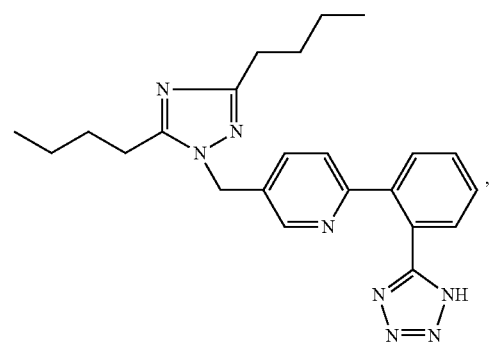 [SMILES: CCCCc1nc(CCCC)n(Cc2ccc(-c3ccccc3-c3nnn[nH]3)nc2)n1]

and the compound with the designation ZD-8731 of the following formula

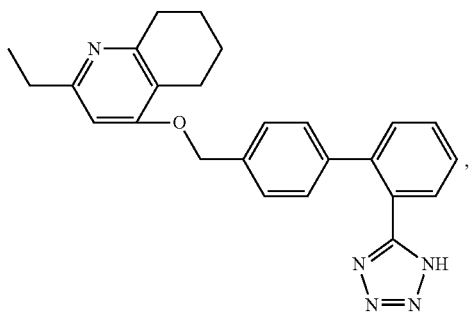 [SMILES: CCc1cc(OCc2ccc(-c3ccccc3-c3nnn[nH]3)cc2)c2c(n1)CCCC2]

or, in each case, a pharmaceutically acceptable salt thereof.

Preferred AT$_1$-receptor antagonist are those agents which have been marketed, most preferred is valsartan or a pharmaceutically acceptable salt thereof.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enalprilat, fosinopril, imidapril, lisinopril, moveltopril, perindopril, quinapril, ramipril, spirapril, temocapril, and trandolapril, or, pharmaceutically acceptables salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "dual angiotensin converting enzyme/neutral endopetidase (ACE/NEP) inhibitor" includes omapatrilate (cf. EP 629627), fasidotril or fasidotrilate, or pharmaceutically acceptable salts thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

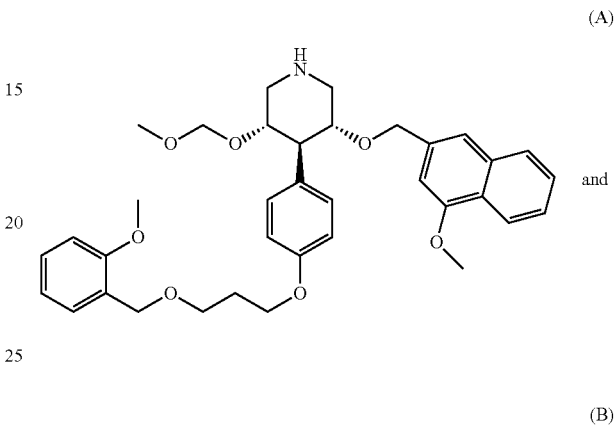

and

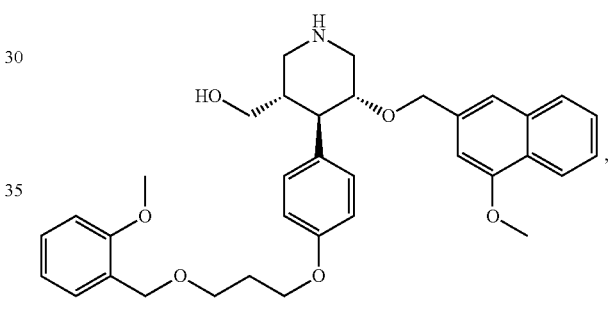

or,
pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

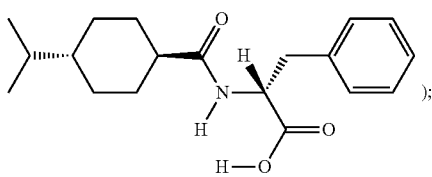 [SMILES: CC(C)[C@H]1CC[C@H](C(=O)N[C@H](Cc2ccccc2)C(=O)O)CC1]
);

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia*, 28, 1985, 704-707 and in U.S. Pat. No. 5,705,483.

The term "GLP-1 agonists" includes variants and analogs of GLP-1(7-36)$NH_2$ which are disclosed in particular in U.S. Pat. Nos. 5,120,712, 5,118,666, 5,512,549, WO 91/11457 and by C. Orskov et al in J. Biol. Chem. 264 (1989) 12826. Further examples include GLP-1(7-37), in which compound the carboxy-terminal amide functionality of $Arg^{36}$ is displaced with Gly at the $37^{th}$ position of the GLP-1(7-36)$NH_2$ molecule and variants and analogs thereof including $GLN^9$-GLP-1(7-37), D-$GLN^9$-GLP-1(7-37), acetyl $LYS^9$-GLP-1(7-37), $LYS^{18}$-GLP-1(7-37) and, in particular, GLP-1(7-37) OH, $VAL^8$-GLP-1(7-37), $GLY^8$-GLP-1(7-37), $THR^8$-GLP-1(7-37), $MET^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl])-2-propynyl]-5-phenylsulfonyl)thiazolidine-2,4-dione, 5-[(3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; $a_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

The term "aldosterone receptor blocker" includes spironolactone and eplerenone.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

In one embodiment, the invention provides a pharmaceutical composition comprising a therapeutically effective amount of a compound according to anyone of formulae I to IVB or a pharmaceutically acceptable salt thereof, and one or more pharmaceutically acceptable carriers.

In one embodiment, the invention provides a combination, in particular a pharmaceutical combination, comprising a therapeutically effective amount of the compound according to anyone of formulae I to IVB or a pharmaceutically acceptable salt thereof and one or more therapeutically active agents selected from HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

In one embodiment, the invention provides a method of modulating aldosterone synthase and/or CYP11B1 activity in a subject, wherein the method comprises administering to the subject a therapeutically effective amount of the compound according to anyone of formulae I to IVB, or a pharmaceutically acceptable salt thereof.

In one embodiment, the invention provides a method of treating a disorder or a disease in a subject mediated by aldosterone synthase and/or CYP11B1 wherein the method comprises administering to the subject a therapeutically effective amount of the compound according to anyone of formulae I to IVB, or a pharmaceutically acceptable salt thereof.

In one embodiment, the invention provides a method of treating a disorder or a disease in a subject mediated by aldosterone synthase and/or CYP11B1, wherein the disorder or the disease is selected from hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive Cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess.

Thus, as a further embodiment, the present invention provides the use of a compound according to anyone of formulae I to IVB, or pharmaceutically acceptable salt thereof, in therapy. In a further embodiment, the therapy is selected from a disease which is ameliorated by inhibiton of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

In one embodiment, the invention provides a compound according to the definition of formulae I to IVB, for use as a medicament.

In one embodiment, the invention provides the use of a compound according to the definition of formulae I to IVB, for the treatment of a disorder or disease in a subject mediated by aldosterone synthase and/or CYP11B1.

In one embodiment, the invention provides the use of a compound according to the definition of formulae I to IVB, in the manufacture of a medicament for the treatment of a disorder or disease in a subject characterized by an activity of aldosterone synthase and/or CYP11B1, wherein said disorder or disease is in particular selected from hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive Cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess.

Thus, as a further embodiment, the present invention provides the use of a compound according to anyone of formulae I to IVB, or pharmaceutically acceptable salt thereof, in therapy. In a further embodiment, the therapy is selected from a disease which is ameliorated by inhibiton of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

EXEMPLIFICATION OF THE INVENTION

Common Abbreviations

Abbreviations
Ac: Acetyl
Atm: atmosphere
Aq: aqueous
br: broad
Bn: benzyl
Boc: tert-butoxycarbonyl
d, dd: doublet, doublet of doublets
DAD: diode array detector
DAST: (diethylamino)sulfur trifluoride
DCE: dichloroethane
DCM: dichloromethane
DIPEA: N,N-diisopropylethylamine
DMAP: N,N-dimethylaminopyridine
DMF: N,N-dimethylformamide
DMSO: dimethyl sulfoxide
Dppf: 1,1'-bis(diphenylphosphino)ferrocene
EDCI: N-Ethyl-N'-(3-dimethylaminopropyl)carbodiimide hydrochloride
Et: ethyl
EtOH: ethyl alcohol
EtOAc: ethyl acetate
HATU: O-(7-azobenzotriazol-1-yl)-1,1,3,3-tetramethyluroniumhexafluorophosphate
Hr(s): hour(s)
HCl: hydrogen chloride
HPLC: high pressure liquid chromatography
HOAt: 1-hydroxy-7-azabezotriazole
iPr: isopropyl
iPrMgBr: isopropyl magnesium bromide
IR: infrared
L: liter
LC: liquid chromatography
LCMS: liquid chromatography mass spec
LCMS-RT: liquid chromatography mass spec retention time
LDA: lithium diisopropylamide
m: multiplet
M: molar
Me: methyl
MeOH: methyl alcohol
MeCN: acetonitrile
mg: milligram
min: minute(s)
mmol: millimole(s)
mol: mole(s)
MS: mass spectrometry
Ms: mesyl
NMR: nuclear magnetic resonance
Pd: palladium
Pd/C: palladium on carbon
Ph: phenyl
ppm: parts per million
PS: polymer supported
$Rh_2(cap_4)$: rhodium(II) caprolactone dimer
RP: reversed phase
RPHPLC: reversed phase high pressure liquid chromatography
s: singlet
s-BuLi: sec-butyllithium
sat: saturate
t: triplet
t-BuLi: tert-butyllithium
Tf: trifluoromethane sulfonate
TFA: trifluoroacetic acid
THF: tetrahydrofuran
THP: tetrahydropyranyl
TLC: thin layer chromatography
tBu: tert-butyl
tBu: tert-butyl hydrogen peroxide
μL, mL and L: microliter, milliliter and liter
UV: ultraviolet

EXAMPLES

The following examples are intended to illustrate the invention and are not to be construed as being limitations thereon. Temperatures are given in degrees centigrade. If not mentioned otherwise, all evaporations and concentrations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The conditions for measuring the retention times are as follows:

Analytical LCMS Condition A:
Column: INERTSIL C8-3, 3 cm×33 mm×3.0 μm; Flow rate: 2 mL/min; Mobile phase: MeCN (5 mM $NH_4$+HCOO−)/water; Gradient: linear gradient from 10 to 90% MeCN in 2 min; Detection: DAD-UV at 200-400 nm Analytical LCMS Condition B:
Column: INERTSIL C18, 3 cm×33 mm×3.0 μm; Flow rate: 2 mL/min; Mobile phase: MeCN (5 mM $NH_4$+HCOO−)/water; Gradient: linear gradient from 25 to 90% MeCN in 2 min; Detection: DAD-UV at 200-400 nm.

Analytical LCMS Condition C:
Waters Acquity UPLC, run time: 6.00 min, Acquity Column 2.1×50 mm HSS T3 1.8μ. Solvent A: water+3 mM ammonium acetate+0.05% formic acid (from 98% to 2%), Solvent B: acetonitrile+0.04% formic acid (from 2% to 98%). Detection: DAD-UV at 200-400 nm.

Analytical LCMS Condition D:
Waters XBridge C18 column 3 cm×30 mm, 2.5 μm, run time: 3 min, Solvent A: water+5% MeCN+0.5%-1% formic acid (from 99% to 5%), Solvent B: MeCN+0.5%-1% formic acid (from 1% to 95%). Detection: DAD-UV at 200-400 nm.

Analytical LCMS Condition E:
Column: INERTSIL C18, 3 cm×33 mm×3.0 μm; Flow rate: 2 mL 1 min; 0.1% formic acid/water; Gradient: linear gradient from 2 to 90% MeCN in 2 min; Detection: DAD-UV at 200-400 nm.

The relative stereochemistry was determined using Nuclear Overhauser Effect (NOE) experiment. Under the reaction conditions, racemization of the stereocenter bearing the 2-fluoro-4-cyano-phenyl group is not expected. Therefore, the absolute stereochemistry can be assigned based on the relative stereochemistry and the stereochemistry of the center bearing the 2-fluoro-4-cyano-phenyl group.

The stereochemistry of each enantiomer was also verified using the following experiment: 1,2 addition of (4-bromophenyl)magnesium iodide into racemic 4-(6,7-dihydro-5H-pyrrolo[1,2-c]imidazol-5-yl)-3-fluorobenzonitrile provided mixtures of all four possible 1,2-addition stereoisomers.

Each stereoisomer were characterized by 1H NMR and matched to the isolated major and minor diastereomers obtained from the 1,2 addition reaction using the chirally pure intermediate 1-1a as well as to the major and minor diastereomers obtained from the 1,2 addition reaction using chirally pure intermediate 1-1b (which is the enantiomer of 1-1a).

Intermediate 1-1a: 3-fluoro-4-((R)-7-oxo-6,7-dihydro-5H-pyrrolo[1,2-c]imidazol-5-yl)-benzonitrile

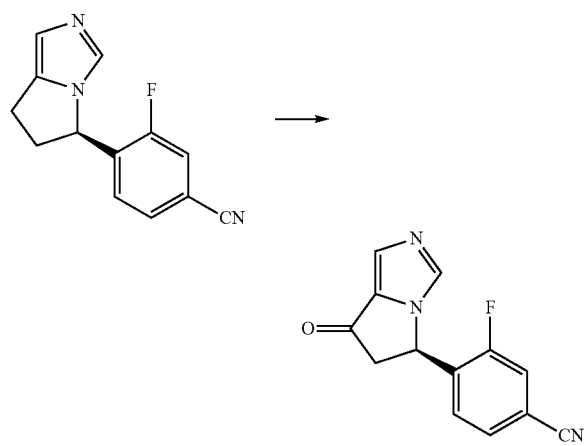

For the preparation of 4-(R)-6,7-dihydro-5H-pyrrolo[1,2-c]imidazol-5-yl-3-fluoro-benzonitrile: see WO 2007024945, CAS #928134-65-0.

In a 500 mL round-bottomed flask equipped with water condenser was added 4-(R)-6,7-dihydro-5H-pyrrolo[1,2-c]imidazol-5-yl-3-fluoro-benzonitrile. To this crude was added pyridine (48.5 ml) followed by iron(III) chloride (0.32 g, 1.96 mmol). To this crude was added tert-butyl hydroperoxide (16.3 mL, 117 mmol). The crude was refluxed and stirred for 5 hrs. The crude was cooled to room temperature and filtered through sand, celite, and the filtrate was concentrated. The residue was purified via column chromatography using CH$_2$Cl$_2$ to 10% (2M NH$_3$ in MeOH)/CH$_2$Cl$_2$ to give 2.44 g of the entitled product. MS 242.1 (M+1); LCMS condition B, retention time 1.04 min. 1H NMR (400 MHz, CDCl$_3$) δ ppm 3.09 (dd, 1H), 3.78 (dd, 1H), 6.00 (dd, 1H), 7.08 (t, 1H), 7.43-7.56 (m, 2H), 7.63 (s, 1H), 7.71 (s, 1H).

Intermediate 1-b: 3-fluoro-4-((S)-7-oxo-6,7-dihydro-5H-pyrrolo[1,2-c]imidazol-5-yl)-benzonitrile

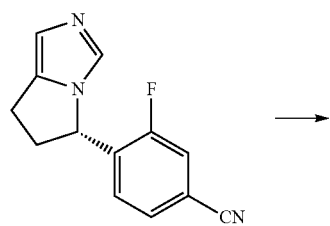

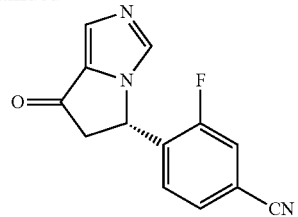

For the preparation of 4-(S)-6,7-dihydro-5H-pyrrolo[1,2-c]imidazol-5-yl-3-fluoro-benzonitrile: see WO 2007024945, CAS #928134-66-1.

To a 500 mL round-bottomed flask equipped with a water condensor is added (S)-4-(6,7-dihydro-5H-pyrrolo[1,2-c]imidazol-5-yl)-3-fluorobenzonitrile (6.0 g, 26.3 mmol) and pyridine (32.6 mL). To the solution is added iron(III) chloride (0.21 g, 1.32 mmol and tert-butyl hydroperoxide (10.9 mL, 79 mmol). The reaction is heated to reflux and stirred for 5 hours. The reaction is allowed to cool to room temperature and is then filtered through celite. The collect filtrate is concentrated under reduced pressure. The obtained residue is purified by RP-HPLC (XBridge, C8 H$_2$O (0.1% NH$_4$OH)/CH$_3$CN) to give 1.5 g of the entitled product. MS (m+1)=242.1; LCMS condition B, retention time=0.97 min; 1H NMR (400 MHz, CDCl$_3$) δ ppm 3.12 (dd, 1H), 3.80 (dd, 1H), 6.04 (dd, 1H), 7.14 (t, 1H), 7.48-7.57 (m, 2H), 7.61 s, 1H, 7.72 s, 1H.

Intermediate 1-1c: (R)-4-(8-oxo-5,6,7,8-tetrahydroimidazo[1,5-a]pyridin-5-yl)benzonitrile

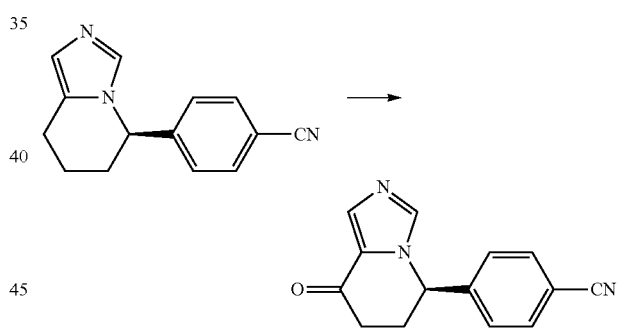

For the preparation of 4-(R)-6,7-dihydro-5H-pyrrolo[1,2-c]imidazol-5-yl-3-fluoro-benzonitrile HCl salt: see Menard, J.; Gonzalez, M-F.; Guyene, T-T.; Bissery, A.; Journal of Hypertension, 2006, 24, 1147-1155.

To a round bottom flask was added Rh$_2$(cap)$_4$ (80 mg, 0.09 mmol), NaHCO$_3$ (38 mg, 0.45 mmol) and (R)-4-(5,6,7,8-tetrahydroimidazo[1,5-a]pyridin-5-yl)benzonitrile, CAS #102676-87-9, (200 mg, 0.99 mmol). To this crude was added DCE (10 mL). To this crude was added anhydrous tert-butyl hydroperoxide (1.5 mL, 9.0 mmol). The crude was stirred at 40° C. for overnight. The crude was cooled to room temperature and filtered through celite, and the filtrate was concentrated. The residue was purified via column chromatography using a gradient, CH$_2$Cl$_2$ to 10% (2M NH$_3$ in MeOH)/CH$_2$Cl$_2$ to give 0.12 g of the entitled product. MS 238.0 (M+H), LCMS condition B, retention time 0.50 min. 1H NMR (400 MHz, CDCl$_3$) δ ppm 2.23-2.51 (m, 2H), 2.51-2.65 (m, 2H), 5.40-5.57 (m, 1H), 7.13 (d, 2H), 7.35 (s, 1H), 7.65 (d, 2H), 7.88 (s, 1H).

General condition A for 1,2 Addition

Example 1-1

3-fluoro-4-((5R,7S)-7-hydroxy-7-vinyl-6,7-dihydro-5H-pyrrolo[1,2-c]imidazol-5-yl)benzonitrile

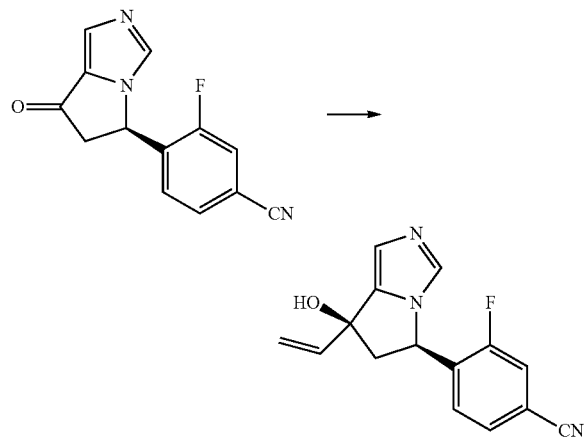

To a stirred solution of 3-fluoro-4-((R)-7-oxo-6,7-dihydro-5H-pyrrolo[1,2-c]imidazol-5-yl)-benzonitrile (0.6 g, 2.5 mmol), in THF (20 mL) cooled in a dry ice acetone bath under nitrogen was added via syringe a solution of vinyl magnesium bromide (0.7 M) in THF (4.3 mL, 3.0 mmol). The crude was warmed to room temperature in 3 hrs. The crude was quenched with NH$_4$Cl aq. The crude was diluted in EtOAc. The organic layer was dried over MgSO$_4$, filtered, and concentrated. The crude was purified via preparation plate using 5% (2M NH$_3$ in MeOH)/CH$_2$Cl$_2$ two times followed by purification using RPHPLC using 10% to 40% MeCN/H$_2$O to give 142 mg of the entitled product as the major diastereomer. MS 270.2 (M+H); LCMS condition A, retention time 0.99 min. 1H NMR (400 MHz, CDCl$_3$-d) ppm 2.56 (br. s., 1H), 2.68 (dd, 1H), 3.22 (dd, 1H), 5.24 (d, 1H), 5.41 (d, 1H), 5.59-5.73 (m, 1H), 6.10 (dd, 1H), 6.91 (br. s., 1H), 7.10 (t, 1H), 7.35 (d, 2H), 7.39 (br. s., 1H).

General Condition B for 1,2 Addition

Example 1-2

4-((5R,7S)-7-(3-cyclopropylphenyl)-7-hydroxy-6,7-dihydro-5H-pyrrolo[1,2-c]imidazol-5-yl)-3-fluorobenzonitrile

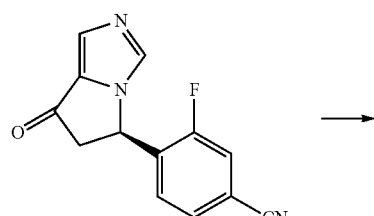

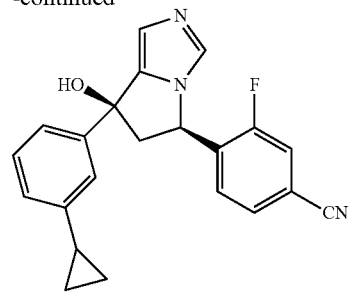

To a solution of 1-bromo-3-cyclopropyl-benzene (0.018 ml, 0.124 mmol) in THF (0.2 ml) cooled to −78° C. was added a solution of 1.6 M t-BuLi (0.155 ml, 0.249 mmol). The crude was stirred at −78° C. for 2 hrs. To this solution was add a solution of 3-fluoro-4-((R)-7-oxo-6,7-dihydro-5H pyrrolo[1,2-c]imidazol-5-yl)-benzonitrile (20 mg, 0.083 mmol) in THF (0.2 ml). The crude was stirred at −78° C. for 1 hr, then at 0° C. for 1 hr and room temperature for 1 hr. This reaction was quenched with water and extract the aq. with CH$_2$Cl$_2$. The organic layer was dried over Na$_2$SO$_4$, filtered, and concentrated. The crude was purified via preparation plate using 10% (2M NH$_3$ in MeOH)/CH$_2$Cl$_2$. The entitled product (4 mg) was isolated as the major diastereomer. MS 360.1 (M+H); LCMS condition B, retention time 1.16 min. $^1$H NMR (400 MHz, CDCl$_3$) δ ppm 0.52-0.65 (m, 2H), 0.85-0.95 (m, 2H), 1.74-1.91 (m, 1H), 2.57 (br. s., 1H), 2.92 (d, 1H), 3.30 (dd, 1H), 5.73 (d, 1H), 6.91 (s, 1H), 6.96 (ddd, 1H), 7.12 (t, 1H), 7.16-7.28 (m, 3H), 7.29-7.41 (m, 2H), 7.42-7.53 (m, 1H).

General Condition C for 1,2 Addition

Example 1:3

4-((5R,7S)-7-(4-(1,1-difluoroethyl)phenyl)-7-hydroxy-6,7-dihydro-5H-pyrrolo[1,2-c]imidazol-5-yl)-3-fluorobenzonitrile

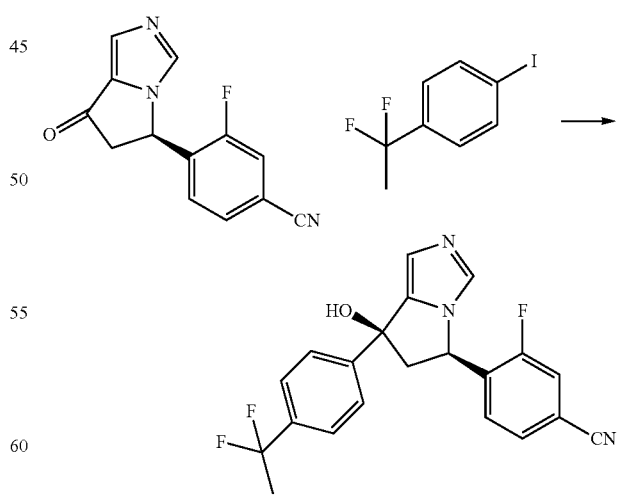

To a solution of 1-(1,1-difluoro-ethyl)-4-iodo-benzene, (167 mg, 0.62 mmol) in THF (2 mL) cooled to −40° C. was added a 2 M solution of i-PrMgCl in THF (0.42 mL, 0.83 mmol) dropwise. The crude was stirred at −40° C. for 1 hr.

3-fluoro-4-((R)-7-oxo-6,7-dihydro-5H-pyrrolo[1,2-c]imidazol-5-yl)-benzonitrile (125 mg, 0.52 mmol) in THF (2 mL) was added. The crude was allowed to slowly warm to room temperature over 3 hrs. The crude was quenched with NH₄Cl aq. The crude diluted in EtOAc. The organic layer was washed with brine, dried over MgSO₄, filtered, and concentrated. The crude was purified via preparation plate two times using 2M NH₃ in MeOH/CH₂Cl₂ to give 37 mgs of the entitled product. MS 384.3 (M+H); LCMS condition A, retention time 1.31 min. 1H NMR (400 MHz, CDCl₃) δ ppm 1.83 (t, 3H), 2.94 (dd, 1H), 3.24 (dd, 1H), 5.70 (d, 1H), 6.47 (s, 1H), 7.11 (t, 1H), 7.19 (s, 1H), 7.33 (d, 2H), 7.38 (m, 2H), 7.46 (m, 2H).

Intermediate 1-3a:
1-(1,1-Difluoro-ethyl)-4-iodo-benzene

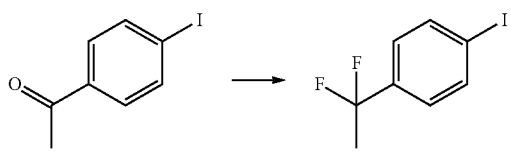

To a solution of 1-(4-Iodo-phenyl)-ethanone (2 g, 8.13 mmol) in CH₂Cl₂ (3 ml) in a microwave vial with stirbar was added bis(2-methoxyethyl)aminosulfur trifluoride (1.98 g, 8.94 mmol) at room temperature. 0.1 ml of EtOH was added to the reaction mixture and the reaction was stirred sealed at 85° C. for overnight. This solution was slowly poured into sat NaHCO₃ (10%)/CH₂Cl₂ cooled in an icebath. The crude was extracted with CH₂Cl₂ 3×. The combined organic layers were dried over MgSO₄, filtered, and concentrated. The crude was purified via column chromatography using heptane to 10% EtOAc/heptane to give the entitled product. 1H NMR (400 MHz, CDCl₃) δ ppm 1.82 (t, 3H), 7.17 (m, 2H), 7.69 (m, 2H).

General Condition D for 1,2 Addition

Example 1-4

4-((5R,7S)-7-(3,4-dimethylphenyl)-7-hydroxy-6,7-dihydro-5H-pyrrolo[1,2-c]imidazol-5-yl)-3-fluorobenzonitrile

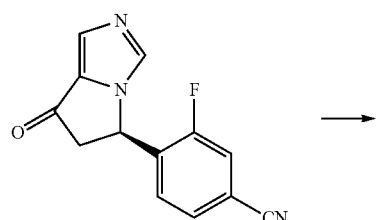

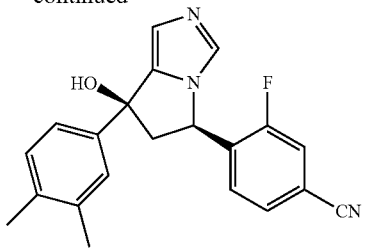

To a solution of 4-bromo-1,2-dimethylbenzene (77 mg, 0.42 mmol) in THF (1 mL) at −78° C. was added a solution of 1.4 M s-BuLi in cyclohexane (0.33 ml, 0.46 mmol). The crude was warmed to −40° C. and stirred between −40° C. and −30° C. for 1 hr. The crude was cooled to −60° C. A solution of 3-fluoro-4-((R)-7-oxo-6,7-dihydro-5H-pyrrolo[1,2-c]imidazol-5-yl)-benzonitrile (50 mg, 0.21 mmol) in THF (1 mL) was added. The crude was stirred at −60° C. for 1 hr. The crude was warmed to room temperature in 4 hrs. The crude was quenched with NH₄Cl and diluted with EtOAc. The organic layer was washed with brine, dried over MgSO₄, filtered, and concentrated. The crude was purified via preparation plate using 7% (2M NH₃ in MeOH)/CH₂Cl₂ to give 7.8 mg of the entitled product as the major diastereomer. MS 348.1 (M+H); LCMS condition A, retention time 1.31 min. 1H NMR (400 MHz, CDCl₃) δ ppm 2.20 (s, 3H), 2.20 (s, 3H), 2.91 (dd, 1H), 3.29 (dd, 1H), 5.71 (d, 1H), 6.87 (s, 1H), 7.07 (d, 1H), 7.10-7.20 (m, 2H), 7.21 (s, 1H), 7.34 (d, 1H), 7.36 (s, 1H), 7.39-7.43 (m, 1H).

General Condition E for 1,2 Addition

Example 1-5

3-fluoro-4-((5R,7S)-7-hydroxy-7-(4-(trifluoromethoxy)phenyl)-6,7-dihydro-5H-pyrrolo[1,2-c]imidazol-5-yl)benzonitrile

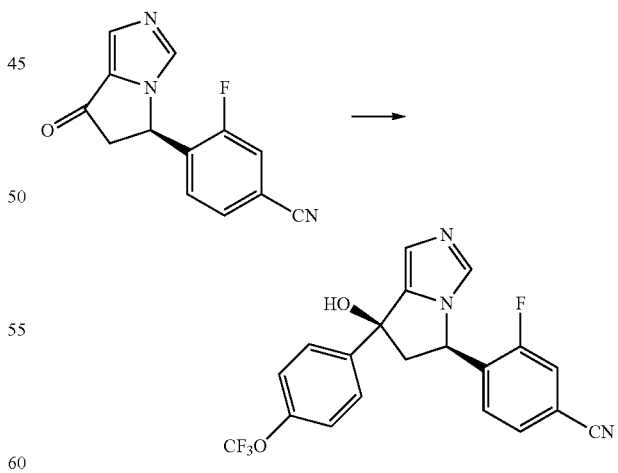

To a solution of a 1.6 M n-BuLi solution in hexane (0.428 ml, 0.684 mmol) cooled in a dry ice and acetone bath was added a solution of 1-bromo-4-(trifluoromethoxy)benzene (0.046 ml, 0.311 mmol) in 1 mL THF. The yellow crude was stirred at −78° C. for 1 hr. This crude was cannulated to a solution of 3-fluoro-4-((R)-7-oxo-6,7-dihydro-5H-pyrrolo

[1,2-c]imidazol-5-yl)-benzonitrile (75 mg, 0.311 mmol) in THF (1 mL) cooled to −78° C. The crude was slowly warmed to room temperature over 5 hrs. The crude was quenched with NH$_4$Cl and diluted with EtOAc. The organic layer was washed with brine, dried over MgSO$_4$, filtered, and concentrated. The crude was first purified via preparation plate using 5% (2M NH$_3$ in MeOH)/CH$_2$Cl$_2$. The product was further purified using HPLC to give 19.8 mg of the entitled product as the major diastereomer. MS 404.2 (M+H); LCMS condition A, retention time 1.38 min. $^1$H NMR (400 MHz, CDCl$_3$) δ ppm 2.94 (d, 1H), 3.26 (dd, 1H), 5.71 (d, 1H), 6.72 (br. s., 1H), 7.03-7.17 (m, 3H), 7.27-7.39 (m, 3H), 7.40-7.52 (m, 2H).

General Condition F for 1,2 Addition

Example 1-6

4-((5R,7R)-7-(benzo[d]thiazol-2-yl)-7-hydroxy-6,7-dihydro-5H-pyrrolo[1,2-c]imidazol-5-yl)-3-fluorobenzonitrile

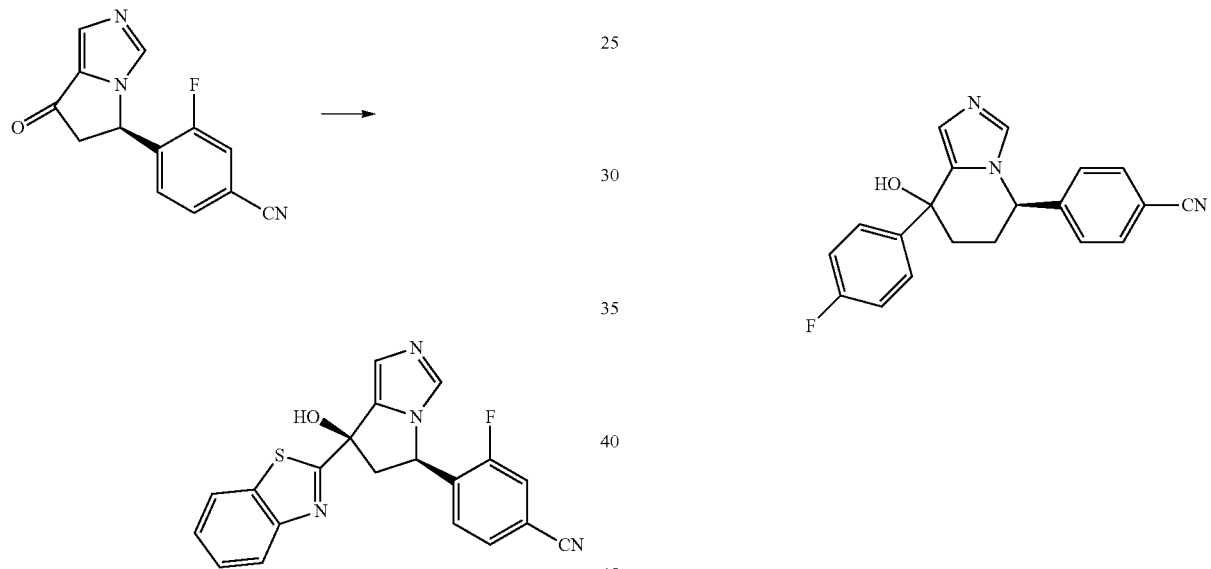

To a 1.6 M solution of n-BuLi in hexane (0.29 mL, 0.46 mmol) cooled to −78° C. was added a solution of benzo[d]thiazole (56 mg, 0.42 mmol) in THF (1 mL). The crude was stirred at −78° C. for 1 hr. This solution was then cannulated to a solution of 3-fluoro-4-((R)-7-oxo-6,7-dihydro-5H-pyrrolo[1,2-c]imidazol-5-yl)-benzonitrile (50 mg, 0.21 mmol) in THF (1 mL) cooled at −78° C. After stirring at −78° C. for 2 hrs, the crude was warmed to room temperature. The crude was stirred at room temperature for 1 hr. The crude was quenched with sat. NH$_4$Cl. The crude was diluted in EtOAc. The organic layer was washed with brine, dried over MgSO$_4$, filtered and concentrated. The crude was purified via preparation plate using 7% (2M NH$_3$ in MeOH)/CH$_2$Cl$_2$ to give 18 mg of the entitled product as the major diastereomer. MS 377.0 (M+H); LCMS condition A, retention time 1.23 min.

$^1$H NMR (400 MHz, CDCl$_3$) δ ppm 3.09 (dd, 1H), 3.84 (dd, 1H), 5.96 (d, 1H), 7.02 (s, 1H), 7.24-7.53 (m, 6H), 7.85 (d, 1H), 7.93 (d, 1H).

General Condition G for 1,2 Addition

Example 1-7

4-((5R)-8-(4-fluorophenyl)-8-hydroxy-5,6,7,8-tetrahydroimidazo[1,5-a]pyridin-5-yl)benzonitrile

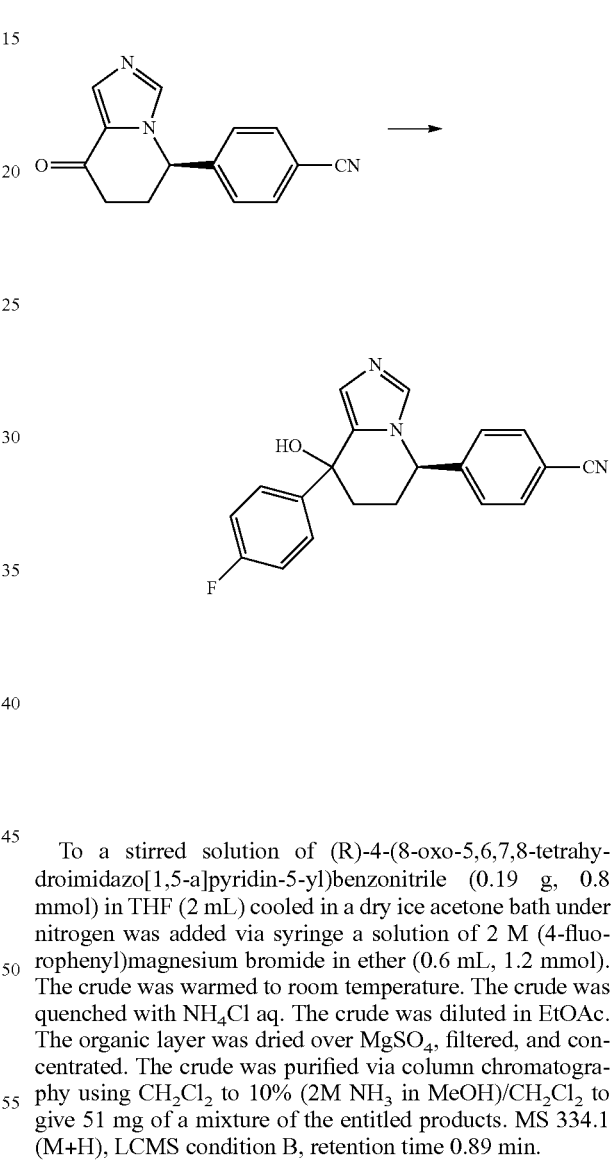

To a stirred solution of (R)-4-(8-oxo-5,6,7,8-tetrahydroimidazo[1,5-a]pyridin-5-yl)benzonitrile (0.19 g, 0.8 mmol) in THF (2 mL) cooled in a dry ice acetone bath under nitrogen was added via syringe a solution of 2 M (4-fluorophenyl)magnesium bromide in ether (0.6 mL, 1.2 mmol). The crude was warmed to room temperature. The crude was quenched with NH$_4$Cl aq. The crude was diluted in EtOAc. The organic layer was dried over MgSO$_4$, filtered, and concentrated. The crude was purified via column chromatography using CH$_2$Cl$_2$ to 10% (2M NH$_3$ in MeOH)/CH$_2$Cl$_2$ to give 51 mg of a mixture of the entitled products. MS 334.1 (M+H), LCMS condition B, retention time 0.89 min.

Following compounds are prepared using similar procedure as example 1-1 through example 1-7 using either 3-fluoro-4-((R)-7-oxo-6,7-dihydro-5H-pyrrolo[1,2-c]imidazol-5-yl)-benzonitrile or (R)-4-(8-oxo-5,6,7,8-tetrahydroimidazo[1,5-a]pyridin-5-yl)benzonitrile with appropriate reagents and conditions: Note when possible, separation of diastereomers were individually achieved with preparation plates, flash chromatography, prep-LCMS, HPLC, and or using HPLC CHIRALPAK® HPLC columns (such as AD, OJ, OD, etc.) which are purchased from Daicel.

| Example # | Product | Reagent | General Condition | LCMS-RT (condition) | MS (M + 1) |
|---|---|---|---|---|---|
| Example 1-8 | 3-fluoro-4-((5R,7S)-7-(4-fluorophenyl)-7-hydroxy-6,7-dihydro-5H-pyrrolo[1,2-c]imidazol-5-yl)benzonitrile | 4-F-C6H4-MgBr | A | 0.92 min (B) | 338.1 |
| Example 1-9 | 3-fluoro-4-((5R,7R)-7-(4-fluorophenyl)-7-hydroxy-6,7-dihydro-5H-pyrrolo[1,2-c]imidazol-5-yl)benzonitrile | 4-F-C6H4-MgBr | A | 0.98 min (B) | 338.3 |
| Example 1-10 | 4-((5R,7S)-7-(4-bromophenyl)-7-hydroxy-6,7-dihydro-5H-pyrrolo[1,2-c]imidazol-5-yl)-3-fluorobenzonitrile | 4-Br-C6H4-I | C | 1.32 min (A) | 400.0 |
| Example 1-11 | 4-((5R)-7-(3-bromophenyl)-7-hydroxy-6,7-dihydro-5H-pyrrolo[1,2-c]imidazol-5-yl)-3-fluorobenzonitrile | 1,3-Br2-C6H4 | E | 1.03 min (B) | 400.0 |

| Example # | Product | Reagent | General Condition | LCMS-RT (condition) | MS (M + 1) |
|---|---|---|---|---|---|
| Example 1-12 | 3-fluoro-4-((5R,7R)-7-hydroxy-7-phenethyl-6,7-dihydro-5H-pyrrolo[1,2-c]imidazol-5-yl)benzonitrile | phenethyl-MgBr | A | 1.32 min (A) | 348.3 |
| Example 1-13 | 4-((5R,7S)-7-(benzo[d][1,3]dioxol-5-yl)-7-hydroxy-6,7-dihydro-5H-pyrrolo[1,2-c]imidazol-5-yl)-3-fluorobenzonitrile | benzo[d][1,3]dioxol-5-yl-MgBr | A | 0.97 min (B) | 364.0 |
| Example 1-14 | 3-fluoro-4-((5R)-7-hydroxy-7-(2-methoxyphenyl)-6,7-dihydro-5H-pyrrolo[1,2-c]imidazol-5-yl)benzonitrile | 2-methoxyphenyl-MgBr | A | 1.18 min (A) | 350.2 |
| Example 1-15 | 3-fluoro-4-((5R)-7-hydroxy-7-(3-methoxyphenyl)-6,7-dihydro-5H-pyrrolo[1,2-c]imidazol-5-yl)benzonitrile | 3-methoxyphenyl-MgBr | A | 0.90 min (B) 0.96 min (B) | 350.1 350.1 |

-continued

| Example # | Product | Reagent | General Condition | LCMS-RT (condition) | MS (M + 1) |
|---|---|---|---|---|---|
| Example 1-16 | 3-fluoro-4-((5R,7S)-7-hydroxy-7-(naphthalen-2-yl)-6,7-dihydro-5H-pyrrolo[1,2-c]imidazol-5-yl)benzonitrile | naphthalen-2-yl MgBr | A | 1.08 min (B) | 370.1 |
| Example 1-17 | 3-fluoro-4-((5R,7R)-7-hydroxy-7-(naphthalen-2-yl)-6,7-dihydro-5H-pyrrolo[1,2-c]imidazol-5-yl)benzonitrile | naphthalen-2-yl MgBr | A | 1.40 min (B) | 370.2 |
| Example 1-18 | 3-fluoro-4-((5R,7S)-7-hydroxy-7-(7-methoxynaphthalen-2-yl)-6,7-dihydro-5H-pyrrolo[1,2-c]imidazol-5-yl)benzonitrile | 7-methoxynaphthalen-2-yl MgBr | A | 400.2 min (B) | 1.18 |
| Example 1-19 | 3-fluoro-4-((5R,7R)-7-hydroxy-7-(7-methoxynaphthalen-2-yl)-6,7-dihydro-5H-pyrrolo[1,2-c]imidazol-5-yl)benzonitrile | 7-methoxynaphthalen-2-yl MgBr | A | 400.2 min (B) | 1.25 |

-continued

| Example # | Product | Reagent | General Condition | LCMS-RT (condition) | MS (M + 1) |
|---|---|---|---|---|---|
| Example 1-20 | 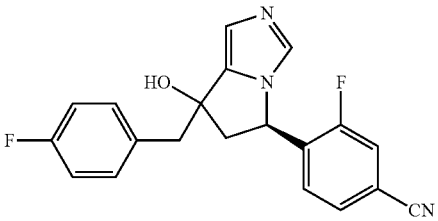<br>3-fluoro-4-((5R)-7-(4-fluorobenzyl)-7-hydroxy-6,7-dihydro-5H-pyrrolo[1,2-c]imidazol-5-yl)benzonitrile | 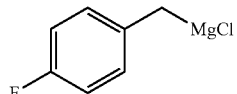 | A | 0.92 min (B) 1.00 min (B) | 352.1 352.1 |
| Example 1-21 | 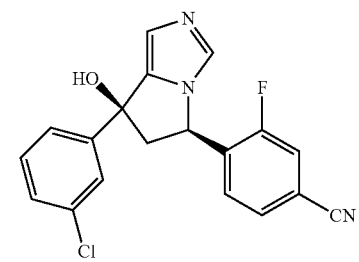<br>4-((5R,7S)-7-(3-chlorophenyl)-7-hydroxy-6,7-dihydro-5H-pyrrolo[1,2-c]imidazol-5-yl)-3-fluorobenzonitrile | 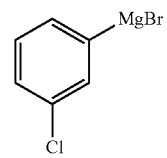 | A | 1.08 min (B) | 354.02 |
| Example 1-22 | 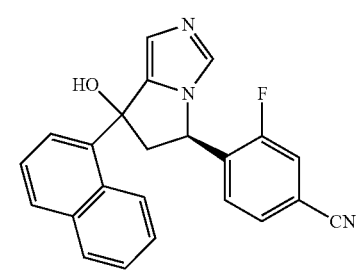<br>3-fluoro-4-((5R)-7-hydroxy-7-(naphthalen-1-yl)-6,7-dihydro-5H-pyrrolo[1,2-c]imidazol-5-yl)benzonitrile |  | A | 1.19 min (B) | 370.1 |
| Example 1-23 | 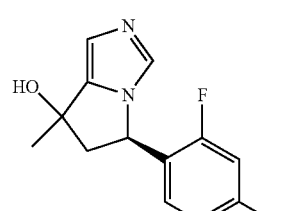<br>3-fluoro-4-((5R)-7-hydroxy-7-methyl-6,7-dihydro-5H-pyrrolo[1,2-c]imidazol-5-yl)benzonitrile | CH$_3$MgBr | A | 0.31 min (B) 0.49 min (B) | 258.0 258.0 |

-continued

| Example # | Product | Reagent | General Condition | LCMS-RT (condition) | MS (M + 1) |
|---|---|---|---|---|---|
| Example 1-24 | 4-((5R,7S)-7-(biphenyl-4-yl)-7-hydroxy-6,7-dihydro-5H-pyrrolo[1,2-c]imidazol-5-yl)-3-fluorobenzonitrile | MgBr-biphenyl | A | 1.16 min (B) | 396.1 |
| Example 1-25 | 4-((5R,7R)-7-(biphenyl-4-yl)-7-hydroxy-6,7-dihydro-5H-pyrrolo[1,2-c]imidazol-5-yl)-3-fluorobenzonitrile | MgBr-biphenyl | A | 1.18 min (B) | 396.2 |
| Example 1-26 | 4-((5R,7S)-7-(3-(dimethylamino)phenyl)-7-hydroxy-6,7-dihydro-5H-pyrrolo[1,2-c]imidazol-5-yl)-3-fluorobenzonitrile | 3-(dimethylamino)phenyl MgBr | A | 1.05 min (B) | 363.2 |
| Example 1-27 | 4-((5R,7S)-7-(4-(benzyloxy)phenyl)-7-hydroxy-6,7-dihydro-5H-pyrrolo[1,2-c]imidazol-5-yl)-3-fluorobenzonitrile | 4-(BnO)phenyl MgBr | A | 1.31 min (B) | 426.0 |

-continued

| Example # | Product | Reagent | General Condition | LCMS-RT (condition) | MS (M + 1) |
|---|---|---|---|---|---|
| Example 1-28 | 4-((5R,7R)-7-(4-(benzyloxy)phenyl)-7-hydroxy-6,7-dihydro-5H-pyrrolo[1,2-c]imidazol-5-yl)-3-fluorobenzonitrile | BnO–C6H4–MgBr | A | 1.28 min (B) | 426.0 |
| Example 1-29 | 4-((5R)-7-(3,4-dimethoxyphenyl)-7-hydroxy-6,7-dihydro-5H-pyrrolo[1,2-c]imidazol-5-yl)-3-fluorobenzonitrile | 3,4-(MeO)2–C6H3–MgBr | A | 0.81 min (B) | 380.3 |
| Example 1-30 | 3-fluoro-4-((5R,7S)-7-(4'-fluorobiphenyl-3-yl)-7-hydroxy-6,7-dihydro-5H-pyrrolo[1,2-c]imidazol-5-yl)benzonitrile | 4'-F-biphenyl-3-MgBr | A | 1.19 min (B) | 414.1 |
| Example 1-31 | 3-fluoro-4-((5R,7S)-7-hydroxy-7-(4-methoxyphenyl)-6,7-dihydro-5H-pyrrolo[1,2-c]imidazol-5-yl)benzonitrile | MeO–C6H4–MgBr | A | 1.02 min (B) | 351.0 |

| Example # | Product | Reagent | General Condition | LCMS-RT (condition) | MS (M + 1) |
|---|---|---|---|---|---|
| Example 1-32 | 4-((5R,7S)-7-(4-ethylphenyl)-7-hydroxy-6,7-dihydro-5H-pyrrolo[1,2-c]imidazol-5-yl)-3-fluorobenzonitrile | 4-ethylphenyl-MgBr | A | 1.30 min (A) | 348.3 |
| Example 1-33 | 4-((5R,7S)-7-(3-ethylphenyl)-7-hydroxy-6,7-dihydro-5H-pyrrolo[1,2-c]imidazol-5-yl)-3-fluorobenzonitrile | 1-bromo-3-ethylbenzene | D | 1.30 min (A) | 348.2 |
| Example 1-34 | 4-((5R,7S)-7-(3-(1,1-difluoroethyl)phenyl)-7-hydroxy-6,7-dihydro-5H-pyrrolo[1,2-c]imidazol-5-yl)-3-fluorobenzonitrile | 1-(1,1-difluoroethyl)-3-iodobenzene | C | 1.31 min (A) | 384.1 |
| Example 1-35 | 4-((5R,7R)-7-(3-(1,1-difluoroethyl)phenyl)-7-hydroxy-6,7-dihydro-5H-pyrrolo[1,2-c]imidazol-5-yl)-3-fluorobenzonitrile | 1-(1,1-difluoroethyl)-3-iodobenzene | C | 1.30 min (A) | 384.2 |

-continued

| Example # | Product | Reagent | General Condition | LCMS-RT (condition) | MS (M + 1) |
|---|---|---|---|---|---|
| Example 1-36 | 3-fluoro-4-((5R,7S)-7-hydroxy-7-(4-(trifluoromethyl)phenyl)-6,7-dihydro-5H-pyrrolo[1,2-c]imidazol-5-yl)benzonitrile | F₃C—C₆H₄—I | C | 1.56 min (A) | 388.0 |
| Example 1-37 | 3-fluoro-4-((5R,7S)-7-hydroxy-7-(4-propylphenyl)-6,7-dihydro-5H-pyrrolo[1,2-c]imidazol-5-yl)benzonitrile | 4-propylphenyl-MgBr | A | 1.40 min (A) | 362.2 |
| Example 1-38 | 3-fluoro-4-((5R,7S)-7-hydroxy-7-(4-isopropylphenyl)-6,7-dihydro-5H-pyrrolo[1,2-c]imidazol-5-yl)benzonitrile | 4-isopropylphenyl-MgBr | A | 1.38 min (A) | 362.2 |
| Example 1-39 | 4-((5R)-8-(4'-fluorobiphenyl-3-yl)-8-hydroxy-5,6,7,8-tetrahydroimidazo[1,5-a]pyridin-5-yl)benzonitrile | 4'-fluorobiphenyl-3-yl-MgBr | G | 1.18 min (B) | 410.1 |

| Example # | Product | Reagent | General Condition | LCMS-RT (condition) | MS (M + 1) |
|---|---|---|---|---|---|
| Example 1-40 | 4-((5R,7S)-7-(4-chlorophenyl)-7-hydroxy-6,7-dihydro-5H-pyrrolo[1,2-c]imidazol-5-yl)-3-fluorobenzonitrile | 4-chlorophenyl MgBr | A | 1.30 min (B) | 354.1 |
| Example 1-41 | 4-((5R,8S)-8-(biphenyl-4-yl)-8-hydroxy-5,6,7,8-tetrahydroimidazo[1,5-a]pyridin-5-yl)benzonitrile | biphenyl-4-yl MgBr | G | 1.15 min (B) | 392.1 |
| Example 1-42 | 4-((5R,8R)-8-(biphenyl-4-yl)-8-hydroxy-5,6,7,8-tetrahydroimidazo[1,5-a]pyridin-5-yl)benzonitrile | biphenyl-4-yl MgBr | G | 1.16 min (B) | 392.2 |
| Example 1-43 | 4-((5R)-8-hydroxy-8-(naphthalen-2-yl)-5,6,7,8-tetrahydroimidazo[1,5-a]pyridin-5-yl)benzonitrile | naphthalen-2-yl MgBr | G | 1.17 min (B) | 366.2 |

| Example # | Product | Reagent | General Condition | LCMS-RT (condition) | MS (M + 1) |
|---|---|---|---|---|---|
| Example 1-44 | 4-((5R)-8-hydroxy-8-methyl-5,6,7,8-tetrahydroimidazo[1,5-a]pyridin-5-yl)benzonitrile | CH3MgBr | G | 0.50 min (B) | 254.1 |
| Example 1-45 | 3-fluoro-4-((5R,7S)-7-hydroxy-7-(4-morpholinophenyl)-6,7-dihydro-5H-pyrrolo[1,2-c]imidazol-5-yl)benzonitrile | 4-bromo-morpholinobenzene | E | 1.14 min (A) | 405.2 |
| Example 1-46 | 3-fluoro-4-((5R,7S)-7-hydroxy-7-(pyridin-3-yl)-6,7-dihydro-5H-pyrrolo[1,2-c]imidazol-5-yl)benzonitrile | 3-bromopyridine | E | 0.94 min (A) | 321.3 |
| Example 1-47 | 3-fluoro-4-((5R)-7-hydroxy-7-(isoquinolin-6-yl)-6,7-dihydro-5H-pyrrolo[1,2-c]imidazol-5-yl)benzonitrile | 6-bromoisoquinoline | E | 1.06 min (A) | 371.1 |

-continued

| Example # | Product | Reagent | General Condition | LCMS-RT (condition) | MS (M + 1) |
|---|---|---|---|---|---|
| Example 1-48 | 3-fluoro-4-((5R,7S)-7-hydroxy-7-(quinolin-3-yl)-6,7-dihydro-5H-pyrrolo[1,2-c]imidazol-5-yl)benzonitrile | 3-bromoquinoline | E | 1.12 min (A) | 371.1 |
| Example 1-49 | 3-fluoro-4-((5R,7R)-7-hydroxy-7-(pyridin-2-yl)-6,7-dihydro-5H-pyrrolo[1,2-c]imidazol-5-yl)benzonitrile | 2-bromopyridine | E | 1.01 min (A) | 321.0 |
| Example 1-50 | 3-fluoro-4-((5R,7S)-7-hydroxy-7-(1-methyl-1H-indol-2-yl)-6,7-dihydro-5H-pyrrolo[1,2-c]imidazol-5-yl)benzonitrile | 1-methylindole | F | 1.32 min (A) | 373.0 |
| Example 1-51 | 3-fluoro-4-((5R,7S)-7-hydroxy-7-(pyridin-2-ylmethyl)-6,7-dihydro-5H-pyrrolo[1,2-c]imidazol-5-yl)benzonitrile | 2-methylpyridine | F | 1.02 min (A) | 335.2 |

Example 1-8

1H NMR (400 MHz, CDCl$_3$) δ ppm 2.25-2.48 (m, 1H), 2.76 (dd, 1H), 3.26-3.48 (m, 1H), 5.83-6.03 (m, 1H), 6.95 (br. s., 1H), 7.04-7.14 (m, 2H), 7.31-7.41 (m, 2H), 7.45 (d, 1H), 7.52 (d, 1H), 7.56-7.68 (m, 2H).

Example 1-9

1H NMR (400 MHz, CDCl$_3$) δ ppm 2.53 (br. s., 1H), 2.97 (d, 1H), 3.34 (dd, 1H), 5.76 (d, 1H), 6.98 (s, 1H), 7.08 (t, 2H), 7.16 (t, 1H), 7.37-7.47 (m, 2H), 7.48-7.61 (m, 3H).

Example 1-10

1H NMR (400 MHz, CDCl$_3$) δ ppm 2.91 (dd, 1H), 3.21 (dd, 1H), 5.68 (d, 1H), 6.56 (s, 1H), 7.10 (t, 1H), 7.23 (s, 1H), 7.26-7.36 (m, 4H), 7.37-7.44 (m, 2H).

Example 1-12

1H NMR (400 MHz, CDCl$_3$) δ ppm 2.06-2.28 (m, 2H), 2.64 (dd, 1H), 2.70-2.91 (m, 2H), 3.14 (dd, 1H), 5.59 (dd, 1H), 6.87 (s, 1H), 6.99-7.15 (m, 4H), 7.16-7.25 (m, 3H), 7.24-7.36 (m, 2H).

Example 1-13

1H NMR (400 MHz, CDCl$_3$) δ ppm 2.33 (br. s., 1H), 2.89 (d, 1H), 3.28 (dd, 1H), 5.71 (d, 1H), 5.92 (s, 2H), 6.73 (d, 1H), 6.87-6.99 (m, 3H), 7.08 (t, 1H), 7.29-7.36 (m, 1H), 7.37 (s, 1H), 7.43 (s, 1H).

Example 1-16

1H NMR (400 MHz, CDCl$_3$) δ ppm 2.96 (dd, 1H), 3.32 (dd, 1H), 4.83 (br. s., 1H), 5.57-5.71, (m, 1H), 6.72 (s, 1H), 7.10 (t, 1H), 7.24 (s, 1H), 7.26-7.35 (m, 2H), 7.35-7.52 (m, 3H), 7.57-7.68 (m, 1H), 7.68-7.80 (m, 2H), 7.86 (s, 1H).

Example 1-17

1H NMR (400 MHz, CDCl$_3$) δ ppm 2.75 (dd, 1H), 3.32 (dd, 1H), 3.39 (s, 1H), 5.88 (dd, 1H), 6.72 (s, 1H), 7.12 (s, 1H), 7.16-7.27 (m, 1H), 7.30-7.38 (m, 2H), 7.38-7.46 (m, 2H), 7.54 (dd, 1H), 7.68-7.79 (m, 3H), 8.02 (d, 1H).

Example 1-18

1H NMR (400 MHz, CDCl$_3$) δ ppm 2.98 (d, 1H), 3.36 (dd, 1H), 3.85 (s, 3H), 5.71 (d, 1H), 6.90 (br. s., 1H), 7.03-7.16 (m, 3H), 7.25-7.40 (m, 3H), 7.46 (d, 1H), 7.62 (d, 1H), 7.67 (d, 1H), 7.82 (s, 1H).

Example 1-19

1H NMR (400 MHz, CDCl3) (ppm 2.45 (br. s., 1H), 2.78 (dd, 1H), 3.36 (dd, 1H), 3.86 (s, 3H), 5.92 (dd, 1H), 6.96 (br. s., 1H), 7.02-7.16 (m, 2H), 7.25-7.35 (m, 2H), 7.35-7.45 (m, 2H), 7.55 (dd, 1H), 7.68 (t, 2H), 7.98 (s, 1H).

Example 1-21

1H NMR (400 MHz, CDCl3) (ppm 2.92 (d, 1H), 3.27 (dd, 1H), 5.73 (d, 1H), 6.81 (s, 1H), 7.10 (t, 1H), 7.21-7.28 (m, 2H), 7.28-7.43 (m, 4H), 7.47 (br. s., 1H).

Example 1-24

1H NMR (400 MHz, CDCl3) (ppm 2.64-2.85 (m, 1H), 2.93 (br. s., 1H), 3.17-3.46 (m, 1H), 5.78-6.02 (m, 1H), 6.93 (br. s., 1H), 7.23-7.34 (m, 3H), 7.34-7.46 (m, 4H), 7.53 (d, d, 4H), 7.62 (d, 2H).

Example 1-25

1H NMR (400 MHz, CDCl3) (ppm 2.82-3.06 (m, 2H), 3.35 (dd, 1H), 5.74 (d, 1H), 6.90 (s, 1H), 7.12 (t, 1H), 7.24-7.33 (m, 1H), 7.33-7.45 (m, 5H), 7.46-7.60 (m, 6H).

Example 1-26

1H NMR (400 MHz, CDCl3) (ppm 2.88 (s, 6H), 2.92 (d, 1H), 3.33 (dd, 1H), 5.73 (d, 1H), 6.64 (dd, 1H), 6.75 (d, 1H), 6.83-6.88 (m, 1H), 6.94 (s, 1H), 7.12 (t, 1H), 7.17-7.21 (m, 1H), 7.35 (d, 1H), 7.36-7.38 (m, 1H), 7.47 (s, 1H).

Example 1-27

1H NMR (400 MHz, CDCl3) (ppm 2.90 (dd, 1H), 3.26 (dd, 1H), 4.99 (s, 2H), 5.68 (d, 1H), 6.82 (s, 1H), 6.86-6.96 (m, 2H), 7.09 (t, 1H), 7.21-7.43 (m, 10H).

Example 1-28

1H NMR (400 MHz, CDCl$_3$) δ ppm 2.35 (br. s., 1H), 2.67 (dd, 1H), 3.21-3.37 (m, 1H), 5.01 (s, 2H), 5.86 (br. s., 1H), 6.87-6.95 (m, 2H), 7.21-7.44 (m, 10H), 7.44-7.50 (m, 2H).

Example 1-30

1H NMR (400 MHz, CDCl3) (ppm 2.98 (d, 1H), 3.34 (dd, 1H), 3.58 (br. s., 1H), 5.75 (d, 1H), 6.87 (br. s., 1H), 7.03 (t, 2H), 7.12-7.21 (m, 1H), 7.28-7.52 (m, 8H), 7.65 (s, 1H).

Example 1-31

1H NMR (400 MHz, CDCl$_3$) δ ppm 3.11 (dd, 1H), 3.70 (dd, 1H), 3.83 (s, 3H), 5.95 (dd, 1H), 6.90 (s, 1H), 6.92 (s, 1H), 7.00 (t, 1H), 7.42-7.52 (m, 2H), 7.61 (d, 2H), 7.69-7.78 (m, 2H).

Example 1-32

1H NMR (400 MHz, CDCl$_3$) δ ppm 1.15 (t, 3H), 2.57 (q, 2H), 2.90 (dd, 1H), 3.26 (dd, 1H), 3.37 (s, 1H), 5.67 (d, 1H), 6.67 (br. s., 1H), 7.05-7.17 (m, 3H), 7.25 (br. s., 1H), 7.33 (dd, 4H).

Example 1-33

1H NMR (400 MHz, CDCl$_3$) δ ppm 1.17 (t, 3H), 2.59 (q, 2H), 2.92 (d, 1H), 3.32 (dd, 1H), 5.73 (d, 1H), 6.93 (br. s., 1H), 7.12 (d, 2H), 7.21-7.39 (m, 4H), 7.41-7.51 (m, 2H).

Example 1-34

1H NMR (400 MHz, CDCl$_3$) δ ppm 1.85 (t, 3H), 2.95 (d, 1H), 3.31 (dd, 1H), 5.76 (d, 1H), 6.89 (s, 1H), 7.11 (t, 1H), 7.29-7.45 (m, 4H), 7.45-7.55 (m, 2H), 7.66 (s, 1H).

Example 1-35

1H NMR (400 MHz, CDCl$_3$) δ ppm 1.82 (t, 3H), 2.84-3.00 (m, 1H), 3.29 (dd, 1H), 5.73 (d, 1H), 6.73 (s, 1H), 7.12 (t, 1H), 7.30-7.42 (m, 5H), 7.46 (d, 1H), 7.65 (s, 1H).

Example 1-36

1H NMR (400 MHz, CDCl$_3$) δ ppm 2.95 (dd, 1H), 3.24 (dd, 1H), 5.71 (d, 1H), 6.54 (s, 1H), 7.14 (t, 1H), 7.25 (s, 1H), 7.30-7.38 (m, 2H), 7.48-7.59 (m, 4H).

Example 1-37

1H NMR (400 MHz, CDCl$_3$) δ ppm 0.88 (t, 3H), 1.53-1.62 (m, 2H), 2.45-2.59 (m, 2H), 2.82 (broad s, 1H), 2.91 (dd, 1H), 3.30 (dd, 1H), 5.71 (d, 1H), 6.88 (s, 1H), 7.02-7.16 (m, 3H), 7.27-7.38 (m, 4H), 7.39 (s, 1H).

Example 1-38

1H NMR (400 MHz, CDCl$_3$) δ ppm 1.19 (d, 6H), 1.65 (br. s., 1H), 2.82-2.89 (m, 1H), 2.92 (d, 1H), 3.31 (dd, 1H), 5.72 (d, 1H), 6.94 (s, 1H), 7.12 (t, 1H), 7.15-7.22 (m, 2H), 7.32-7.41 (m, 4H), 7.45 (s, 1H).

Example 1-40

1H NMR (400 MHz, CDCl$_3$) δ ppm 3.64 (d, 1H), 3.96 (dd, 1H), 5.17 (br. s., 1H), 6.43 (d, 1H), 7.40 (s, 1H), 7.83 (t, 1H), 7.99 (d, 2H), 8.03 (s, 1H), 8.05-8.13 (m, 4H).

Example 1-41

1H NMR (400 MHz, CDCl$_3$) δ ppm 1.81-2.03 (m, 3H), 2.26 (br. s., 1H), 2.78-2.96 (m, 1H), 5.54 (dd, 1H), 6.89 (s, 1H), 6.97 (m, 2H), 7.25-7.35 (m, 2H), 7.38 (t, 2H), 7.48-7.58 (m, 6H), 7.61 (m, 2H).

Example 1-42

1H NMR (400 MHz, CDCl$_3$) δ ppm 2.00-2.26 (m, 3H), 2.39-2.59 (m, 2H), 5.15 (dd, 1H), 6.77 (s, 1H), 7.07 (s, 1H), 7.24-7.33 (m, 1H), 7.33-7.43 (m, 4H), 7.49-7.57 (m, 6H), 7.66 (d, 2H).

Example 1-45

1H NMR (400 MHz, CDCl$_3$) δ ppm 2.72-3.02 (m, 2H), 3.02-3.18 (m, 4H), 3.27 (dd, 1H), 3.67-3.89 (m, 4H), 5.69 (d, 1H), 6.73-6.95 (m, 3H), 7.10 (t, 1H), 7.28-7.50 (m, 5H).

Example 1-46

1H NMR (400 MHz, CDCl$_3$) δ ppm 2.98 (d, 1H), 3.27 (dd, 1H), 5.76 (d, 1H), 6.64 (br. s., 1H), 7.13 (t, 1H), 7.25 (dd, 1H), 7.37 (d, 2H), 7.43 (br. s., 1H), 7.79 (d, 1H), 8.43 (d, 1H), 8.62 (br. s., 1H).

Example 1-48

1H NMR (400 MHz, CDCl$_3$) δ ppm 3.11 (d, 1H), 3.40 (dd, 1H), 5.83 (d, 1H), 6.98 (br. s., 1H), 7.15-7.24 (m, 1H), 7.36 (s, 1H), 7.39 (s, 1H), 7.52 (t, 1H), 7.56-7.64 (m, 1H), 7.64-7.71 (m, 1H), 7.75 (d, 1H), 8.02 (d, 1H), 8.23 (d, 1H), 8.98 (s, 1H).

Example 1-49

1H NMR (400 MHz, CDCl$_3$) δ ppm 2.84 (dd, 1H), 3.42 (s, 1H), 3.46 (dd, 1H), 5.83 (dd, 1H), 6.80 (s, 1H), 7.22-7.30 (m, 3H), 7.33-7.42 (m, 2H), 7.44 (s, 1H), 7.69 (td, 1H), 8.51 (d, 1H).

Example 1-50

1H NMR (400 MHz, CDCl$_3$) δ ppm 3.13 (dd, 1H), 3.48-3.60 (m, 1H), 3.85 (s, 3H), 5.73 (dd, 1H), 6.44 (s, 1H), 7.04-7.09 (m, 1H), 7.13-7.30 (m, 4H), 7.36-7.44 (m, 3H), 7.51 (d, 1H).

Example 1-51

1H NMR (400 MHz, CDCl$_3$) δ ppm 2.71 (dd, 1H), 3.10-3.22 (m, 2H), 3.36 (d, 1H), 5.65 (dd, 1H), 6.16 (s, 1H), 7.09-7.18 (m, 2H), 7.21-7.31 (m, 2H), 7.34 (t, 2H), 7.62-7.70 (m, 1H), 8.46 (d, 1H).

Example 1-52

4-((5R,7S)-7-(cyclopropylethynyl)-7-hydroxy-6,7-dihydro-6H-pyrrolo[1,2-c]imidazol-5-yl)-3-fluorobenzonitrile

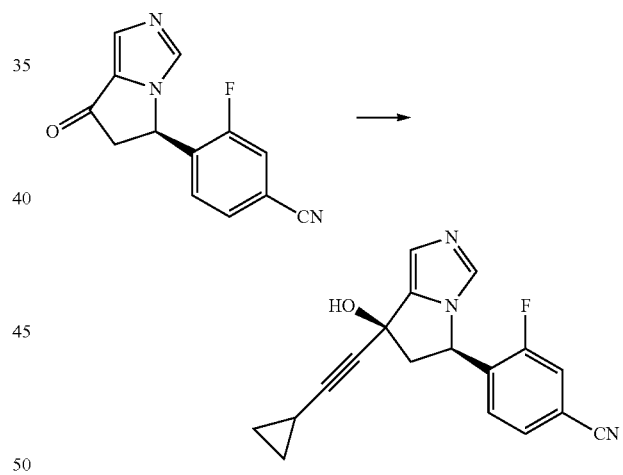

To a solution of ethynylcyclopropane 70 wt % solution in toluene (14.68 μL, 0.124 mmol) in THF (300 μL) cooled to −78° C. was added a solution of 1.6 M n-BuLi in hexane (83 μL, 0.133 mmol). The crude was stirred at −78° C. for 1 hr then warm to 0° C. The crude reaction mixture was cooled back to −78° C. To this crude was added 3-fluoro-4-((R)-7-oxo-6,7-dihydro-5H-pyrrolo[1,2-c]imidazol-5-yl)-benzonitrile (20 mg, 0.083 mmol) as solution in THF (300 μL). The crude was stirred at −78° C. for 1 hr and warm to room temperature. This reaction was quenched with water and extracted the aqueous layer with CH$_2$Cl$_2$. The organic layer was dried over Na$_2$SO$_4$, filtered, and concentrated. The crude was purified via preparation plate using 10% (2M NH$_3$ in MeOH)/CH$_2$Cl$_2$ to give 23 mg of the entitled product as the major diastereomer. MS 308.1 (M+H); LCMS condition B, retention time 0.90 min. 1H NMR (400 MHz, CDCl$_3$) δ ppm 0.56-0.67 (m, 2H), 0.71-0.79 (m, 2H), 1.13-1.27 (m, 1H), 2.83 (d, 1H), 3.48 (dd, 1H), 5.66 (d, 1H), 7.03 (t, 2H), 7.23-7.40 (m, 3H).

Example 1-53a (R)-4-(6,6-dimethyl-7-oxo-6,7-dihydro-5H-pyrrolo[1,2-c]imidazol-5-yl)-3-fluorobenzonitrile

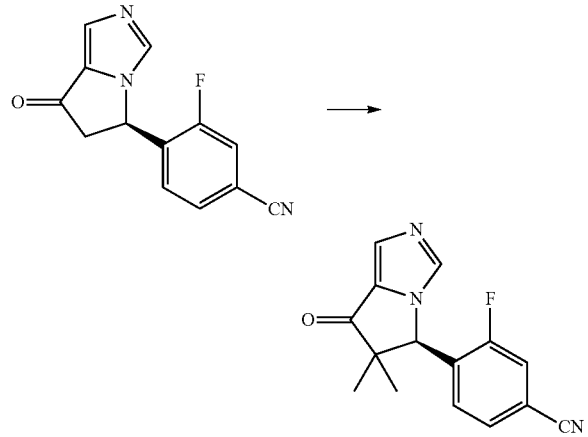

To a solution of 3-fluoro-4-((R)-7-oxo-6,7-dihydro-5H-pyrrolo[1,2-c]imidazol-5-yl)-benzonitrile (50 mg, 0.21 mmol) in THF was added 30% wt NaH in oil (50 mg, 0.62 mmol) at room temperature. The crude was stirred at room temperature for 30 min. To the crude was added iodomethane (0.038 mL, 0.62 mmol). After 30 min stirring at room temperature, another 3 equivalent of NaH and iodomethane was added after 30 min. The crude was monitored by TLC until starting material was consumed. The crude was quenched with H₂O. The organic layer was diluted in EtOAc, washed with brine, dried over MgSO₄, filtered, and concentrated. The crude was purified via preparation plate using 10% MeOH/CH₂Cl₂ to give 34 mg of the entitled product. MS 270.3 (M+H); LCMS condition B, retention time 0.90 min. 1H NMR (400 MHz, CDCl₃) δ ppm 0.89 (s, 3H), 1.53 (s, 3H), 5.74 (s, 1H), 6.76 (t, 1H), 7.41-7.56 (m, 2H), 7.64 (s, 1H), 7.76 (s, 1H).

Example 1-53

3-fluoro-4-((5R,7R)-7-(4-fluorophenyl)-7-hydroxy-6,6-dimethyl-6,7-dihydro-5H-pyrrolo[1,2-c]imidazol-5-yl)benzonitrile

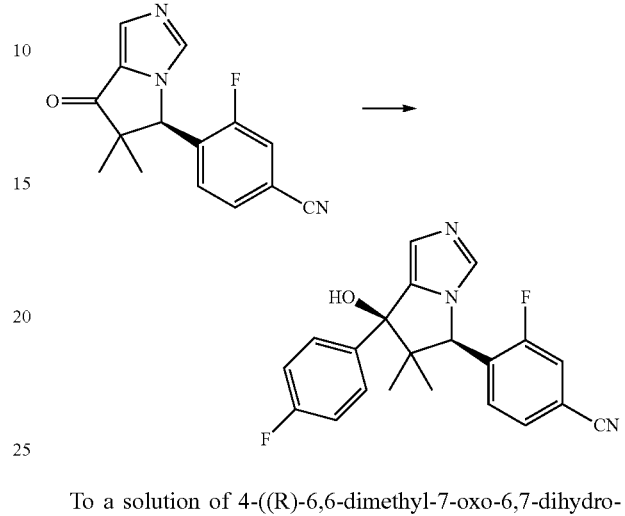

To a solution of 4-((R)-6,6-dimethyl-7-oxo-6,7-dihydro-5H-pyrrolo[1,2-c]imidazol-5-yl)-3-fluoro-benzonitrile (157 mg, 0.45 mmol) in THF cooled to −78° C. was added a 2 M solution of 4-fluoro-phenyl-magnesium bromide in ether (0.39 mL, 0.78 mmol). The crude was allowed to warm to room temperature overnight. The crude was quenched with H₂O and diluted in EtOAc. The organic layer was washed with brine, dried over MgSO₄, filtered, and concentrated. The crude was purified via flash chromatography first with EtOAc/heptane system followed by MeOH/CH₂Cl₂ to give 160 mg of the entitled product. MS 366.2 (M+H); LCMS condition B, retention time 1.14 min. 1H NMR (400 MHz, CDCl₃) δ ppm 0.88 (s, 3H), 1.00 (s, 3H), 5.45 (s, 1H), 6.92 (t, 1H), 7.04 (s, 1H), 7.05-7.13 (m, 2H), 7.32-7.44 (m, 2H), 7.49 (s, 1H), 7.50-7.58 (m, 2H).

Following compounds are prepared using similar procedure as example 1-53 with appropriate reagents. Note when possible, separation of diastereomers were individually achieved with preparation plates, flash chromatography, preparation LCMS, HPLC, and or using HPLC with CHIRALPAK® columns (AD, OJ, OD, etc).

| Example # | Product | Reagent | LCMS-RT (condition) | MS (M + 1) |
|---|---|---|---|---|
| Example 1-54 | 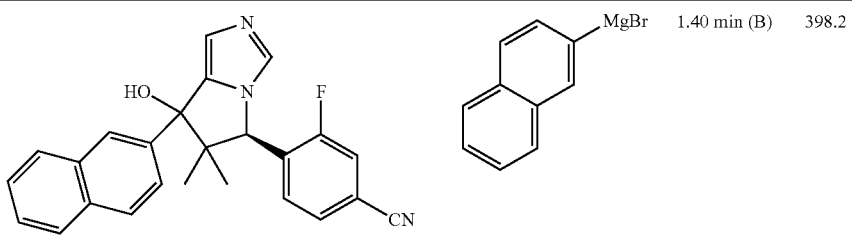<br>3-fluoro-4-((5R)-7-hydroxy-6,6-dimethyl-7-(naphthalen-2-yl)-6,7-dihydro-5H-pyrrolo[1,2-c]imidazol-5-yl)benzonitrile | naphthalen-2-yl MgBr | 1.40 min (B) | 398.2 |

| Example # | Product | Reagent | LCMS-RT (condition) | MS (M + 1) |
|---|---|---|---|---|
| Example 1-55 | 3-fluoro-4-((5R,7R)-7-hydroxy-7-(3-methoxyphenyl)-6,6-dimethyl-6,7-dihydro-5H-pyrrolo[1,2-c]imidazol-5-yl)benzonitrile | 3-methoxyphenyl MgBr | 0.98 min (B) | 378.2 |
| Example 1-56 | 4-((5R,7R)-7-(biphenyl-4-yl)-7-hydroxy-6,6-dimethyl-6,7-dihydro-5H-pyrrolo[1,2-c]imidazol-5-yl)-3-fluorobenzonitrile | biphenyl-4-yl MgBr | 1.44 min (B) | 424.3 |
| Example 1-57 | 3-fluoro-4-((5R,7R)-7-hydroxy-6,6,7-trimethyl-6,7-dihydro-5H-pyrrolo[1,2-c]imidazol-5-yl)benzonitrile | $CH_3MgBr$ | 0.70 min (B) | 286.1 |
| Example 1-58 | 3-fluoro-4-((5R,7R)-7-(4-fluorobenzyl)-7-hydroxy-6,6-dimethyl-6,7-dihydro-5H-pyrrolo[1,2-c]imidazol-5-yl)benzonitrile | 4-fluorophenyl MgBr | 1.19 min (B) | 380.2 |

Example 1-55

1H NMR (400 MHz, CDCl₃) δ ppm 0.91 (s, 3H), 1.03 (d, 3H), 3.81 (s, 3H), 5.45 (s, 1H), 6.89-6.98 (m, 2H), 7.07 (s, 1H), 7.10-7.15 (m, 2H), 7.32 (t, 1H), 7.35-7.44 (m, 2H), 7.48 (s, 1H)

Example 1-56

1H NMR (400 MHz, CDCl₃) δ ppm 0.87 (s, 3H), 0.99 (s, 3H), 3.42 (s, 1H), 5.40 (s, 1H), 6.90 (t, 1H), 6.99 (s, 1H), 7.27-7.34 (m, 3H), 7.36 (d, 1H), 7.40 (d, 2H), 7.50-7.58 (m, 6H).

Example 1-58

1H NMR (400 MHz, CDCl₃) δ ppm 0.93 (s, 3H), 1.32 (s, 3H), 2.91 (d, 2H), 3.40 (s, 1H), 5.30 (s, 1H), 6.45 (s, 1H), 6.67 (t, 1H), 6.93-7.04 (m, 2H), 7.12-7.29 (m, 4H), 7.33 (dd, 1H).

Intermediate 1-59

3-fluoro-4-((5R)-7-hydroxy-7-(3-(tetrahydro-2H-pyran-2-yloxy)phenyl)-6,7-dihydro-5H-pyrrolo[1,2-c]imidazol-5-yl)benzonitrile

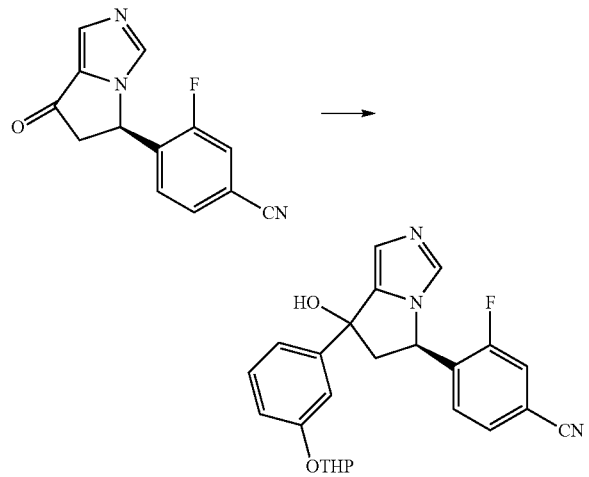

To a stirred solution of 3-fluoro-4-((R)-7-oxo-6,7-dihydro-5H-pyrrolo[1,2-c]imidazol-5-yl)-benzonitrile (3.0 g, 12.44 mmol) in THF (124 ml) cooled to −78° C. via a dry ice and acetone bath was added a 0.25 M solution of (3-(tetrahydro-2H-pyran-2-yloxy)phenyl)magnesium bromide in THF (149 ml, 37.3 mmol). This reaction was allowed to warm to 0° C. over 5 hrs. The dry ice and acetone bath was removed and the reaction was continued for 1 hr at room temperature. The crude was quenched with NH₄Cl aqueous. The crude was diluted in EtOAc. The organic layer was washed with brine, dried over MgSO₄, filtered, and concentrated. The crude was purified via HPLC (10% to 90% MeCN/H₂O, 226 wavelength, 150 min, 10 min runs) to yield 1,2 addition products 3-fluoro-4-((5R)-7-hydroxy-7-(3-(tetrahydro-2H-pyran-2-yloxy)phenyl)-6,7-dihydro-5H-pyrrolo[1,2-c]imidazol-5-yl)benzonitrile (1.87 g). MS 420.1 (M+H); LCMS condition A, retention time 1.30 min. MS 420.0 (M+H); LCMS condition A, retention time 1.35 min.

Example 1-60

3-fluoro-4-((5R,7S)-7-hydroxy-7-(3-hydroxyphenyl)-6,7-dihydro-5H-pyrrolo[1,2-c]imidazol-5-yl)benzonitrile

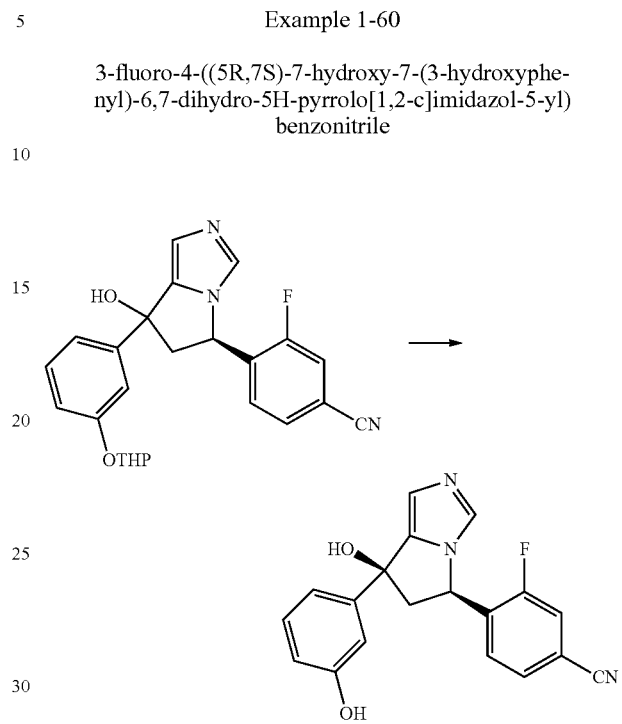

To a solution of 3-fluoro-4-((5R)-7-hydroxy-7-(3-(tetrahydro-2H-pyran-2-yloxy)phenyl)-6,7-dihydro-5H-pyrrolo[1,2-c]imidazol-5-yl)benzonitrile (1.87 g, 4.46 mmol) in anhydrous MeOH (372 ml) was added a 2M solution of hydrochloric acid in ether (9.59 ml, 19.18 mmol) at room temperature. The crude was stirred at room temperature for 2 hrs. The crude was concentrated and quenched with saturated NaHCO₃. The crude was diluted in CH₂Cl₂ and the organic layer was washed with water, brine, dried over MgSO₄, filtered, and concentrated. The crude was purified via HPLC 20%-100% MeCN/H₂O to provide 510 mg of the entitled product as the major diastereomer. MS 336.0 (M+H); LCMS condition A, retention time 0.96 min. 1H NMR (400 MHz, CDCl₃) δ ppm 2.90 (d, 1H), 3.22 (dd, 1H), 5.65 (d, 1H), 6.65-6.72 (m, 2H), 6.90 (s, 1H), 7.02-7.09 (m, 2H), 7.15-7.21 (m, 2H), 7.24 (s, 1H), 7.32 (dd, 2H).

Example 1-61

3-((5R,7S)-5-(4-cyano-2-fluorophenyl)-7-hydroxy-6,7-dihydro-5H-pyrrolo[1,2-c]imidazol-7-yl)phenyl trifluoromethanesulfonate

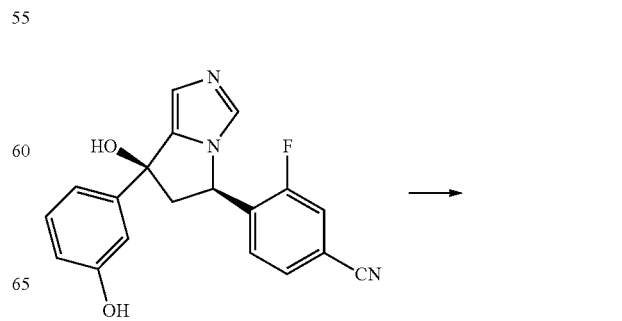

-continued

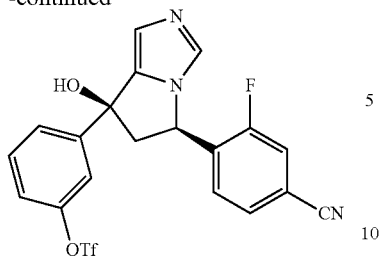

To a solution of 3-fluoro-4-((5R,7S)-7-hydroxy-7-(3-hydroxyphenyl)-6,7-dihydro-5H-pyrrolo[1,2-c]imidazol-5-yl)benzonitrile (0.51 g, 1.521 mmol) in THF (13.58 ml) was added triethylamine (0.530 ml, 3.80 mmol) and Tf$_2$NPh (1.36 g, 3.80 mmol) at room temperature. The crude was stirred at room temperature for 18 hrs. The crude was concentrated. The crude was purified via HPLC 10-90% MeCN/H$_2$O to yield 444 mg of the entitled product. MS 468.0 (M+H); LCMS condition A, retention time 1.42 min. 1H NMR (400 MHz, CDCl$_3$) δ ppm 2.96 (d, 1H), 3.25 (dd, 1H), 5.74 (d, 1H), 6.67 (s, 1H), 7.07-7.19 (m, 2H), 7.31-7.43 (m, 5H), 7.44 (d, 1H).

Example 2-1

3-fluoro-4-((5R,7S)-7-hydroxy-7-(3-(pyrimidin-2-yl)phenyl)-6,7-dihydro-5H-pyrrolo[1,2-c]imidazol-5-yl)benzonitrile

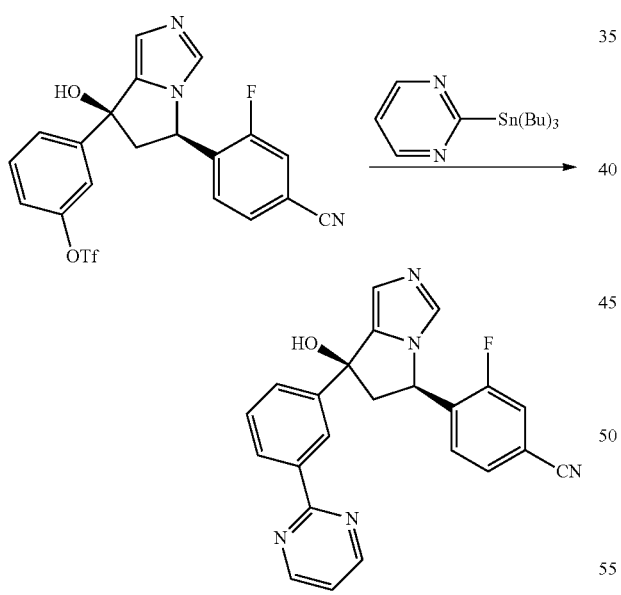

A solution of 3-((5R,7S)-5-(4-cyano-2-fluorophenyl)-7-hydroxy-6,7-dihydro-5H-pyrrolo[1,2-c]imidazol-7-yl)phenyl trifluoromethanesulfonate (20 mg, 0.043 mmol), 2-tributylstannanyl-pyrimidine (47.4 mg, 0.128 mmol) and palladium tetrakis (9.89 mg, 8.56 μmol) in toluene (400 μL) was allowed to stir at 100° C. for overnight. The crude was cooled and concentrated. The crude was partitioned between water and CH$_2$Cl$_2$. The aq. layer was extracted with EtOAc. The organic layer was washed with brine, dried over MgSO$_4$, filtered, and concentrated. The crude was filtered through a plug of silica using EtOAc/heptane. Part of the residue was then purified via HPLC, using 10-90% MeCN/H$_2$O to give 2 mg of the entitled product. MS 398.1 (M+H); LCMS condition B, retention time 0.95 min. 1H NMR (400 MHz, CDCl$_3$) δ ppm 3.06 (dd, 1H), 3.41 (dd, 1H), 5.76-5.90 (m, 1H), 7.04 (s, 1H), 7.14 (t, 1H), 7.28 (t, 1H), 7.34-7.43 (m, 2H), 7.46 (t, 1H), 7.62 (dd, 1H), 7.68 (s, 1H), 8.30-8.40 (m, 1H), 8.52 (t, 1H), 8.73 (d, 2H).

Example 2-2

3-fluoro-4-((5R,7S)-7-hydroxy-7-(3-(pyridin-3-yl)phenyl)-6,7-dihydro-5H-pyrrolo[1,2-c]imidazol-5-yl)benzonitrile

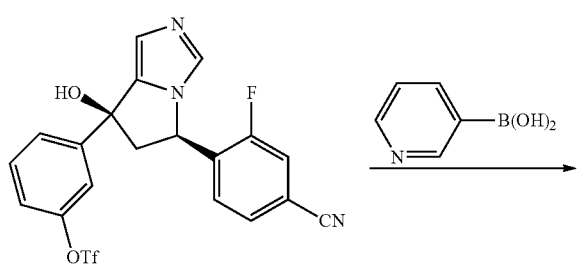

To a conical microwave vial was added pyridin-3-ylboronic acid (16 mg, 0.13 mmol), sodium carbonate (18 mg, 0.17 mmol), Pd.dppf.CH$_2$Cl$_2$ (7.0 mg, 0.009 mmol) followed by the addition of a solution of 3-((5R,7S)-5-(4-cyano-2-fluorophenyl)-7-hydroxy-6,7-dihydro-5H-pyrrolo[1,2-c]imidazol-7-yl)phenyl trifluoromethanesulfonate (20 mg, 0.043 mmol) in DME (2 mL). To this crude was added 0.5 ml distilled water. The reaction was carried out under sealed-vessel microwave heating at 120° C. for 10 min using a Biotage Initiator™ (pre-stirring: 60 s, absorption level: very high). Upon completion of the reaction, the mixture was allowed to cool to room temperature, the Pd catalyst was filtered off with a plug of silica using a monster pipet. The solvent was removed. The crude was concentrated and then purified via HPLC, using 10-90% MeCN/H$_2$O to give 8.2 mg of the entitled product. MS 397.1 (M+H); LCMS condition A, retention time 0.92 min. 1H NMR (400 MHz, CDCl$_3$) δ ppm 2.99 (d, 1H), 3.35 (dd, 1H), 5.77 (d, 1H), 6.83 (s, 1H), 7.10-7.22 (m, 1H), 7.23-7.50 (m, 7H), 7.72-7.84 (m, 2H), 8.36-8.49 (m, 1H), 8.59 (s, 1H).

Following compounds are prepared using similar procedure as example 2-2 with appropriate reagents.

| Example # | Product | Reagent | LCMS-RT (condition) | MS (M + 1) |
|---|---|---|---|---|
| Example 2-3 | 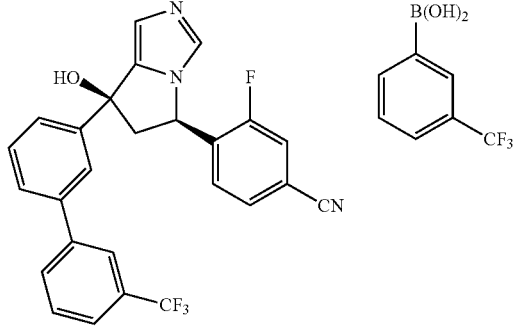<br>3-fluoro-4-((5R,7S)-7-hydroxy-7-(3'-(trifluoromethyl)biphenyl-3-yl)-6,7-dihydro-5H-pyrrolo[1,2-c]imidazol-5-yl)benzonitrile | B(OH)$_2$ with 3-CF$_3$ phenyl | 1.42 min (A) | 464.2 |
| Example 2-4 | 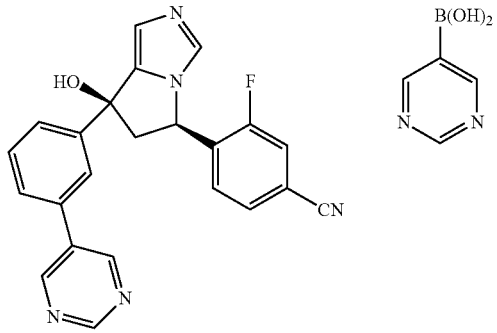<br>3-fluoro-4-((5R,7S)-7-hydroxy-7-(3-(pyrimidin-5-yl)phenyl)-6,7-dihydro-5H-pyrrolo[1,2-c]imidazol-5-yl)benzonitrile | B(OH)$_2$ pyrimidin-5-yl | 0.80 min (A) | 398.1 |
| Example 2-5 | 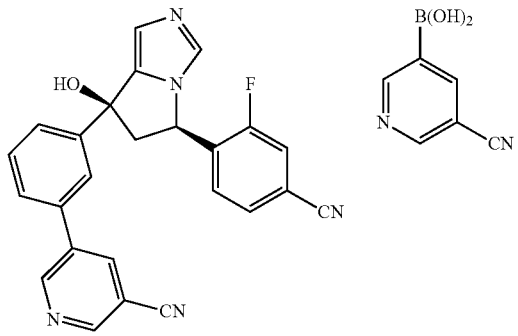<br>5-(3-((5R,7S)-5-(4-cyano-2-fluorophenyl)-7-hydroxy-6,7-dihydro-5H-pyrrolo[1,2-c]imidazol-7-yl)phenyl)nicotinonitrile | B(OH)$_2$ 5-cyanopyridin-3-yl | 1.20 min (A) | 422.3 |

-continued

| Example # | Product | Reagent | LCMS-RT (condition) | MS (M + 1) |
|---|---|---|---|---|
| Example 2-6 | 4-((5R,7S)-7-(3'-chloro-4'-fluorobiphenyl-3-yl)-7-hydroxy-6,7-dihydro-5H-pyrrolo[1,2-c]imidazol-5-yl)-3-fluorobenzonitrile | B(OH)₂ / 3-chloro-4-fluorophenyl | 1.48 min (A) | 448.2 |
| Example 2-7 | 4-((5R,7S)-7-(3',5'-difluorobiphenyl-3-yl)-7-hydroxy-6,7-dihydro-5H-pyrrolo[1,2-c]imidazol-5-yl)-3-fluorobenzonitrile | B(OH)₂ / 3,5-difluorophenyl | 1.30 min (A) | 432.1 |
| Example 2-8 | 4-((5R,7S)-7-(3-(1H-pyrazol-5-yl)phenyl)-7-hydroxy-6,7-dihydro-5H-pyrrolo[1,2-c]imidazol-5-yl)-3-fluorobenzonitrile | 1H-pyrazol-5-yl boronic acid | 0.84 min (A) | 386.1 |

-continued

| Example # | Product | Reagent | LCMS-RT (condition) | MS (M + 1) |
|---|---|---|---|---|
| Example 2-9 | 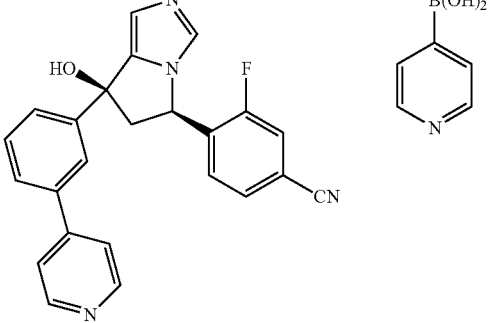<br>3-fluoro-4-((5R,7S)-7-hydroxy-7-(3-(pyridin-4-yl)phenyl)-6,7-dihydro-5H-pyrrolo[1,2-c]imidazol-5-yl)benzonitrile | 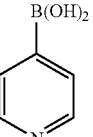 | 0.92 min (A) | 397.1 |
| Example 2-10 | 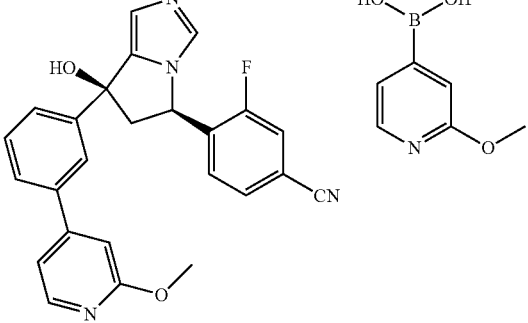<br>3-fluoro-4-((5R,7S)-7-hydroxy-7-(3-(2-methoxypyridin-4-yl)phenyl)-6,7-dihydro-5H-pyrrolo[1,2-c]imidazol-5-yl)benzonitrile | 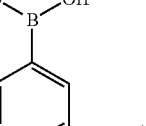 | 1.30 min (A) | 427.3 |
| Example 2-11 | 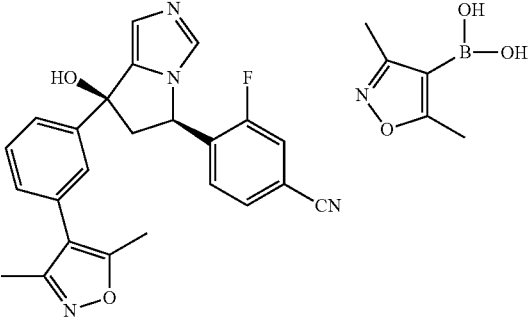<br>4-((5R,7S)-7-(3-(3,5-dimethylisoxazol-4-yl)phenyl)-7-hydroxy-6,7-dihydro-5H-pyrrolo[1,2-c]imidazol-5-yl)-3-fluorobenzonitrile | 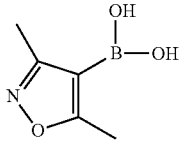 | 1.25 min (A) | 415.2 |

| Example # | Product | Reagent | LCMS-RT (condition) | MS (M + 1) |
|---|---|---|---|---|
| Example 2-12 | 3-fluoro-4-((5R,7S)-7-hydroxy-7-(3-(1-methyl-1H-pyrazol-3-yl)phenyl)-6,7-dihydro-5H-pyrrolo[1,2-c]imidazol-5-yl)benzonitrile | | 1.14 min (A) | 400.2 |
| Example 2-13 | 3-fluoro-4-((5R,7S)-7-(3-(3-fluoropyridin-4-yl)phenyl)-7-hydroxy-6,7-dihydro-5H-pyrrolo[1,2-c]imidazol-5-yl)benzonitrile | | 1.21 min (A) | 415.3 |
| Example 2-14 | 3-fluoro-4-((5R,7S)-7-hydroxy-7-(3-(thiophen-3-yl)phenyl)-6,7-dihydro-5H-pyrrolo[1,2-c]imidazol-5-yl)benzonitrile | | 1.36 min (A) | 402.2 |

| Example # | Product | Reagent | LCMS-RT (condition) | MS (M + 1) |
|---|---|---|---|---|
| Example 2-15 | 3-fluoro-4-((5R,7S)-7-(3-(5-fluoropyridin-3-yl)phenyl)-7-hydroxy-6,7-dihydro-5H-pyrrolo[1,2-c]imidazol-5-yl)benzonitrile | HO-B(OH) (5-fluoropyridin-3-yl boronic acid) | 1.22 min (A) | 415.2 |
| Example 2-16 | 3-fluoro-4-((5R,7S)-7-(3'-fluorobiphenyl-3-yl)-7-hydroxy-6,7-dihydro-5H-pyrrolo[1,2-c]imidazol-5-yl)benzonitrile | B(OH)₂ (3-fluorophenyl boronic acid) | 1.26 min (A) | 414.2 |

Example 2-3

1H NMR (400 MHz, CDCl₃) δ ppm 2.98 (d, 1H), 3.35 (dd, 1H), 5.75 (d, 1H), 6.82 (br. s., 1H), 6.78-6.78 (m, 1H), 7.14 (t, 1H), 7.30-7.44 (m, 5H), 7.44-7.51 (m, 2H), 7.51-7.60 (m, 1H), 7.64 (d, 1H), 7.70 (s, 1H), 7.73 (s, 1H).

Example 2-4

1H NMR (400 MHz, CDCl₃) δ ppm 3.01 (d, 1H), 3.38 (dd, 1H), 5.81 (d, 1H), 6.92 (br. s., 1H), 7.08-7.28 (m, 2H), 7.37 (d, 2H), 7.49-7.61 (m, 3H), 7.74 (br. s., 1H), 8.84 (s, 2H), 9.13 (s, 1H).

Example 2-6

1H NMR (400 MHz, CDCl₃) δ ppm 2.98 (d, 1H), 3.34 (dd, 1H), 5.76 (d, 1H), 6.84 (s, 1H), 7.10 (d, 1H), 7.15 (d, 1H), 7.28-7.44 (m, 8H), 7.49 (dd, 1H), 7.65 (s, 1H).

Example 2-7

1H NMR (400 MHz, CDCl₃) δ ppm 2.99 (d, 1H), 3.34 (dd, 1H), 5.77 (d, 1H), 6.64-6.78 (m, 1H), 6.89 (br. s., 1H), 6.99 (d, 2H), 7.10-7.23 (m, 1H), 7.31-7.52 (m, 6H), 7.67 (s, 1H).

Example 2-8

1H NMR (400 MHz, CDCl₃) δ ppm 2.95 (d, 1H), 3.33 (dd, 1H), 3.59-3.72 (m, 2H), 5.72 (d, 1H), 6.52 (s, 1H), 6.84 (br. s., 1H), 7.09 (t, 1H), 7.26-7.42 (m, 4H), 7.44 (s, 1H), 7.49 (br. s., 1H), 7.63 (d, 1H), 7.92 (s, 1H).

Example 2-9

1H NMR (400 MHz, CDCl₃) δ ppm 2.98 (d, 1H), 3.34 (dd, 1H), 5.76 (d, 1H), 6.83 (s, 1H), 7.13 (t, 1H), 7.32-7.48 (m, 6H), 7.52 (t, 2H), 7.77 (s, 1H), 8.51 (d, 2H).

Example 2-10

1H NMR (400 MHz, CDCl₃) δ ppm 2.96 (d, 1H), 3.31 (dd, 1H), 3.88 (s, 3H), 5.73 (d, 1H), 6.75 (br. s., 1H), 6.79 (s, 1H), 6.97 (d, 1H), 7.12 (t, 1H), 7.27-7.51 (m, 7H), 7.74 (s, 1H), 8.09 (d, 1H).

Example 2-11

1H NMR (400 MHz, CDCl₃) δ ppm 2.18 (s, 3H), 2.32 (s, 3H), 2.96 (d, 1H), 3.34 (dd, 1H), 5.75 (d, 1H), 6.90 (br. s., 1H), 7.10 (t, 1H), 7.16-7.22 (m, 1H), 7.32-7.50 (m, 5H), 7.64 (br. s., 1H).

Example 2-12

1H NMR (400 MHz, CDCl$_3$) δ ppm 2.94 (d, 1H), 3.31 (dd, 1H), 3.83 (s, 3H), 5.72 (d, 1H), 6.82 (s, 1H), 7.12 (t, 1H), 7.23-7.31 (m, 2H), 7.31-7.37 (m, 3H), 7.38 (s, 1H), 7.52 (s, 1H), 7.58 (s, 1H), 7.61 (s, 1H).

Example 2-13

1H NMR (400 MHz, CDCl$_3$) δ ppm 2.97 (dd, 1H), 3.33 (dd, 1H), 4.24 (br. s., 1H), 5.74 (d, 1H), 6.80 (s, 1H), 7.14 (t, 1H), 7.23-7.31 (m, 1H), 7.31-7.41 (m, 3H), 7.41-7.46 (m, 1H), 7.46-7.56 (m, 2H), 7.73 (d, 1H), 8.33 (d, 1H), 8.39 (d, 1H).

Example 2-14

1H NMR (400 MHz, CDCl$_3$) δ ppm 2.94 (d, 1H), 3.32 (dd, 1H), 5.71 (d, 1H), 6.81 (br. s., 1H), 7.11 (t, 1H), 7.23-7.43 (m, 8H), 7.48 (td, 1H), 7.72 (s, 1H).

Example 2-15

1H NMR (400 MHz, CDCl$_3$) δ ppm 2.98 (d, 1H), 3.35 (dd, 1H), 3.40 (s, 1H), 5.76 (d, 1H), 6.79 (s, 1H), 7.15 (t, 1H), 7.19 (s, 1H), 7.28-7.55 (m, 6H), 7.74 (s, 1H), 8.33 (d, 1H), 8.46 (s, 1H).

Example 2-16

1H NMR (400 MHz, CDCl$_3$) δ ppm 2.97 (d, 1H), 3.33 (dd, 1H), 5.73 (d, 1H), 6.80 (br. s., 1H), 6.97 (td, 1H), 7.07-7.18 (m, 2H), 7.21-7.49 (m, 8H), 7.69 (s, 1H).

Example 3-1

3-fluoro-4-((5R,7S)-7-hydroxy-7-(4'-methoxybiphenyl-4-yl)-6,7-dihydro-5H-pyrrolo[1,2-c]imidazol-5-yl)benzonitrile

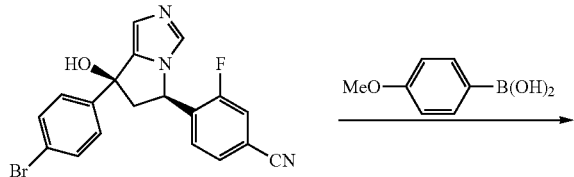

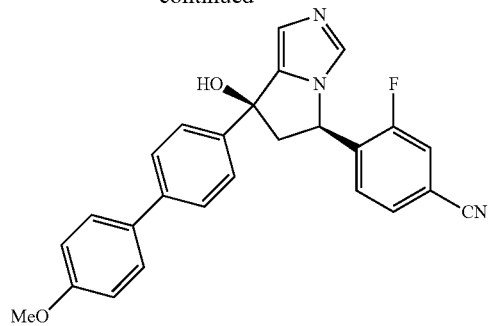

To a solution of 4-[(5R,7S)-7-(4-bromo-phenyl)-7-hydroxy-6,7-dihydro-5H-pyrrolo[1,2-c]imidazol-5-yl]-3-fluoro-benzonitrile (25 mg, 63 μmol) in DME:H$_2$O (4:1, 1 ml) were added Na$_2$CO$_3$ (10 mg, 94 μmol) and 4-methoxyphenylboronic acid (10.5 mg, 69 μmol). To this stirred mixture, PdCl$_2$(dppf).CH$_2$Cl$_2$ complex (1.03 mg, 1.26 μmol) was added. The reaction was carried out under sealed-vessel microwave heating at 120° C. for 10 minutes using a Biotage Initiator™ (pre-stirring: 10 s, absorption level: very high). Upon completion, the mixture was allowed to cool to room temperature, the Pd catalyst was filtered off and the solvent was removed. The crude product obtained was purified using preparative LC-MS and lyophilized to give 3-fluoro-4-[(5R,7S)-7-hydroxy-7-(4'-methoxy-biphenyl-4-yl)-6,7-dihydro-5H-pyrrolo[1,2-c]imidazol-5-yl]-benzonitrile (13 mg, >95% purity). MS 426.0 (M+H), LCMS condition C, retention time 2.06 min. 1H NMR (600 MHz, DMSO-d$_6$) δ ppm 2.90 (dd, 1H), 3.43-3.48 (m, 1H), 3.78 (s, 3H), 6.17 (dd, 1H), 6.59 (br. s., 1H), 7.01-7.03 (m, 2H), 7.33 (t, 1H), 7.53 (d, 2H), 7.60-7.62 (m, 2H), 7.63-7.65 (m, 2H), 7.78 (dd, 1H), 8.02 (dd, 1H), 8.94 (br. s., 1H).

Following compounds are prepared using similar procedure as example 3-1 with appropriate reagents.

| Example # | Product | Reagent | LCMS-RT (condition) | MS (M + 1) |
|---|---|---|---|---|
| Example 3-2 | 3-fluoro-4-((5R,7S)-7-hydroxy-7-(4-(thiazol-4-yl)phenyl)-6,7-dihydro-5H-pyrrolo[1,2-c]imidazol-5-yl)benzonitrile | thiazol-4-yl boronic acid | 1.43 min (C) | 403.0 |

-continued

| Example # | Product | Reagent | LCMS-RT (condition) | MS (M + 1) |
|---|---|---|---|---|
| Example 3-3 | 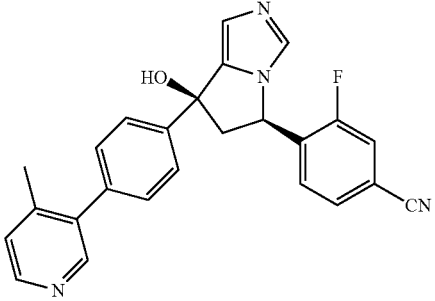<br>3-fluoro-4-((5R,7S)-7-hydroxy-7-(4-(4-methylpyridin-3-yl)phenyl)-6,7-dihydro-5H-pyrrolo[1,2-c]imidazol-5-yl)benzonitrile | 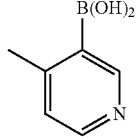 | 1.00 min (C) | 411.0 |
| Example 3-4 | 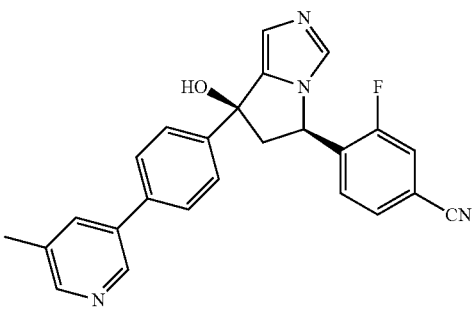<br>3-fluoro-4-((5R,7S)-7-hydroxy-7-(4-(5-methylpyridin-3-yl)phenyl)-6,7-dihydro-5H-pyrrolo[1,2-c]imidazol-5-yl)benzonitrile | 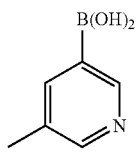 | 1.18 min (C) | 411.0 |
| Example 3-5 | 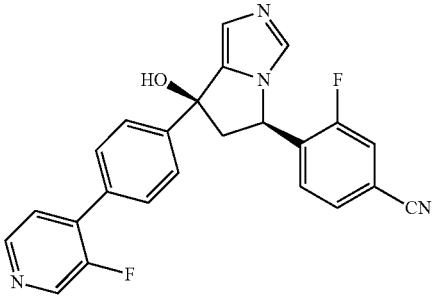<br>3-fluoro-4-((5R,7S)-7-(4-(3-fluoropyridin-4-yl)phenyl)-7-hydroxy-6,7-dihydro-5H-pyrrolo[1,2-c]imidazol-5-yl)benzonitrile | 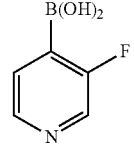 | 1.59 min (D) | 415.2 |

-continued

| Example # | Product | Reagent | LCMS-RT (condition) | MS (M + 1) |
|---|---|---|---|---|
| Example 3-6 | 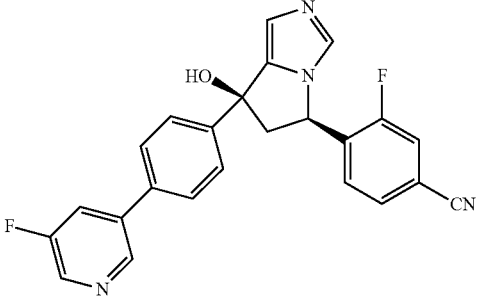 3-fluoro-4-((5R,7S)-7-(4-(5-fluoropyridin-3-yl)phenyl)-7-hydroxy-6,7-dihydro-5H-pyrrolo[1,2-c]imidazol-5-yl)benzonitrile | 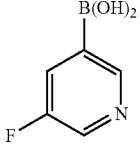 | 1.53 min (C) | 415.0 |
| Example 3-7 | 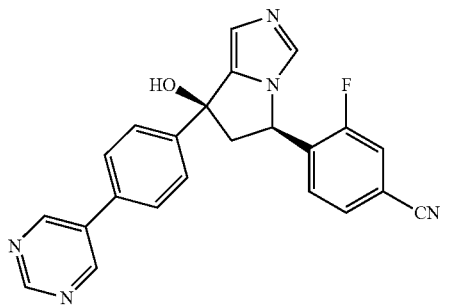 3-fluoro-4-((5R,7S)-7-hydroxy-7-(4-(pyrimidin-5-yl)phenyl)-6,7-dihydro-5H-pyrrolo[1,2-c]imidazol-5-yl)benzonitrile | 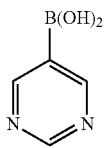 | 1.13 min (C) | 398.0 |
| Example 3-8 | 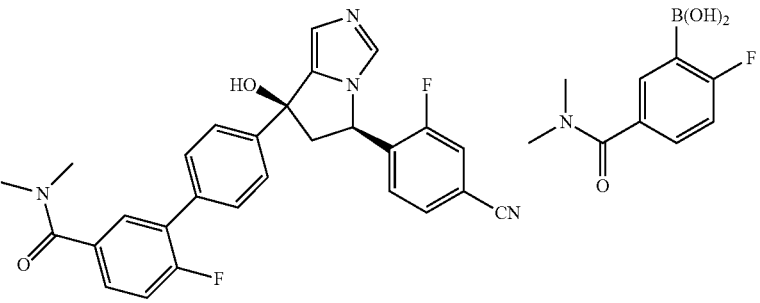 4'-((5R,7S)-5-(4-cyano-2-fluorophenyl)-7-hydroxy-6,7-dihydro-5H-pyrrolo[1,2-c]imidazol-7-yl)-6-fluoro-N,N-dimethylbiphenyl-3-carboxamide | 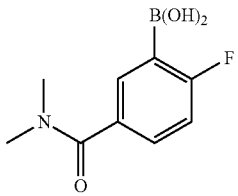 | 1.59 min (C) | 485.0 |

| Example # | Product | Reagent | LCMS-RT (condition) | MS (M + 1) |
|---|---|---|---|---|
| Example 3-9 | 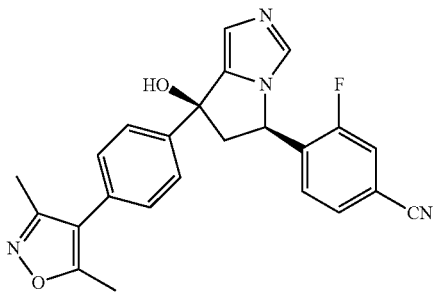<br>4-((5R,7S)-7-(4-(3,5-dimethylisoxazol-4-yl)phenyl)-7-hydroxy-6,7-dihydro-5H-pyrrolo[1,2-c]imidazol-5-yl)-3-fluorobenzonitrile | 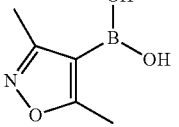 | 1.67 min (D) | 415.2 |
| Example 3-10 | 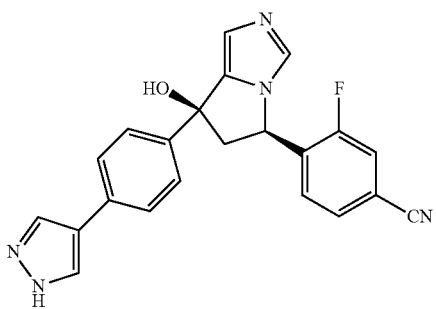<br>4-((5R,7S)-7-(4-(1H-pyrazol-4-yl)phenyl)-7-hydroxy-6,7-dihydro-5H-pyrrolo[1,2-c]imidazol-5-yl)-3-fluorobenzonitrile | 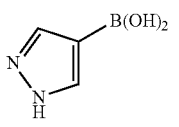 | 1.10 min (C) | 386.0 |
| Example 3-11 | 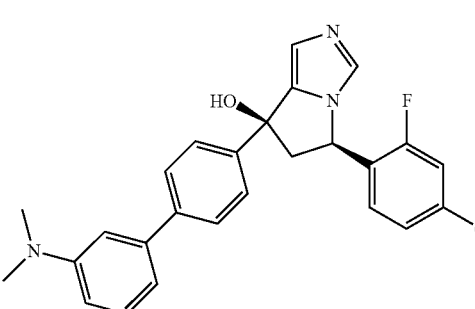<br>4-((5R,7S)-7-(3'-(dimethylamino)biphenyl-4-yl)-7-hydroxy-6,7-dihydro-5H-pyrrolo[1,2-c]imidazol-5-yl)-3-fluorobenzonitrile | 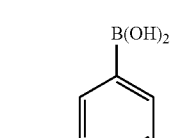 | 1.97 min (C) | 439.1 |

| Example # | Product | Reagent | LCMS-RT (condition) | MS (M + 1) |
|---|---|---|---|---|
| Example 3-12 | 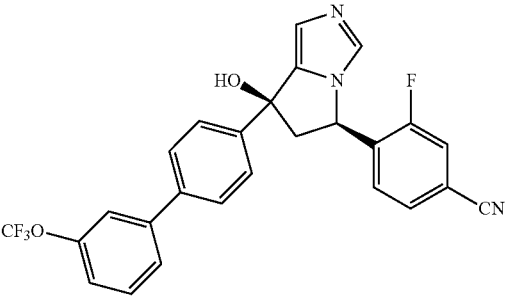<br>3-fluoro-4-((5R,7S)-7-hydroxy-7-(3′-(trifluoromethoxy)biphenyl-4-yl)-6,7-dihydro-5H-pyrrolo[1,2-c]imidazol-5-yl)benzonitrile | 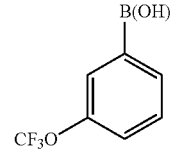 | 2.36 min (C) | 480.0 |
| Example 3-13 | 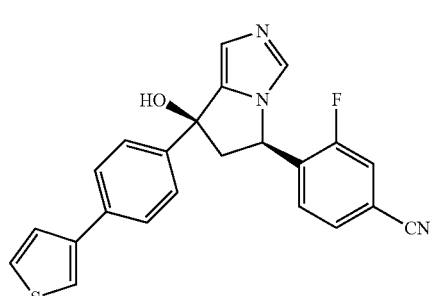<br>3-fluoro-4-((5R,7S)-7-hydroxy-7-(4-(thiophen-3-yl)phenyl)-6,7-dihydro-5H-pyrrolo[1,2-c]imidazol-5-yl)benzonitrile | 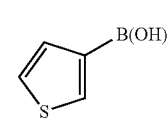 | 1.86 min (C) | 402.0 |
| Example 3-14 | 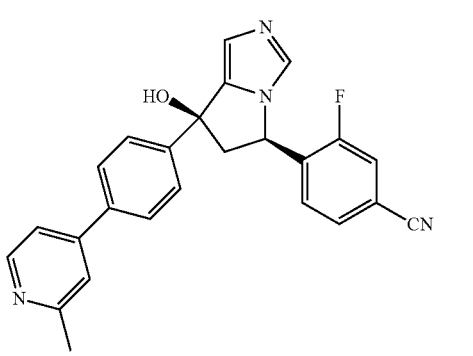<br>3-fluoro-4-((5R,7S)-7-hydroxy-7-(4-(2-methylpyridin-4-yl)phenyl)-6,7-dihydro-5H-pyrrolo[1,2-c]imidazol-5-yl)benzonitrile | 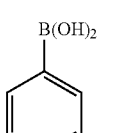 | 1.35 min (D) | 411.2 |

-continued

| Example # | Product | Reagent | LCMS-RT (condition) | MS (M + 1) |
|---|---|---|---|---|
| Example 3-15 | 3-fluoro-4-((5R,7S)-7-(4-(5-fluoropyridin-2-yl)phenyl)-7-hydroxy-6,7-dihydro-5H-pyrrolo[1,2-c]imidazol-5-yl)benzonitrile | 5-fluoropyridin-2-yl B(OH)$_2$ | 1.58 min (D) | 415.2 |
| Example 3-16 | 4-((5R,7S)-7-(4-(1H-pyrazol-3-yl)phenyl)-7-hydroxy-6,7-dihydro-5H-pyrrolo[1,2-c]imidazol-5-yl)-3-fluorobenzonitrile | 1H-pyrazol-3-yl B(OH)$_2$ | 1.32 min (C) | 386.1 |
| Example 3-17 | 4-((5R,7S)-7-(4'-(dimethylamino)biphenyl-4-yl)-7-hydroxy-6,7-dihydro-5H-pyrrolo[1,2-c]imidazol-5-yl)-3-fluorobenzonitrile | 4-(dimethylamino)phenyl B(OH)$_2$ | 2.02 min (C) | 439.1 |

| Example # | Product | Reagent | LCMS-RT (condition) | MS (M + 1) |
|---|---|---|---|---|
| Example 3-18 | 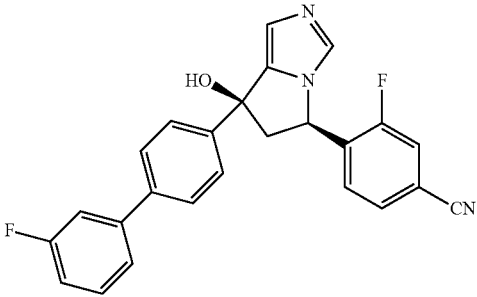<br>3-fluoro-4-((5R,7S)-7-(3'-fluorobiphenyl-4-yl)-7-hydroxy-6,7-dihydro-5H-pyrrolo[1,2-c]imidazol-5-yl)benzonitrile | 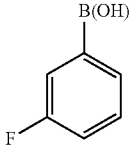 | 2.03 min (C) | 414.0 |

Example 3-2

1H NMR (500 MHz, DMSO-$d_6$) δ ppm 2.93 (dd, 1H), 3.48 (dd, 1H), 6.21 (dd, 1H), 6.68 (br. s., 1H), 7.37 (t, 1H), 7.58 (d, 2H), 7.66 (s, 1H), 7.79 (dd, 1H), 8.02 (d, 2H), 8.05 (d, 1H), 8.21 (d, 1H), 9.13 (br. s., 1H), 9.20 (d, 1H).

Example 3-3

1H NMR (500 MHz, DMSO-$d_6$) δ ppm 2.37 (s, 3H), 2.96 (dd, 1H), 3.50 (dd, 1H), 6.23 (dd, 1H), 6.75 (br. s., 1H), 7.39 (t, 1H), 7.51 (d, 2H), 7.61 (d, 1H), 7.64 (d, 2H), 7.70 (s, 1H), 7.80 (dd, 1H), 8.05 (dd, 1H), 8.52 (s, 1H), 8.57 (d, 1H), 9.16 (s, 1H).

Example 3-4

1H NMR (500 MHz, DMSO-$d_6$) δ ppm 2.40 (s, 3H), 2.93 (dd, 1H), 3.49 (dd, 1H), 6.22 (dd, 1H), 6.72 (br. s., 1H), 7.37 (t, 1H), 7.63 (d, 2H), 7.66 (s, 1H), 7.77-7.80 (m, 2H), 7.81 (d, 1H), 8.03 (br. s., 1H), 8.05 (br. s., 1H), 8.48 (s, 1H), 8.77 (s, 1H), 9.14 (br. s., 1H).

Example 3-6

1H NMR (500 MHz, DMSO-$d_6$) δ ppm 2.93 (dd, 1H), 3.49 (dd, 1H), 6.23 (dd, 1H), 6.74 (br. s., 1H), 7.38 (t, 1H), 7.63 (d, 2H), 7.67 (s, 1H), 7.80 (dd, 1H), 7.85 (d, 2H), 8.04 (dd, 1H), 8.08-8.12 (m, 1H), 8.60 (d, 1H), 8.83 (s, 1H), 9.16 (s, 1H).

Example 3-7

1H NMR (500 MHz, DMSO-$d_6$) δ ppm 2.94 (dd, 1H), 3.49 (dd, 1H), 6.23 (dd, 1H), 6.75 (br. s., 1H), 7.38 (t, 1H), 7.65 (s, 1H), 7.67 (s, 2H), 7.80 (dd, 1H), 7.87 (d, 2H), 8.04 (dd, 1H), 9.15 (br. s., 1H), 9.17 (s, 2H), 9.21 (s, 1H).

Example 3-8

1H NMR (500 MHz, DMSO-$d_6$) δ ppm 2.91-2.95 (m, 1H), 2.97 (d, 6H), 3.49 (dd, 1H), 6.22 (dd, 1H), 6.72 (br. s., 1H), 7.36-7.41 (m, 2H), 7.47 (t, 1H), 7.56 (dd, 1H), 7.62 (s, 4H), 7.67 (s, 1H), 7.80 (dd, 1H) 8.04 (dd, 1H), 9.12 (br. s., 1H).

Example 3-10

1H NMR (500 MHz, DMSO-$d_6$) δ ppm 2.90 (dd, 1H), 3.45 (dd, 1H), 6.20 (dd, 1H), 6.61 (br. s., 1H), 7.36 (t, 1H), 7.46 (d, 2H), 7.63 (d, 2H), 7.66 (s, 1H), 7.79 (dd, 1H), 8.04 (dd, 1H), 8.07 (br. s., 2H), 9.15 (s, 1H).

Example 3-11

1H NMR (500 MHz, DMSO-$d_6$) δ ppm 2.90-2.92 (m, 1H), 2.95 (s, 6H), 3.44-3.52 (m, 1H), 6.22 (dd, 1H), 6.68 (br. s., 1H), 6.76 (d, 1H), 6.91-6.95 (m, 2H), 7.27 (t, 1H), 7.38 (t, 1H), 7.56 (d, 2H), 7.67 (d, 2H), 7.68 (br. s., 1H), 7.80 (d, 1H), 8.04 (d, 1H), 9.17 (s, 1H).

Example 3-12

1H NMR (500 MHz, DMSO-$d_6$) δ ppm 2.91 (dd, 1H), 3.47 (dd, 1H), 6.18 (dd, 1H), 6.61 (br. s., 1H), 7.33 (t, 1H), 7.38 (d, 2H), 7.47 (t, 1H), 7.60 (d, 2H), 7.73 (s, 2H), 7.74-7.77 (m, 2H), 7.79 (d, 1H), 8.03 (dd, 1H), 8.91 (br. s., 1H).

Example 3-13

1H NMR (500 MHz, DMSO-$d_6$) δ ppm 2.91 (dd, 1H), 3.46 (dd, 1H), 6.19 (dd, 1H), 6.63 (br. s., 1H), 7.36 (t, 1H), 7.53 (d, 2H), 7.57 (dd, 1H), 7.62 (br. s., 1H), 7.65 (dd, 1H), 7.75 (d, 2H), 7.79 (dd, 1H), 7.90 (dd, 1H), 8.03 (dd, 1H), 9.08 (br. s., 1H).

Example 3-17

1H NMR (500 MHz, DMSO-$d_6$) δ ppm 2.88-2.92 (m, 1H), 2.93 (s, 6H), 3.47 (dd, 1H), 6.20 (dd, 1H), 6.63 (br. s., 1H), 6.80 (d, 2H), 7.37 (t, 1H), 7.52 (dd, 3H), 7.61 (d, 2H), 7.67 (s, 1H), 7.79 (dd, 1H), 8.04 (dd, 1H), 9.14 (s, 1H).

Example 3-18

1H NMR (500 MHz, DMSO-$d_6$) δ ppm 2.92 (dd, 1H), 3.48 (dd, 1H), 6.20 (dd, 1H), 6.67 (br. s., 1H), 7.18-7.24 (m, 1H), 7.36 (t, 1H), 7.48-7.51 (m, 1H), 7.51-7.56 (m, 2H), 7.59 (d, 2H), 7.62 (s, 1H), 7.75 (d, 2H), 7.79 (dd, 1H), 8.04 (dd, 1H), 9.06 (br. s., 1H).

Intermediate 4-1a tert-butyl 2-((5R,7S)-5-(4-cyano-2-fluorophenyl)-7-hydroxy-6,7-dihydro-5H-pyrrolo[1,2-c]imidazol-7-yl)acetate

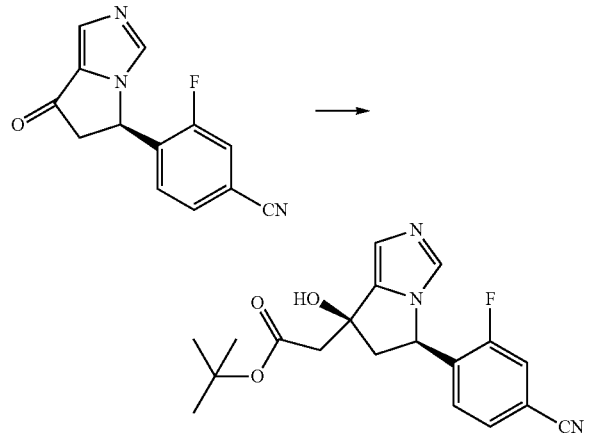

To a solution of (R)-3-fluoro-4-(7-oxo-6,7-dihydro-5H-pyrrolo[1,2-c]imidazol-5-yl)benzonitrile (2.0 g, 8.29 mmol) in THF (40.8 mL) was added a solution of 0.5M (2-tert-butoxy-2-oxoethyl)zinc(II) chloride in THF (39.8 mL, 19.90 mmol). The crude was stirred at room temperature for 2 hrs. To the crude was added and additional 0.5M 2-tert-butoxy-2-oxoethyl)zinc(II) chloride solution in THF (16.6 mL, 8.29 mmol). The crude was stirred at room temperature for 0.5 hr. The crude was quenched with saturated NH$_4$Cl and diluted in EtOAc. The organic layer was washed with brine, dried over MgSO$_4$, filtered, and concentrated. The crude was purified via HPLC 15% to 40% MeCN/H$_2$O, to give 365 mg of the entitled product as the major diastereomer. MS 358.2 (M+H), LCMS condition A, retention time 1.21 min. 1H NMR (400 MHz, CDCl$_3$) δ ppm 1.44 (s, 9H), 2.66-2.74 (m, 1H), 2.76-2.90 (m, 2H), 3.05-3.17 (m, 1H), 5.69 (dd, 1H), 6.96 (s, 1H), 7.12 (t, 1H), 7.31-7.38 (m, 2H), 7.44 (d, 1H).

Intermediate 4-1b 2-((5R,7S)-5-(4-cyano-2-fluorophenyl)-7-hydroxy-6,7-dihydro-5H-pyrrolo[1,2-c]imidazol-7-yl)acetic acid

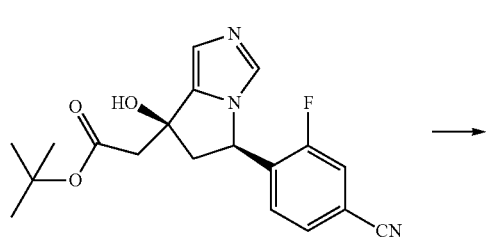

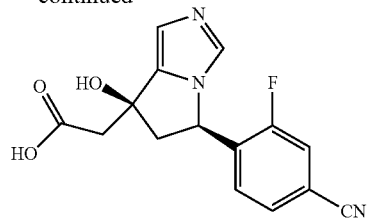

To a solution of (5R,7S)-5-(4-cyano-2-fluoro-phenyl)-7-hydroxy-6,7-dihydro-5H-pyrrolo[1,2-c]imidazol-7-yl]-acetic acid tert-butyl ester (365 mg, 1.02 mmol) in CH$_2$Cl$_2$ (2 mL) was added TFA (2 mL, 26.0 mmol) at room temperature. The crude was stirred at room temperature for 2 hrs. The crude was concentrated. The crude was diluted in ether (10 mL) and to the crude was added 4N HCl in dioxane (2 mL). The crude was shaken at room temperature and then concentrated. The crude was diluted with ether and HCl was added a second time and then the crude was concentrated to give 300 mg of the acid. This crude was used as is without further purification. MS 302.0 (M+H), LCMS condition A, retention time 0.65 min. 1H NMR (400 MHz, CD$_3$OD) δ ppm 2.82 (dd, 1H), 3.03-3.16 (m, 2H), 3.49 (dd, 1H), 6.17 (dd, 1H), 7.41 (t, 1H), 7.61 (s, 1H), 7.63 (d, 1H), 7.72 (dd, 1H), 8.90 (s, 1H). This acid was converted to the HCl salt via dilution of the crude acid in ethyl ether followed by the addition of excess 4 N HCl in ether, and concentration of solvent. This procedure was repeated to provide presumably 2-((5R,7S)-5-(4-cyano-2-fluorophenyl)-7-hydroxy-6,7-dihydro-5H-pyrrolo[1,2-c]imidazol-7-yl)acetic acid hydrochloride salt.

Example 4-1

2-((5R,7S)-5-(4-cyano-2-fluorophenyl-7-hydroxy-6,7-dihydro-5H-pyrrolo[1,2-c]imidazol-7-yl)-N-(4-fluorophenyl)acetamide

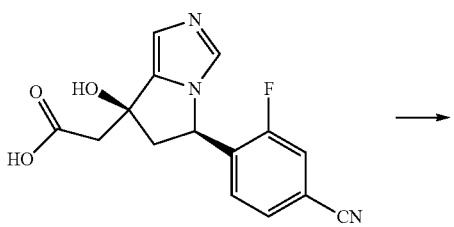

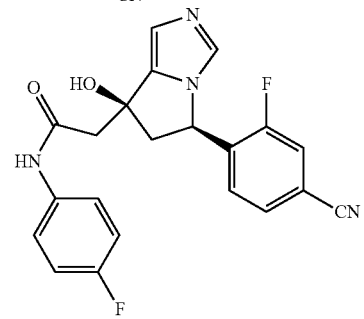

To a solution of 4-fluoro-phenylamine (0.149 mmol, 3.0 eq) in CH$_2$Cl$_2$(1 mL) was added a solution of 2-((5R,7S)-5-(4-cyano-2-fluorophenyl)-7-hydroxy-6,7-dihydro-5H-pyrrolo[1,2-c]imidazol-7-yl)acetic acid hydrochloride salt (15 mg, 0.050 mmol) in DMF (3 mL). To this solution was added HATU (60 mg, 0.16 mmol) and DIPEA (0.068 mL, 0.39 mmol). The crude was shaken using a shaker overnight at room temperature. The crude was concentrated using a genevac. The crude was purified via acidic HPLC (5% to 60% MeCN/H₂O). The collected product was filtered through a NaHCO₃ plug to remove TFA salt and concentrated to give 6.3 mg of the entitled product. MS 395.1 (M+H), LCMS condition A, retention time 1.34 min. 1H NMR (400 MHz, DMSO-d₆) δ ppm 2.57 (dd, 1H), 2.85-2.99 (m, 2H), 3.58 (dd, 1H), 5.65 (s, 1H), 5.81 (dd, 1H), 6.85 (s, 1H), 7.03-7.19 (m, 3H), 7.51 (s, 1H), 7.54-7.63 (m, 2H), 7.71 (d, 1H), 7.95 (d, 1H), 10.06 (s, 1H).

Following compounds are prepared using similar procedure as example 4-1 with appropriate reagents.

| Example # | Product | Reagent | LCMS-RT (condition) | MS (M + 1) |
|---|---|---|---|---|
| Example 4-2 | 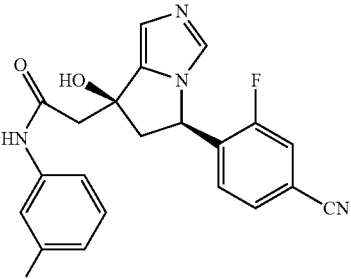<br>2((5R,7S)-5-(4-cyano-2-fluorophenyl)-7-hydroxy-6,7-dihydro-5H-pyrrolo[1,2-c]imidazol-7-yl)-N-(3-fluorophenyl)acetamide | 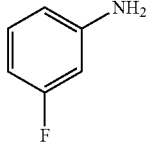 | 1.17 min (A) | 395.3 |
| Example 4-3 | 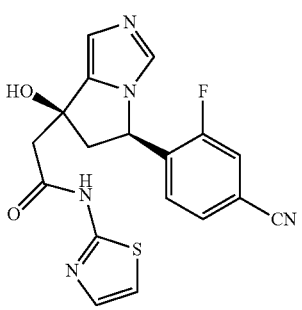<br>2-((5R,7S)-5-(4-cyano-2-fluorophenyl)-7-hydroxy-6,7-dihydro-5H-pyrrolo[1,2-c]imidazol-7-yl)-N-(thiazol-2-yl)acetamide | 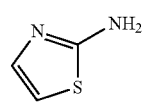 | 0.74 min (E) | 384.4 |
| Example 4-4 | 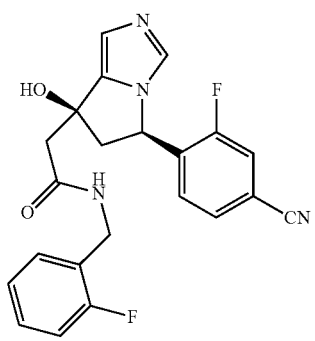<br>2-((5R,7S)-5-(4-cyano-2-fluorophenyl)-7-hydroxy-6,7-dihydro-5H-pyrrolo[1,2-c]imidazol-7-yl)-N-(2-fluorobenzyl)acetamide | 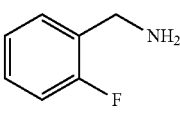 | 1.31 min (A) | 409.1 |

-continued

| Example # | Product | Reagent | LCMS-RT (condition) | MS (M + 1) |
|---|---|---|---|---|
| Example 4-5 | 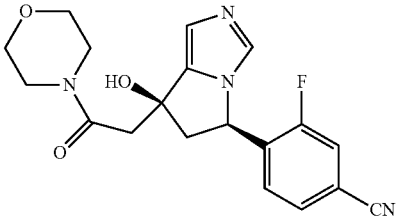<br>3-fluoro-4-((5R,7S)-7-hydroxy-7-(2-morpholino-2-oxoethyl)-6,7-dihydro-5H-pyrrolo[1,2-c]imidazol-5-yl)benzonitrile | 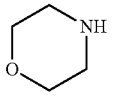 | 1.22 min (E) | 371.5 |
| Example 4-6 | 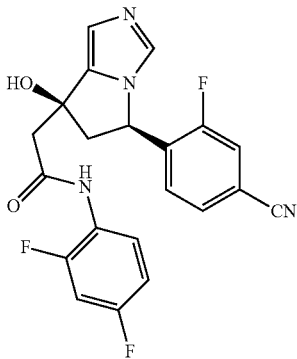<br>2-((5R,7S)-5-(4-cyano-2-fluorophenyl)-7-hydroxy-6,7-dihydro-5H-pyrrolo[1,2-c]imidazol-7-yl)-N-(2,4-difluorophenyl)acetamide | 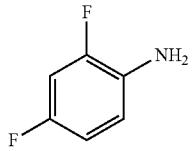 | 1.34 (A) | 413.0 |
| Example 4-7 | 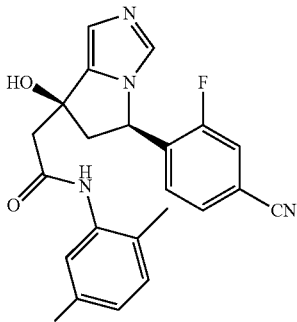<br>2-((5R,7S)-5-(4-cyano-2-fluorophenyl)-7-hydroxy-6,7-dihydro-5H-pyrrolo[1,2-c]imidazol-7-yl)-N-(5-fluoro-2-methylphenyl)acetamide | 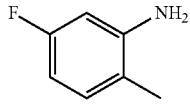 | 0.98 min (E) | 409.5 |

-continued

| Example # | Product | Reagent | LCMS-RT (condition) | MS (M + 1) |
|---|---|---|---|---|
| Example 4-8 | 2-((5R,7S)-5-(4-cyano-2-fluorophenyl)-7-hydroxy-6,7-dihydro-5H-pyrrolo[1,2-c]imidazol-7-yl)-N-(2,5-difluorophenyl)acetamide | 2,4-difluoroaniline | 0.98 min (E) | 413.4 |
| Example 4-9 | 2-((5R,7S)-5-(4-cyano-2-fluorophenyl)-7-hydroxy-6,7-dihydro-5H-pyrrolo[1,2-c]imidazol-7-yl)-N-ethylacetamide | ethylamine | 1.01 min (A) | 329.0 |
| Example 4-10 | 2-((5R,7S)-5-(4-cyano-2-fluorophenyl)-7-hydroxy-6,7-dihydro-5H-pyrrolo[1,2-c]imidazol-7-yl)-N-(4-methylpyridin-2-yl)acetamide | 2-amino-4-methylpyridine | 0.82 min (E) | 392.5 |

| Example # | Product | Reagent | LCMS-RT (condition) | MS (M + 1) |
|---|---|---|---|---|
| Example 4-11 | 3-fluoro-4-((5R,7S)-7-hydroxy-7-(2-(octahydroquinolin-1(2H)-yl)-2-oxoethyl)-6,7-dihydro-5H-pyrrolo[1,2-c]imidazol-5-yl)benzonitrile | | 1.54 min (A) | 423.1 |
| Example 4-12 | 3-fluoro-4-((5R,7S)-7-hydroxy-7-(2-oxo-2-(4-(trifluoromethyl)piperidin-1-yl)ethyl)-6,7-dihydro-5H-pyrrolo[1,2-c]imidazol-5-yl)benzonitrile | | 1.40 min (A) | 437.1 |
| Example 4-13 | 2-((5R,7S)-5-(4-cyano-2-fluorophenyl)-7-hydroxy-6,7-dihydro-5H-pyrrolo[1,2-c]imidazol-7-yl)-N-(2,3-dihydrobenzo[b][1,4]dioxin-6-yl)acetamide | | 1.29 min (A) | 435.1 |
| Example 4-14 | 2-((5R,7S)-5-(4-cyano-2-fluorophenyl)-7-hydroxy-6,7-dihydro-5H-pyrrolo[1,2-c]imidazol-7-yl)-N-(4-methoxyphenyl)acetamide | | 1.33 min (A) | 407.1 |

| Example # | Product | Reagent | LCMS-RT (condition) | MS (M + 1) |
|---|---|---|---|---|
| Example 4-15 | 2-((5R,7S)-5-(4-cyano-2-fluorophenyl)-7-hydroxy-6,7-dihydro-5H-pyrrolo[1,2-c]imidazol-7-yl)-N-(3-(trifluoromethoxy)phenyl) acetamide | CF₃O—C₆H₄—NH₂ | 1.16 min (E) | 461.4 |

Example 4-2

1H NMR (400 MHz, CDCl$_3$) (ppm 2.76 (dd, 1H), 2.89 (s, 2H), 3.15 (dd, 1H), 5.62 (dd, 1H), 6.70-6.80 (m, 1H), 6.77 (s, 1H), 7.03-7.21 (m, 3H), 7.29-7.40 (m, 3H), 8.98 (s, 1H) ppm.

Example 4-4

1H NMR (400 MHz, DMSO-d6) (ppm 2.51-2.59 (m, 1H), 2.77 (s, 2H), 3.48 (dd, 1H), 4.31 (d, 2H), 5.68-5.80 (m, 2H), 6.76 (br. s., 1H), 7.07-7.24 (m, 4H), 7.25-7.34 (m, 1H), 7.48 (br. s., 1H), 7.69 (dd, 1H), 7.93 (dd, 1H), 8.43-8.56 (m, 1H).

Example 4-6

1H NMR (400 MHz, DMSO-d$_6$) δ ppm 2.57 (dd, 1H), 2.96-3.01 (m, 2H), 3.51 (dd, 1H), 5.75 (s, 1H), 5.80 (dd, 1H), 6.84 (s, 1H), 7.02-7.09 (m, 1H), 7.12 (t, 1H), 7.26-7.35 (m, 1H), 7.50 (s, 1H), 7.69-7.74 (m, 1H), 7.76-7.83 (m, 1H), 7.93 (dd, 1H), 9.78 (s, 1H).

Example 4-13

1H NMR (400 MHz, DMSO-d$_6$) δ ppm 2.54-2.59 (m, 1H), 2.87 (dd, 2H), 3.51-3.60 (m, 1H), 4.11-4.27 (m, 4H), 5.63 (s, 1H), 5.79 (dd, 1H), 6.76 (d, 1H), 6.83 (s, 1H), 6.93 (dd, 1H), 7.09 (t, 1H), 7.20 (d, 1H), 7.50 (s, 1H), 7.71 (dd, 1H), 7.95 (dd, 1H), 9.83 (s, 1H).

Example 4-15

1H NMR (400 MHz, CD$_3$OD) δ ppm 2.76 (dd, 1H), 3.16-3.45 (m, 2H), 3.55 (dd, 1H), 5.90 (dd, 1H), 6.95-7.03 (m, 2H), 7.18 (1, 1H), 7.37 (t, 1H), 7.42-7.48 (m, 1H), 7.53 (d, 1H), 7.56 (s, 1H), 7.63 (d, 1H), 7.71 (s, 1H).

It can be seen that the compounds of this invention are useful as inhibitors of aldosterone synthase activity and therefore useful in the treatment of diseases and conditions mediated by aldosterone synthase such as the metabolic disorders disclosed herein.

It will be understood that the invention has been described by way of example only and modifications may be made whilst remaining within the scope and spirit of the invention.

What is claimed is:

1. A compound of Formula I:

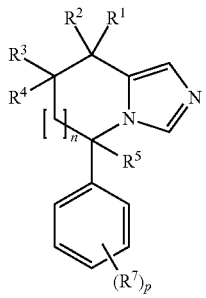

wherein:

$R^1$ and $R^2$ are independently OH, $C_{2-7}$alkenyloxy, $C_{2-7}$alkoxy, $C_{6-10}$aryl, aryl-$C_{2-7}$alkenyl, $C_{2-7}$alkenyl, $C_{3-8}$cycloalkyl, $C_{2-7}$alkynyl, $C_{1-7}$cycloalkyl-$C_{2-7}$alkynyl, heteroaryl, heteroaryl-$C_{1-7}$alkyl, —CH$_2$C(O)OH, —CH$_2$C(O)O—C$_{1-7}$alkyl, —CH$_2$C(O)NH—C$_{6-10}$aryl, —CH$_2$C(O)NH-heteroaryl, —CH$_2$C(O)-heterocyclyl, —CH$_2$C(O)NH-heterocyclyl, —CH$_2$C(O)NH—C$_{1-7}$alkyl, —C(O)O—C$_{1-7}$alkyl or —C(O)—C$_{1-7}$alkyl; wherein aryl, heterocyclyl and heteroaryl are optionally substituted with one or more $R^6$; with the proviso that one of $R^1$ and $R^2$ is other than $C_{1-7}$alkyl; or $R^1$ and $R^2$ form together =O, =N(OH) or =N(O—C$_{1-7}$alkyl); and $R^3$ and $R^4$ are independently selected from the group consisting of H, hydroxy, aryl-$C_{1-7}$alkyl or halo; wherein aryl is optionally substituted with one or more $R^8$; and $R^5$ is H, halo, hydroxy or $C_{2-7}$alkenyl; and $R^6$ and $R^8$ for each occurrence, is independently $C_{1-7}$alkyl, $C_{3-7}$cycloalkyl, CN, OH, NH$_2$, $C_{1-7}$alkylamino, di-($C_{1-7}$alkyl)amino, $C_{6-10}$aryl, heteroaryl, $C_{1-7}$alkoxy, halo, heterocyclyl, benzyloxy, halo-$C_{1-7}$alkoxy, —OS(O)$_2$—$C_{1-7}$alkyl or —OS(O)$_2$-halo $C_{1-7}$alkyl; wherein $C_{8-10}$aryl, heterocyclyl and heteroaryl are optionally substituted with one or more $R^9$; for each occurrence, $R^7$ is independently hydrogen, $C_{2-7}$alkenyl, $C_{3-8}$cycloalkyl, halo, nitro, cyano, NH$_2$, halo$C_{1-7}$alkyl, $C_{1-7}$alkoxy, $C_{3-8}$cycloalkoxy, $C_{8-10}$aryloxy, $C_{8-10}$aryl, heteroaryl, heteroaryl-$C_{1-7}$alkyl, heterocyclyl, heterocyclyl-$C_{1-7}$alkyl, C(O)OR$^{10}$ or N(R$^{11}$R$^{12}$), wherein said alkyl, alkenyl, alkoxy, aryl, heterocyclyl and heteroaryl each are optionally substituted with one or more substituent independently selected from $C_{1-7}$hydroxy, halo, halo $C_{1-7}$alkyl, $C_{1-7}$alkoxy, nitro, cyano, $C_{1-7}$alkylamino and $C_{1-7}$alkoxy-$C_{1-7}$alkyl;

$R^9$ for each occurrence, is independently $C_{1-7}$alkyl, $C_{1-7}$alkoxy, halo, halo$C_{1-7}$alkyl, NH$_2$, $C_{1-7}$alkylamino, di-($C_{1-7}$alkyl)amino, halo$C_{1-7}$alkoxy, CN, OH, C(O)O—C$_{1-7}$alkyl, C(O)O-halo$C_{1-7}$alkyl, carbamoyl, $C_{1-7}$-alkylaminocarbonyl or di-$C_{1-7}$alkylaminocarbonyl;

$R^{10}$, $R^{11}$ and $R^{12}$ for each occurrence are independently H, $C_{3-8}$cycloalkyl, halo-$C_{1-7}$alkyl, $C_{6-10}$aryl, $C_{6-10}$aryl-$C_{1-7}$alkyl, heteroaryl, heteroaryl-$C_{1-7}$alkyl, heterocyclyl, heterocyclyl-$C_{1-7}$alkyl; or $R^{11}$ and $R^{13}$ taken together with the nitrogen to which they are attached form a 3 to 8-membered heterocyclyl ring or a 5-membered heteroaryl ring;

n is 0 or 1;

p is 0, 1, 2, 3, 4 and 5;

or a pharmaceutically acceptable salt thereof.

2. The compound of claim 1 having Formula II:

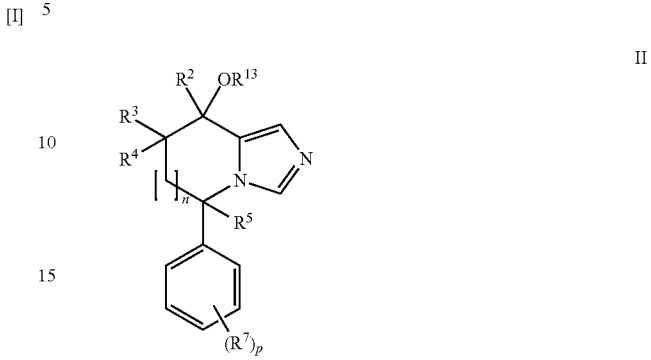

or a pharmaceutically acceptable salt thereof wherein $R^{13}$ is H, $C_{1-7}$alkyl or $C_{2-7}$alkenyl.

3. The compound of claim 2 wherein $R^2$ is $C_{6-10}$aryl, $C_{6-10}$aryl-$C_{2-7}$alkenyl, $C_{2-7}$alkenyl, $C_{3-8}$cycloalkyl, $C_{2-7}$alkynyl, $C_{1-7}$cycloalkyl-$C_{2-7}$alkynyl, heteroaryl, heteroaryl-$C_{1-7}$alkyl, —CH$_2$C(O)OH, —CH$_2$C(O)NH—C$_{6-10}$aryl, —CH$_2$C(O)NH-heteroaryl or —CH$_2$C(O)-heterocyclyl; wherein aryl, heteroaryl and heterocyclyl are optionally substituted with one or more $R^6$; or a pharmaceutically acceptable salt thereof.

4. The compound according to claim 2 having Formula IIA:

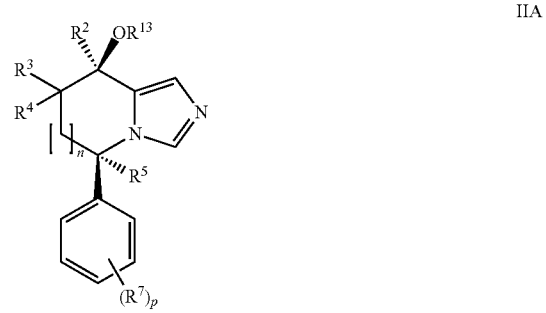

or a pharmaceutically acceptable salt thereof.

5. The compound of claim 2 having Formula III, IIIA or IIIB:

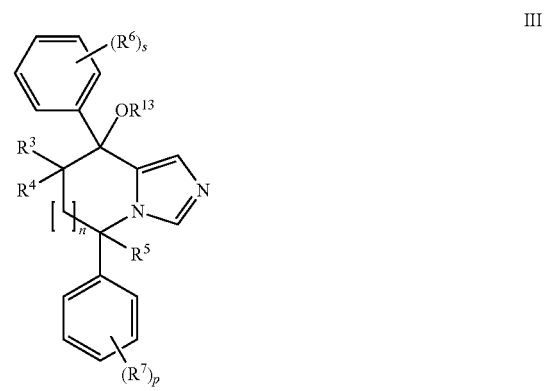

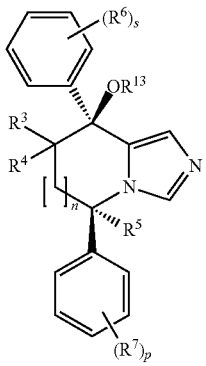

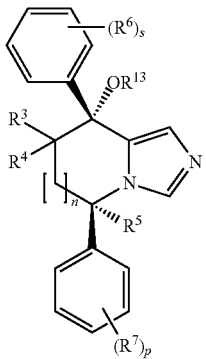

wherein s is 0, 1, 2, 3, 4 or 5; or a pharmaceutically acceptable salt thereof.

6. The compound of claim 1 wherein $R^2$ is heteroaryl, heteroary-$C_{1-7}$alkyl, $C_{6-10}$aryl or $C_{6-10}$aryl-$C_{1-7}$alkyl, wherein aryl or heteroaryl are optionally substituted with one or more $R^6$; or a pharmaceutically acceptable salt thereof.

7. The compound according to claim 1 wherein $R^2$ is —$CH_2C(O)NH$—$C_{6-10}$aryl, —$CH_2C(O)NH$-heteroaryl, $CH_2C(O)NH$-heterocyclyl, —$CH_2C(O)$heterocyclyl, —$CH_2C(O)OH$, —$CH_2C(O)O$—$C_{1-7}$alkyl, —$CH_2C(O)NH$—$C_{1-7}$alkyl, —$CH_2C(O)NH$-heterocyclyl wherein aryl, heteroaryl and heterocyclyl are optionally substituted with one or more $R^6$, or a pharmaceutically acceptable salt thereof.

8. The compound according to claim 1 having Formula IV, IVA or IVB:

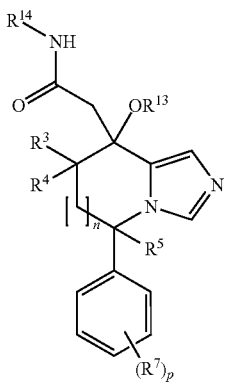 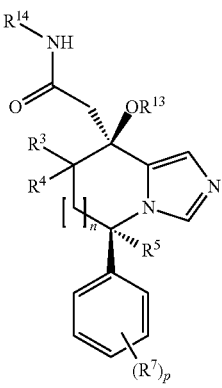

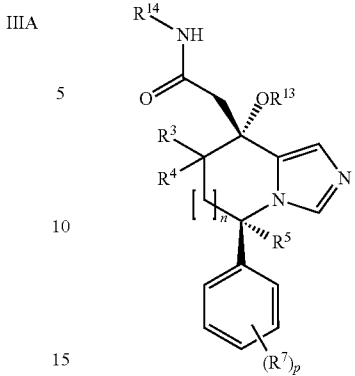

wherein $R^{14}$ is $C_{6-10}$aryl, $C_{6-10}$aryl-$C_{1-7}$alkyl, heteroaryl or heteroaryl-$C_{1-7}$alkyl, wherein aryl and heteroaryl are optionally substituted with one or more $R^6$, or a pharmaceutically acceptable salt thereof.

9. The compound of claim 1 wherein $R^3$ and $R^4$ are independently $C_{1-7}$alkyl or H and $R^5$ is H, or a pharmaceutically acceptable salt thereof.

10. The compound of claim 1 wherein p is 2, one of $R^7$ is para CN and the other is ortho F, or a pharmaceutically acceptable salt thereof.

11. A pharmaceutical composition comprising a compound according to claim 1, or a pharmaceutically acceptable salt thereof, and one or more pharmaceutically acceptable carriers.

12. A combination comprising a therapeutically effective amount of the compound according to claim 1 or a pharmaceutically acceptable salt thereof, and one or more therapeutically active agents selected from an HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

13. A method of modulating aldosterone synthase activity in a subject, wherein the method comprises administering to the subject a therapeutically effective amount of the compound according to claim 1, or a pharmaceutically acceptable salt thereof.

14. A method of treating a disorder or a disease in a subject mediated by aldosterone synthase wherein the method comprises administering to the subject a therapeutically effective amount of the compound according to claim 1, or a pharmaceutically acceptable salt thereof.

15. A method according to claim 14, wherein the disorder or the disease is selected from hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure, congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries.

\* \* \* \* \*

SEQUENCE LISTING

```
<160> NUMBER OF SEQ ID NOS: 1

<210> SEQ ID NO 1
<211> LENGTH: 18
<212> TYPE: PRT
<213> ORGANISM: Homo sapiens

<400> SEQUENCE: 1

Asp Trp Phe Lys Ala Phe Tyr Asp Lys Val Ala Glu Lys Phe Lys Glu
1               5                   10                  15

Ala Phe
```